(12) United States Patent
Urso et al.

(10) Patent No.: US 10,526,409 B2
(45) Date of Patent: *Jan. 7, 2020

(54) ANTIBODIES AGAINST HUMAN NKG2D AND USES THEREOF

(71) Applicant: Novo Nordisk A/S, Bagsvaerd (DK)

(72) Inventors: Birgitte Urso, Copenhagen (DK); Peter Andreas Nicolai Reumert Wagtmann, Rungsted Kyst (DK); Inger Lund Pedersen, Vanloese (DK); Anders Svensson, Malmoe (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,393

(22) Filed: Sep. 18, 2017

(65) Prior Publication Data

US 2018/0105594 A1    Apr. 19, 2018

Related U.S. Application Data

(63) Continuation of application No. 14/809,680, filed on Jul. 27, 2015, now abandoned, which is a continuation of application No. 12/747,095, filed as application No. PCT/EP2008/067499 on Dec. 15, 2008, now Pat. No. 9,127,064.

(30) Foreign Application Priority Data

Dec. 14, 2007 (EP) .................. PCT/EP2007/063979
Aug. 28, 2008 (EP) .................................. 08163163

(51) Int. Cl.
    *C07K 16/28* (2006.01)

(52) U.S. Cl.
    CPC ...... *C07K 16/2851* (2013.01); *C07K 2299/00* (2013.01); *C07K 2317/21* (2013.01); *C07K 2317/24* (2013.01); *C07K 2317/34* (2013.01); *C07K 2317/55* (2013.01); *C07K 2317/56* (2013.01); *C07K 2317/565* (2013.01); *C07K 2317/74* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| 7,879,985 B2 | 2/2011 | Urso et al. |
| 9,127,064 B2 | 9/2015 | Urso et al. |
| 2005/0158307 A1 | 7/2005 | Spies et al. |
| 2006/0280755 A1 | 12/2006 | Baron et al. |

FOREIGN PATENT DOCUMENTS

| CN | 1423700 A | 6/2003 |
| CN | 1634979 A | 7/2005 |
| RU | 2006105642 A | 6/2006 |
| WO | 0171005 A2 | 9/2001 |
| WO | 02068615 A2 | 9/2002 |
| WO | 2005097160 A2 | 10/2005 |
| WO | 2005115517 A2 | 12/2005 |
| WO | 2006024367 A2 | 3/2006 |
| WO | 2007005874 A2 | 1/2007 |
| WO | 2007042573 A2 | 4/2007 |
| WO | 2007130642 A2 | 11/2007 |

OTHER PUBLICATIONS

Gussow et al (Methods in Enzymology, 203: 99-121, 1991).*
Allez et al., "CD4+NKG2D+ T Cells in Crohn's Disease Mediate Inflammatory and Cytotoxic Responses Through MICA Interactions," Gastroenterology, vol. 132, pp. 2346-2358 (2007).
Andre et al., "Comparative analysis of human NK cell activation induced by NKG2D and natural cytotoxicity receptors," Eur. J. Immunol., vol. 34, pp. 961-971 (2004).
Bauer et al., "Activation of NK Cells and t Cells by NKG2D, a Receptor for Stress-Inducible MICA," Science, vol. 285, pp. 727-729 (Jul. 30, 1999).
Castriconi et al., "Transforming growth factor b1 inhibits expression of NKp30 and NKG2D receptors: Consequences for the NK-mediated killing of dendritic cells," PNAS, vol. 100, No. 7, pp. 4120-4125 (Apr. 1, 2003).
Experimental Report in connection with EP 2222706, 4 pages (Jan. 2015).
Geffroy-Luseau et al., "Allogeneic T lymphocytes as a source of peptide-dependent T cells specific for myeloma cells," International Immunology, vol. 17, No. 9, pp. 1193-120 (2005).
George et al., "Differential Effects of Anti-b2-Glycoprotein I Antibodies on Endothelial Cells and on the Manifestations of Experimental Antiphospholipid Syndrome," Circulation, vol. 97, pp. 900-906 (1998).
Groh et al., "Stimulation of T cell autoreactivity by anomalous expression of NKG2D and its MIC ligands in rheumatoid arthritis," PNAS, vol. 100, No. 16, pp. 9452-9457 (Aug. 5, 2003).
Gussow et al., "Humanization of Monoclonal Antibodies," Methods in Enzymology, vol. 203, pp. 99-121 (1991).

(Continued)

*Primary Examiner* — Brad Duffy

(74) *Attorney, Agent, or Firm* — Panitch Schwarze Belisario & Nadel LLP

(57) ABSTRACT

The present invention provides isolated anti-human NKG2D monoclonal antibodies useful for therapeutic applications in humans. Typically, the antibodies are fully human or humanized to minimize the risk for immune responses against the antibodies when administered to a patient. Preferred antibodies include human monoclonal antibodies MS and 21F2. As described herein, other antigen-binding molecules such as, e.g., antigen-binding antibody fragments, antibody derivatives, and multi-specific molecules, can be designed or derived from such antibodies.

13 Claims, 33 Drawing Sheets

Specification includes a Sequence Listing.

(56) References Cited

OTHER PUBLICATIONS

Kwong et al., "Generation, Affinity Maturation, and Characterization of a Human Anti-Human NKG2D Monoclonal Antibody with Dual Antagonistic and Agonistic Activity," Journal of Molecular Biology, vol. 384, pp. 1143-1156 (2008).

Lippincott-Schwartz, "Antibodies as Cell Biological Tools," Current Protocols in Cell Biology, 16.0.1-16.0.2, 2 pages (2002).

Maasho et al., "Cutting Edge: NKG2D is a Costimulatory Receptor for Human Naive CD8 + T Cells," The Journal of Immunology, vol. 174, pp. 4480-4484 (2005).

Mincheva-Nilsson et al., "Placenta-Derived Soluble MHC Class I Chain-Related Molecules Down_Regulate NKG2D Receptor on Peripheral Blood Mononuclear Cells during Human Pregnancy: A Possible Novel Immune Escape Mechanism for Fetal Survival," The Journal of Immunology, vol. 176, pp. 3585-3592 (2006).

Ogasawara et al., "NKG2D Blockade Prevents Autoimmune Diabetes in NOD Mice," Immunity, vol. 20, pp. 757-767 (Jun. 2004).

Pende et al., "Role of NKG2D in tumor cell lysis mediated by human NK cells: cooperation with natural cytotoxicity receptors and capability of recognizing tumors of nonepithelial origin," Eur. J. Immunol., vol. 31, pp. 1076-1086 (2001).

Roitt et al, "Antigen Recognition," Immunology, 5th Ed., pp. 110-113 (2000).

Sinden et al., "Advances in Genome Biology," Genes and Genomes, vol. 5A, pp. 63-64 (1998).

Tanaka et al., "Cytolytic activity and regulatory functions of inhibitory NK cell receptor-expressing T cells expanded from granulocyte colony-stimulating factor-mobilized peripheral blood mononuclear cells," Blood, vol. 104, No. 3, pp. 768-774 (Aug. 1, 2004).

Vikhrova et al., "Combinatorial Libraries of Phage Antibodies: Application for Analysis of Gene Segments Encoding Variable Domains of Autoantibodies to Tumor Necrosis Factor," Molecular Biology, vol. 45, No. 1, pp. 82-92 (2011).

Winkler et al., "Changing the Antigen Binding Specificity by Single Point Mutations of an Anti-p24 (HIV-2) Antibody," J. Immunol., vol. 165, pp. 4505-4514 (2000).

* cited by examiner

Fig. 4A

16F16 heavy chain (IgG4):

EVQLVESGGGLVKPGGSLRLSCAASGFTFS<u>SYSMN</u>WVRQAPGKGLEWVSS<u>ITSSSSYIY</u>-<u>YADSVKG</u>RFTISRDNAKNSLYLQMNSLRAEDTAVYYCAR<u>DRRYFDWFPLDYR</u>-GQGTLVTVSSASTKGPSVFPLAPCSRSTSESTAALGCLVKDYFPEPVTVSWNSGALTSGVHT-FPAVLQSSGLYSLSSVVTVPSSSLGTKTYTCNVDHKPSNTKVDKRVESKYGPPCPPCPAPE-FLGGPSVFLFPPKPKDTLMISRTPEVTCVVVDVSQEDPEVQFNWYVDGVEVHNAK-TKPREEQFNSTYRVVSVLTVLHQDWLNGKEYKCKVSNKGLPSSIEK-TISKAKGQPREPQVYTLPPSQEEMTKNQVSLTCLVKGFYPSDIAVEWESNGQPEN-NYKTTPPVLDSDGSFFLYSRLTVDKSRWQEGNVFSCSVMHEALHNHYTQKSLSLSLGK (SEQ ID NO:7)

16F16 light chain:

DIQMTQSPSSLSASVGDRVTITC<u>RASQGISSWLA</u>WYQQKPEKAPKSLIY<u>AAS</u>-<u>SLQS</u>GVPSRFSGSGSGTDFTLTISSLQPEDFATYYC<u>QQYNGYPYT</u>FGQGTKLEIKRT-VAAPSVFIFPPSDEQLKSGTASVVCLLNNFYPREAKVQWKVDNALQSGNSQESVTE-QDSKDSTYSLSSTLTLSKADYEKHKVYACEVTHQGLSSPVTKSFNRGEC (SEQ ID NO:8)

16F31 heavy chain (IgG4):

EVQLVESGGGVVRPGGSLRLSCAASGFTFD<u>DYGMT</u>WVRQAPGKGLEWVSG<u>IN</u>-<u>WNGGSTGYADSVKG</u>RFTISRDNAKNSLYLQMNSLRAEDTALYYCAR<u>ERELYYYY</u>-<u>GLDV</u>WGQGTTVTVSSASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPCPPCPAPE-FLGGPSVFLFPPKPKDTLMISRTPEVTCVVVDVSQEDPEVQFNWYVDGVEVHNAK-TKPREEQFNSTYRVVSVLTVLHQDWLNGKEYKCKVSNKGLPSSIEK-TISKAKGQPREPQVYTLPPSQEEMTKNQVSLTCLVKGFYPSDIAVEWESNGQPEN-NYKTTPPVLDSDGSFFLYSRLTVDKSRWQEGNVFSCSVMHEALHNHYTQKSLSLSLGK (SEQ ID NO:9)

16F31 light chain:

EIVLTQSPGTLSLSPGERATLSC<u>RASQSVSSSYLA</u>WYQQKPGQAPRLLIY<u>GASSRATGIP</u>-DRFSGSGSGTDFTLTISRLEPEDFAVYYC<u>QQYGSSPFT</u>FGPGTKVDIKRT-VAAPSVFIFPPSDEQLKSGTASVVCLLNNFYPREAKVQWKVDNALQSGNSQESVTE-QDSKDSTYSLSSTLTLSKADYEKHKVYACEVTHQGLSSPVTKSFNRGEC (SEQ ID NO:10)

Fig. 4B

MS Heavy Chain (IgG4):
**QVHLQESGPGLVKPSETLSLTCTVSDDSIS-
S<u>YYWS</u>WIRQPPGKGLEWIG<u>HISYSGSANYNPSLKSR</u>VTIS-
VDTSKNQFSLKLSSVTAADTAVYYCAN<u>WDDAF-
NI</u>WGQGTMVTVSS**ASTKGPSVFPLAPCSRSTSESTAALGCLVKDYFPEPVTVSWNSGALTSGV
HTFPAVLQSSGLYSLSSVVTVPSSSLGTKTYTCNVDHKP-
SNTKVDKRVESKYGPPCPPCPAPEFLGGPSVFLFPPKPKDTLMIS-
RTPEVTCVVVDVSQEDPEVQFNWYVDGVEVHNAK-
TKPREEQFNSTYRVVSVLTVLHQDWLNGKEYKCKVSNKGLPSSIEK-
TISKAKGQPREPQVYTLPPSQEEMTKNQVSLTCLVKGFYPSDIAVEWESNGQPEN-
NYKTTPPVLDSDGSFFLYSRLTVDKSRWQEGNVFSCSVMHEALHNHYTQKSLSLSLGK (SEQ
ID NO:40)

MS Light Chain:
**EIVLTQSPGTLSLSPGERATLSC<u>RASQSVSSSYLA</u>WYQQKPGQAPRLLIY<u>GASSRAT</u>GIP-
DRFSGSGSGTDFTLTISRLEPEDFAVYYC<u>QQYGSSPWT</u>FGQGTKVEIKR**T-
VAAPSVFIFPPSDEQLKSGTASVVCLLNNFYPREAKVQWKVDNALQSGNSQESVTE-
QDSKDSTYSLSSTLTLSKADYEKHKVYACEVTHQGLSSPVTKSFNRGEC (SEQ ID
NO:41)

21F2 Heavy chain (IgG4):
**EVQLVQSGAEVKEPGESLKISCKNSGYSFT<u>NYWVG</u>WVRQMPGKGLEWMG<u>IIYPGDSD-
TRYSPSFQG</u>QVTISADKSINTAYLQWS-
SLKASDTAMYYCG<u>RLTMFRGIIIGYFDY</u>WGQGTLVTVSS**ASTKGPSVFPLAPCSRSTSESTAA
LGCLVKDYFPEPVTVSWNSGALTSGVHTFPAVLQSSGLYSLSSVVTVPSSSLGTK-
TYTCNVDHKPSNTKVDKRVESKYGPPCPPCPAPEFLGGPSVFLFPPKPKDTLMIS-
RTPEVTCVVVDVSQEDPEVQFNWYVDGVEVHNAK-
TKPREEQFNSTYRVVSVLTVLHQDWLNGKEYKCKVSNKGLPSSIEK-
TISKAKGQPREPQVYTLPPSQEEMTKNQVSLTCLVKGFYPSDIAVEWESNGQPEN-
NYKTTPPVLDSDGSFFLYSRLTVDKSRWQEGNVFSCSVMHEALHNHYTQKSLSLSLGK (SEQ
ID NO:42)

21F2 Light chain:
**EIVLTQSPATLSLSPGERATLSC<u>RASQSVSSYLA</u>WYQQKPGQAPRLLIY<u>DASNRAT</u>-
GIPARFSGSGSGTDFTLTISSLEPEDFAVYYC<u>QQRSNWPWT</u>FGQGTKVEIKR**T-
VAAPSVFIFPPSDEQLKSGTASVVCLLNNFYPREAKVQWKVDNALQSGNSQESVTE-
QDSKDSTYSLSSTLTLSKADYEKHKVYACEVTHQGLSSPVTKSFNRGEC (SEQ ID
NO:43)

Fig. 5A: 16F16 Heavy Chain

```
         1         2         3         4         5         6
12345678901234567890123456789012345AB6789012345678901 2ABC34567890
EVQLVESGGGLVKPGGSLRLSCAASGFTFSSYSMN  WVRQAPGKGLEWVSSITS  SSSYIYYA
EVQLVESGGGLVKPGGSLRLSCAASGFTFSSYSMN  WVRQAPGKGLEWVSSISS  SSSYIYYA
         7         8         9        10        11
1234567890123456789012ABC34567890123 4567890ABCDEFGHIJK1234567890  <- Kabat
DSVKGRFTISRDNAKNSLYLQMNSLRAEDTAVYYCARDRRYFDWFPL     DYRGQGTLVTVSS  16F16 VH
DSVKGRFTISRDNAKNSLYLQMNSLRAEDTAVYYCAR/        /     DYWGQGTLVTVSS  VH3_21/D3-9/JH4
```

Fig. 5B: 16F16 Light Chain

```
         1         2         3         4         5         6
1234567890123456789012 34567ABCDEF8901234567890123456 7 8901234567890
DIQMTQSPSSLSASVGDRVTITCRASQ        GISSWLAWYQQKPEKAPKSLIYAASSLQSGVPS
DIQMTQSPSSLSASVGDRVTITCRASQ        GISSWLAWYQQKPEKAPKSLIYAASSLQSGVPS
         7         8         9        10
12345678901234567890123456789012345AB67890123456789  <- The Kabat
RFSGSGSGTDFTLTISSLQPEDFATYYCQQYNGYP    YTFGQGTKLEIK  16F16 VL
RFSGSGSGTDFTLTISSLQPEDFATYYCQQYNSYP//  YTFGQGTKLEIK  VKI_L15/JK2
```

Fig. 5C: 16F31 Heavy Chain

```
         1         2         3         4         5         6
123456789012345678901234567890 12345AB6789012345678901 2ABC34567890
EVQLVESGGGVVRPGGSLRLSCAASGFTFDDYGMT  WVRQAPGKGLEWVSGINW  NGGSTGYA
EVQLVESGGGVVRPGGSLRLSCAASGFTFDDYGMS  WVRQAPGKGLEWVSGINW  NGGSTGYA
         7         8         9        10        11
1234567890123456789012ABC34567890123 4567890ABCDEFGHIJK1234567890  <- Kabat
DSVKGRFTISRDNAKNSLYLQMNSLRAEDTALYYCARERELYYYYGL     DVWGQGTTVTVSS  16F31 VH
DSVKGRFTISRDNAKNSLYLQMNSLRAEDTALYHCAR/   /YYYYGM    DVWGQGTTVTVSS  VH3_20/D3-10/JH6
```

Fig 5D: 16F31 Light Chain

```
         1         2         3           4         5         6
12345678901234567890123456 7ABCDEF8901234 5678901234567890 1234567890
EIVLTQSPGTLSLSPGERATLSCRASQS    VSSSYLAWYQQKPGQAPRLLIYGASSRATGIPD
EIVLTQSPGTLSLSPGERATLSCRASQS    VSSSYLAWYQQKPGQAPRLLIYGASSRATGIPD
         7         8         9         10
1234567890123456789012345678901234 5AB67890123456789  <- Kabat
RFSGSGSGTDFTLTISRLEPEDFAVYYCQQYGSSP  FTFGPGTKVDIK  16F31 VL
RFSGSGSGTDFTLTISRLEPEDFAVYYCQQYGSSP//FTFGPGTKVDIK  VKIII_A27/JK3
```

Fig. 5E: MS Heavy Chain

```
         1         2         3         4         5         6
12345678901234567890123456789012345678901234567890 1234567890  Kabat
QVHLQESGPGLVKPSETLSLTCTVSDDSISSYYWSWIRQPPGKGLEWIGHISYSGSANYN  MS VH
QVQLQESGPGLVKPSETLSLTCTVSGGSISSYYWSWIRQPPGKGLEWIGYIYYSGSTNYN  VH4_59
         7         8         9         10        11
12345678901234567890 12ABC34567890123A 45678901234567890123    Kabat
PSLKSRVTISVDTSKNQFSLKLSSVTAADTAVYYCA_  NWD DAFNIWGQGTMVTVSS    MS VH
PSLKSRVTISVDTSKNQFSLKLSSVTAADTAVYYCAR/NWG/DAFDIWGQGTMVTVSS    VH4_59/D7_27_3/JH3
```

Fig. 5F: MS Light Chain

```
         1         2         3         4         5         6
1234567890123456789012345 67A8901234567890123456789 01234567890  Kabat
EIVLTQSPGTLSLSPGERATLSCRASQSVSSSYLAWYQQKPGQAPRLLIYGASSRATGIPD  MS Light Chain
EIVLTQSPGTLSLSPGERATLSCRASQSVSSSYLAWYQQKPGQAPRLLIYGASSRATGIPD  VKIII_A27
         7         8         9         10
1234567890123456789012345678901 2345 678901234567                Kabat
RFSGSGSGTDFTLTISRLEPEDFAVYYCQQYGSSP  WTFGQGTKVEIK                MS VL
RFSGSGSGTDFTLTISRLEPEDFAVYYCQQYGSSP/WTFGQGTKVEIK                VKIII_A27/JK1
```

Fig. 5G: 21F2 Heavy Chain

```
         1         2         3         4         5         6
123456789012345678901234567890123456789012345678901 2A34567890  Kabat
EVQLVQSGAEVKEPGESLKISCKNSGYSFTNYWVGWVRQMPGKGLEWMGIIYPGDSDTRYS  21F2 Heavy Chain
EVQLVQSGAEVKKPGESLKISCKGSGYSFTSYWIGWVRQMPGKGLEWMGIIYPGDSDTRYS  VH5_51
         7         8         9         10        11
12345678901234567890 12ABC345678901234 567890ABCDEF1234567890123   Kabat
PSFQGQVTISADKSINTAYLQWSSLKASDTAMYYCGR LTMFRGIIGYFDYWGQGTLVTVSS    21F2 Heavy Chain
PSFQGQVTISADKSISTAYLQWSSLKASDTAMYYCAR/ITMVRGII/YFDYWGQGTLVTVSS    VH5_51/D3_10_R3/JH4
```

Fig. 5H: 21F2 Light Chain

```
         1         2         3         4         5         6
123456789012345678901234567890123456789012345678901234567890  Kabat
EIVLTQSPATLSLSPGERATLSCRASQSVSSYLAWYQQKPGQAPRLLIYDASNRATGIPA  21F2 Light Chain
EIVLTQSPATLSLSPGERATLSCRASQSVSSYLAWYQQKPGQAPRLLIYDASNRATGIPA  VKIII_L6
         7         8         9        10
1234567890123456789012345678901234 5 678901234567              Kabat
RFSGSGSGTDFTLTISSLEPEDFAVYYCQQRSNWP WTFGQGTKVEIK               21F2 Light Chain
RFSGSGSGTDFTLTISSLEPEDFAVYYCQQRSNWP/WTFGQGTKVEIK               VKIII_L6/J
```

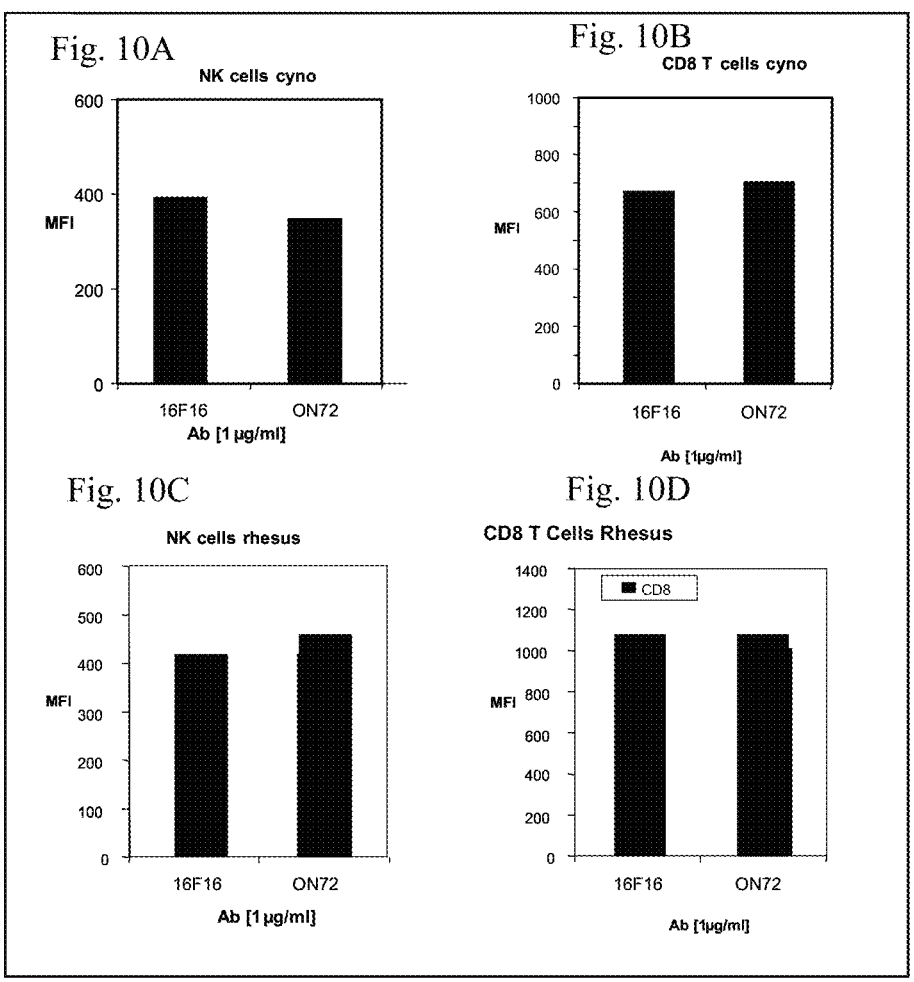

Fig. 21A

NKG2D monomer unit 1

```
  1    MGWIRGRRSR  HSWEMSEFHN  YNLDLKKSDF  STRWQKQRCP  VVKSKCRENA
 51    SPFFFCCFIA  VAMGIRFIIM  VTIWSAVFLN  SLFNQEVQIP  LTESYCGPCP
101    KNWICYKNNC  YQFFDESKNW  YESQASCMSQ  NASLLKVYSK  EDQDLLKLVK
151    SYHWMGLVHI  PTNGSWQWED  GSILSPNLLT  IIEMQKGDCA  LYASSFKGYI
201    ENCSTPNTYI  CMQRTV
```

NKG2D monomer unit 2

```
  1    MGWIRGRRSR  HSWEMSEFHN  YNLDLKKSDF  STRWQKQRCP  VVKSKCRENA
 51    SPFFFCCFIA  VAMGIRFIIM  VTIWSAVFLN  SLFNQEVQIP  LTESYCGPCP
101    KNWICYKNNC  YQFFDESKNW  YESQASCMSQ  NASLLKVYSK  EDQDLLKLVK
151    SYHWMGLVHI  PTNGSWQWED  GSILSPNLLT  IIEMQKGDCA  LYASSFKGYI
201    ENCSTPNTYI  CMQRTV
```

Fig. 21B

NKG2D monomer unit 1

```
  1   MGWIRGRRSR HSWEMSEFHN YNLDLKKSDF STRWQKQRCP VVKSKCRENA
 51   SPFFFCCFIA VAMGIRFIIM VTIWSAVFLN SLFNQEVQIP LTESYCGPCP
101   KNWICYKNNC YQFFDESKNW YESQASCMSQ NASLLKVYSK EDQDLLKLVK
151   SYHWMGLVHI PTNGSWQWED GSILSPNLLT IIEMQKGDCA LYASSFKGYI
201   ENCSTPNTYI CMQRTV
```

NKG2D monomer unit 2

```
  1   MGWIRGRRSR HSWEMSEFHN YNLDLKKSDF STRWQKQRCP VVKSKCRENA
 51   SPFFFCCFIA VAMGIRFIIM VTIWSAVFLN SLFNQEVQIP LTESYCGPCP
101   KNWICYKNNC YQFFDESKNW YESQASCMSQ NASLLKVYSK EDQDLLKLVK
151   SYHWMGLVHI PTNGSWQWED GSILSPNLLT IIEMQKGDCA LYASSFKGYI
201   ENCSTPNTYI CMQRTV
```

Fig. 21C

NKG2D monomer unit 1

```
  1    MGWIRGRRSR HSWEMSEFHN YNLDLKKSDF STRWQKQRCP VVKSKCRENA
 51    SPFFFCCFIA VAMGIRFIIM VTIWSAVFLN SLFNQEVQIP LTESYCGPCP
101    KNWICYKNNC YQFFDESKNW YESQASCMSQ NASLLKVYSK EDQDLLKLVK
151    SYHWMGLVHI PTNGSWQWED GSILSPNLLT IIEMQKGDCA LYASSFKGYI
201    ENCSTPNTYI CMQRTV
```

NKG2D monomer unit 2

```
  1    MGWIRGRRSR HSWEMSEFHN YNLDLKKSDF STRWQKQRCP VVKSKCRENA
 51    SPFFFCCFIA VAMGIRFIIM VTIWSAVFLN SLFNQEVQIP LTESYCGPCP
101    KNWICYKNNC YQFFDESKNW YESQASCMSQ NASLLKVYSK EDQDLLKLVK
151    SYHWMGLVHI PTNGSWQWED GSILSPNLLT IIEMQKGDCA LYASSFKGYI
201    ENCSTPNTYI CMQRTV
```

ANTIBODIES AGAINST HUMAN NKG2D AND USES THEREOF

CROSS-REFERENCE TO RELATED APPLICATIONS

This application is a continuation of U.S. patent application Ser. No. 14/809,860, filed on Jul. 27, 2015, which is a continuation of U.S. patent application Ser. No. 12/747,095, filed on Jul. 9, 2010 which is a 35 U.S.C. § 371 national stage application of International Patent Application PCT/EP2008/067499 (published as WO 2009/077483), filed Dec. 15, 2008, which claimed priority to European Patent Applications PCT/EP2007/063979, filed Dec. 14, 2007 and 08163163.2, filed Aug. 28, 2008. Each disclosure is incorporated herein by reference in its entirety.

FIELD OF THE INVENTION

The present invention relates to antibodies against human NKG2D (hNKG2D) and their use in treating or preventing diseases and disorders in human patients.

INCORPORATION-BY-REFERENCE OF THE SEQUENCE LISTING

In accordance with 37 C.F.R. § 1.52(e)(5), Applicants enclose herewith the Sequence Listing for the above-captioned application entitled "7923US01_SeqList", created on Jul. 1, 2015. The Sequence Listing is made up of 65,397 bytes, and the information contained in the attached "SEQUENCE LISTING" is identical to the information in the specification as originally filed. No new matter is added.

BACKGROUND OF THE INVENTION

The immunoreceptor NKG2D is normally expressed on human $CD8^+$ T cells and NK cells. On pre-activated $CD8^+$ cells, the human NKG2D (hNKG2D) homodimeric receptor functions as a co-stimulator of TCR and CD28+ TCR signaling via its DAP10 association, whereas in NK cells it functions as a direct activator. Various ligands for hNKG2D have been identified and characterized, including the MHC Class I-related ligands MICA and MICB, the UL16-binding protein (ULBP) family, and the retinoic acid early transcript-1 (RAET1) family.

In chronic autoimmune diseases such as rheumatoid arthritis, hNKG2D is expressed on a sub-set of $CD4^+$ $CD28^-$ T cells and is involved in stimulation of their proliferation and IFNγ production, and MIC expression is upregulated (Groh et al., PNAS 2003; 100:9452). It has also been shown that CD4+ hNKG2D-expressing T cells in Crohn's disease mediate inflammatory and cytotoxic responses through MICA interactions (Allez et al., Gastroenterology 2007; 132:2346-2358). An initial suggestion that NKG2D is an essential driver in autoimmune inflammation came from the prevention and treatment of the inflammation leading to diabetes in a murine model of diabetes (NOD mice) by a monoclonal antibody (mAb) binding to and blocking murine NKG2D (CX5) (Ogasawara et al., Immunity 2004; 20:757-767), suggesting therapeutic applications for anti-NKG2D antibodies. Such applications have been described in, e.g., US20050158307, WO2005097160, WO2005115517, and WO2006024367.

While murine mAbs against human NKG2D have been described (see, e.g., Pende et al., Eur J Immunol 2001; 31:1076-86, WO02068615; Bauer et al., Science 1999;285: 727-9; Castriconi et al., PNAS 2003; 100:4120-25; and André et al., Eur J Immunol 2004; 34:1-11) or are commercially available (e.g., antibody 149810 from R&D Systems, Minn., USA, and ON72 from Beckman Coulter Inc.), these are immunogenic. The only fully human anti-NKG2D mAb described in the literature reportedly had both agonistic and antagonistic effects on NKG2D-signaling (Kwong et al., J Mol Biol 2008; 384:1143-1156), rendering it less suitable as a therapeutic agent for inflammatory and/or autoimmune disorders.

Accordingly, there is a need for anti-hNKG2D mAbs with optimal properties for therapeutic use in inflammatory and/or autoimmune diseases and disorders. The present invention addresses these and other needs and provides several additional benefits that will be described in the remainder of this document.

SUMMARY OF THE INVENTION

The present invention provides isolated anti-hNKG2D monoclonal antibodies useful for therapeutic applications in humans. Typically, the antibodies are fully human or humanized to minimize the risk for immune responses against the antibodies when administered to a patient. As described herein, other antigen-binding molecules such as, e.g., antigen-binding antibody fragments, antibody derivatives, and multi-specific molecules, can be designed or derived from such antibodies.

In one aspect, the antibodies are characterized by one or more functional properties, or by a combination of functional properties. Exemplary properties include, e.g., preventing hNKG2D-mediated activation of hNKG2D-expressing NK or T cell; competing with at least one natural hNKG2D ligand, or with several ligands, in binding to hNKG2D; reducing the amount of hNKG2D on the surface of a hNKG2D-expressing NK or T cell; binding also cynomolgous and/or rhesus NKG2D; binding only one antibody molecule per hNKG2D dimer; cross-linking no more than 2 hNKG2D dimers when added to hNKG2D-expressing NK and/or T cells; having insignificant agonist effect on hNKG2D signaling upon binding; and/or binding to hNKG2D with a dissociation constant (KD) of 1 nM or less. Certain anti-hNKG2D antibodies of the invention may also or alternatively compete with, bind to essentially the same epitope as, or bind with the same or higher affinity as, one or more particular human anti-hNKG2D antibodies described herein, including antibodies MS and 21F2. For example, in one embodiment, the antibodies are also or alternatively more capable of competing with or blocking hNKG2D-binding of MS and/or 21F2 than known murine anti-hNKG2D antibodies (e.g., the ones described above). In one embodiment, the antibodies bind to the same hNKG2D epitope as MS and/or 21F2. In another embodiment, the antibodies also or alternatively bind the same epitope as MS. In another embodiment, the antibodies also or alternatively bind the same epitope as 21F2. The skilled person will understand that antibodies provided by and/or used in embodiments of this invention may exhibit three, four, or more of the above-referenced features.

In another aspect, the antibodies also or alternatively comprise one or more paratopes and/or antigen-binding sequences that are identical or similar to MS or 21F2 paratopes and/or antigen-binding sequences described herein.

In other aspects, the invention provides for nucleic acids encoding antibodies of the invention, expression vectors comprising such nucleic acids, host cells comprising such nucleic acids, host cells producing antibodies of the invention, and methods of producing anti-hNKG2D antibodies by culturing such host cells under appropriate conditions.

Antibody-binding fragments of such antibodies, as well as molecules comprising such antigen-binding fragments, including engineered antibody fragments, antibody derivatives, bispecific antibodies and other multispecific molecules, are also provided.

Pharmaceutical compositions and kits or other articles that comprise such antibodies or other molecules also are provided.

Further provided for are methods of reducing or inhibiting hNKG2D activation, hNKG2D-signaling, or activation of hNKG2D-expressing NK or T cells, methods or reducing inflammation, and methods of treating or preventing auto-immune and/or inflammatory diseases or disorders, including, but not limited to rheumatoid arthritis, inflammatory bowel disease (IBD) including Crohn's disease and ulcerative colitis, systemic erythromatosis lupus (SLE), psoriasis, psoriatic arthritis, multiple sclerosis, celiac disease, viral disease (such as, e.g., viral hepatitis), and transplant rejection of various organs and tissues (including, but not limited to, heart and bone marrow), using such antibodies, molecules, and compositions.

DESCRIPTION OF THE DRAWINGS

FIGS. 4A and 4B shows the amino acid sequences for the heavy (H) and light (L) chains of human anti-hNKG2D antibodies 16F16, and 16F31 (FIG. 4A), and MS and 21F2 (FIG. 4B) of IgG4 isotype, highlighting variable regions (bold) and CDR regions (underlined). The corresponding sequence identifiers for the amino acid sequences and the various highlighted portions are provided in Table 1.

FIGS. 5A-5H shows alignments of VH and VL sequences with the corresponding recombined germline sequences. CDR regions are indicated by bold Kabat numbers and somatic hypermutations are indicated by bold underlined text. (FIG. 5A) 16F16 IgG4 H chain; (FIG. 5B) 16F16 IgG4 L chain; (FIG. 5C) 16F31 IgG4 H chain; (FIG. 5D) 16F31 IgG4 L chain; (FIG. 5E) MS IgG4 H chain; (FIG. 5F) MS IgG4 L chain; (FIG. 5G) 21F2 IgG4 H chain; (FIG. 5H) 21F2 IgG4 L chain. SEQ ID NOS:27-30 correspond to recombined VH3_21/D3-9/JH4, VKI_L15/JK2, VH3_20/D3-10/JH6, and VKIII_A27/JK3, respectively, and SEQ ID NOS 60-63 correspond to recombined VH4_59//JH3, VKIII_A27/JK1, VH5_51/D3_10_R3/JH4, and VKIII_L6/JK1, respectively.

(FIG. 9A) 16F16: Pre-incubation with recombinantly expressed and purified 16F16 (0.3 µg; IgG4 isotype) prevented ON72 (0.3 µg) from binding to NKG2D. Reversing the incubation order showed that pre-incubation with ON72 (0.3 µg) only prevented 85% of the binding of recombinantly expressed and purified 16F16 of the IgG4 isotype (0.3 µg), showing that some fraction of NKG2D remained available for binding by the fully human antibody, suggesting an at least partially different epitope to the one bound by ON72. Antibody 149810 only demonstrated approximately 50% cross-inhibition of recombinantly expressed and purified 16F16 (IgG4 isotype), when tested at 1:1 (0.3 µg, 0.3 µg) and at 3:1 (1 µg, 0.3 µg) of antibody concentration, 149810 to 16F16, respectively, again likely showing differences in the binding epitope on NKG2D. The following incubation and detection combinations were used: detection of ON72 without (a) or with (b) 16F16 pre-incubation; detection of 16F16 without (c) or with (d) ON72 pre-incubation; detection of 149810 (0.3 µg) without (e) or with (f) 16F16 preincubation (0.3 µg); detection of 16F16 without (g) or with (h) 149810 pre-incubation (0.3 µg); detection of 149810 (1 µg) without (i) or with (j) 16F16 pre-incubation (0.3 µg); detection of 16F16 (0.3 µg) without (k) or with (I) 149810 pre-incubation (1 µg); 16F16 detection (0.3 µg). (FIG. 9B) MS: 0.1 µg murine anti-hNKG2D antibody was incubated with or without preincubation with 0.1 µg of MS antibody, followed by detection with anti-mouse antibody using flow cytometry. Incubation with 0.1 µg ON72, 1D11, or 149810 without pre-incubation with MS was normalized to 100%, and is shown in (a), (c), and (e), respectively. Incubation with 0.1 µg MS for 30 minutes followed by incubation and detection of ON72, 1D11, or 149810 is shown in (b), (d), and (f), respectively. Pre-incubation with MS inhibited 98%, 88%, and 96.5% of the NKG2D-binding of ON72, 1D11, and 149810, respectively, suggesting similar epitopes of at least some of the antibodies. (FIG. 9C) 21F2: detection of ON72 binding with (a) or without (b) pre-incubation with 21F2; detection of 1D11 binding with (c) or without (d) pre-incubation with 21F2; and detection of 149810 binding with (e) or without (f) 21F2 (all antibodies at 0.1 µg).

FIGS. 10A-10D shows staining of rhesus or cynomologous (cyno) cells with ON72 and 16F16 antibody purified from original hybridoma. (FIG. 10A) cyno NK cells, (FIG. 10B) cyno CD8+ T cells, (FIG. 10C) rhesus NK cells, and (FIG. 10D) rhesus CD8+ T cells. The values presented are mean fluorescent intensity (MFI) of binding where the MFI of binding of secondary antibody alone has been subtracted. No binding to CD4+ T cells was observed in either species.

FIGS. 11A-11B shows the binding of human antibody MS to human or cynomolgous CD8-positive cells in perifieral blood mononuclear cells (PBMCs) at different antibody concentrations, demonstrating that the affinity to human and cynomologous NKG2D is similar.

(FIG. 14A) inhibition of NK-92 cells killing of ULBP3-BaF/3 cells by MS or 21F2. (FIG. 14B) inhibition of NKL cells killing BaF/3-MICA cells by MS or 16F16.

(FIG. 19A) [CD3]=0.1 ng/ml; (FIG. 19B) [CD3]=0.3 ng/ml. T cell proliferation was assessed by CFSE dilution in a PBMC population stimulated with immobilized antibody as indicated for 3 days followed by IL-2 stimulation for four days. CD28 stimulation is included as a positive control of co-stimulation. No significant agonistic effect could be detected for MS, whereas ON72 had a low but significant effect on T cell proliferation.

(FIG. 20A), (FIG. 20B) Superpositioning of the hNKG2D/MS Fab and hNKG2D/MICA crystal complex structures (Li et al, Nat Immunol 2001; 2:443-451; PDB-code 1HYR, using the C-alpha-atoms of the common hNKG2D molecule as template). As both MICA and MS bind to the NKG2D dimer in an asymmetric manner, (FIG. 20A) and (FIG. 20B) show the two possible relative binding orientations of the two ligand molecules when bound to the NKG2D-dimer. There was a considerable overlap between the MICA and the MS Fab in superimposition calculations to hNKG2D for both orientations, demonstrating the ability of the MS Fab to block MICA from binding to the hNKG2D receptor. See Example 11. (FIG. 20C) Superpositioning of the hNKG2D/hzON72 Fab and the hNKG2D/MICA complex crystal structures. Each monomer of hNKG2D was bound by an hzON72 Fab. In a superimposition calculation to hNKG2D, also the hzON72 antibody made a considerable overlap to the MICA binding site, showing that hzON72 can block MICA binding to hNKG2D. See Example 12.

FIGS. 21A, 21B and 21C shows the epitope residues in the sequence (SEQ ID NO:2) of each NKG2D monomer unit of a hNKG2D dimer for MS Fab (FIG. 21A), hzON72 Fab (FIG. 21B) and a MICA molecule (FIG. 21C) in the sequences (SEQ ID NO:2) of the two hNKG2D monomer units. NKG2D residues within 4.0 Å distance from the crystal structure ligand atoms were considered to be part of the binding epitope and are underlined. Doubly underlined residues were involved in hydrogen-binding to the ligand. (FIG. 21A) Binding epitope for a single MS Fab on hNKG2D monomer units 1 and 2 in a hNKG2D dimer. Crystallographic monomers N and C were combined in the NKG2D monomer unit 1, and crystallographic monomers M and D were combined in the NKG2D monomer unit 2. In monomer unit 2, the Lys 150 side chain atom Nζ was only involved in hydrogen-binding in one of the two crystallographically independent complexes. See also Tables 9-12. (FIG. 21B) Respective binding epitopes for 2 hzON72 Fabs simultaneously bound to hNKG2D monomer units 1 and 2. Trp 166 was involved in hydrogen-bonding in one of the crystallographically independent molecular complexes (one hzON72 Fab molecule in complex with one hNKG2D monomer) but the distance was too far for hydrogen-binding in the other. See Tables 14-15. (FIG. 21C) Binding epitope for a MICA molecule on hNKG2D monomer units 1 and 2. MICA showed an asymmetric binding to the hNKG2D dimer, and could therefore bind in two orientations relative to MS-Fab. The second orientation of MICA can be obtained simply by the interchange of the 2 monomer unit representations.

DEFINITIONS

Figure 1A:
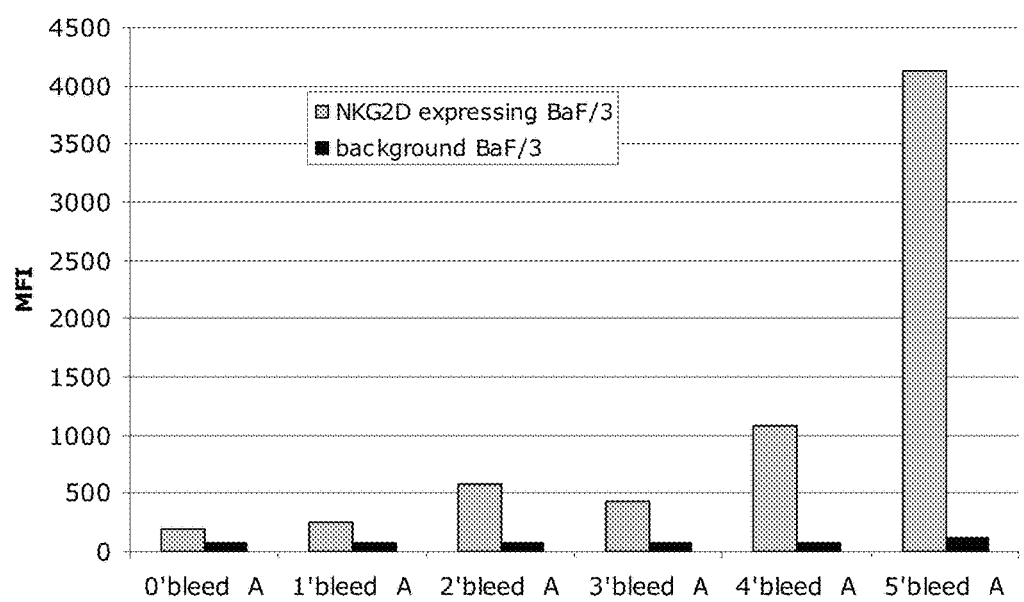
FIGS. 1A and 1B shows analyses of exemplary sera from hNKG2D-immunized mice from the KM Mouse™ strain. Flow cytometry analysis on NKG2D-expressing BAF/3 cells or control cells (BAF/3 cells) at various time points revealed increasing titers of antibody with NKG2D-selective binding in 1 µl of serum (FIG. 1A). Pre-incubation with sera (1 µl) taken after the 6$^{th}$ immunization contained antibody capable of preventing MICA-Fc-binding to NKG2D (FIG. 1B).

As used herein, "hNKG2D" and, unless otherwise stated or contradicted by context, the terms "NKG2D," also known as "NKG2-D," "CD314," "D12S2489E," "KLRK1," "killer cell lectin-like receptor subfamily K, member 1," and "KLRK1," refer to a human killer cell activating receptor gene, its mRNA (e.g., NCBI RefSeq NM_007360; SEQ ID NO:1), and its gene product (NCBI RefSeq NP_031386; SEQ ID NO:2), or naturally occurring variants thereof. In NK and T cells, the ligand-binding form of the hNKG2D receptor is a homodimer (Li et al., Nat Immunol 2001; 2:443-451). The hNKG2D receptor is typically presented at the surface in complex with DAP10 (Wu et al, J Exp Med 2000; 192:1059 et seq.; NCBI Accession No. AAG29425, AAD50293) and has been suggested to also form higher order complexes. Any activity attributed herein to hNKG2D, e.g., cell activation, antibody recognition, etc., can also be attributed to hNKG2D in the form of a complex or higher-order complexes with DAP10, and/or other components.

The term "antibody" herein is used in the broadest sense and specifically includes full-length monoclonal antibodies, polyclonal antibodies, and, unless otherwise stated or contradicted by context, antigen-binding fragments, antibody variants, and multispecific molecules thereof, so long as they exhibit the desired biological activity. Generally, a full-length antibody is a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarily determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. General principles of antibody molecule structure and various techniques relevant to the production of antibodies are provided in, e.g., Harlow and Lane, ANTIBODIES: A LABORATORY MANUAL, Cold Spring Harbor Laboratory Press, Cold Spring Harbor, N.Y., (1988).

An "antigen-binding fragment" of an antibody is a molecule that comprises a portion of a full-length antibody which is capable of detectably binding to the antigen, typically comprising one or more portions of at least the VH region. Antigen-binding fragments include multivalent molecules comprising one, two, three, or more antigen-binding portions of an antibody, and single-chain constructs wherein the VL and VH regions, or selected portions thereof, are joined by synthetic linkers or by recombinant methods to form a functional, antigen-binding molecule. While some antigen-binding fragments of an antibody can be obtained by actual fragmentation of a larger antibody molecule (e.g., enzymatic cleavage), most are typically produced by recombinant techniques.

The terms "antibody derivative" and "immunoconjugate" are used interchangeably herein to denote molecules comprising a full-length antibody or an antigen-binding fragment thereof, wherein one or more amino acids are chemically modified, e.g., by alkylation, PEGylation, acylation, ester formation or amide formation or the like, e.g., for linking the antibody to a second molecule. Exemplary modifications include PEGylation (e.g., cysteine-PEGylation), biotinylation, radiolabelling, and conjugation with a second agent (such as a cytotoxic agent), A "multispecific molecule" comprises an antibody, or an antigen-binding fragment thereof, which is associated with or linked to at least one other functional molecule (e.g. another peptide or protein such as another antibody or ligand for a receptor) thereby forming a molecule that binds to at least two different binding sites or target molecules. Exemplary multispecific molecules include bi-specific antibodies and antibodies linked to soluble receptor fragments or ligands.

The term "human antibody", as used herein, is intended to include antibodies having variable regions in which both the framework and CDR regions are derived from (i.e., are identical or essentially identical to) human germline immunoglobulin sequences. Furthermore, if the antibody contains a constant region, the constant region also is "derived from" human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750, 325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

The term "hypervariable region" when used herein refers to the amino acid residues of an antibody that are responsible for antigen binding. The hypervariable region generally comprises amino acid residues from a "complementarity-determining region" or "CDR" (residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Framework region" or "FR" residues are those VH or VL residues other than the CDRs as herein defined.

An "epitope" or "binding site" is an area or region on an antigen to which an antigen-binding peptide (such as an antibody) specifically binds. A protein epitope may comprise amino acid residues directly involved in the binding (also called the immunodominant component of the epitope) and other amino acid residues, which are not directly involved in the binding, such as amino acid residues which are effectively blocked by the specifically antigen binding peptide (in other words, the amino acid residue is within the "solvent-excluded surface" and/or "footprint" of the specifically antigen binding peptide). The term epitope herein includes both types of amino acid binding sites in any particular region of a hNKG2D that specifically binds to an anti-hNKG2D antibody, or another hNKG2D-specific agent according to the invention, unless otherwise stated (e.g., in some contexts the invention relates to antibodies that bind directly to particular amino acid residues). NKG2Ds may comprise a number of different epitopes, which may include, without limitation, (1) linear peptide antigenic determinants, (2) conformational antigenic determinants which consist of one or more noncontiguous amino acids located near each other in a mature NKG2D conformation; and (3) post-translational antigenic determinants which consist, either in whole or part, of molecular structures covalently attached to a NKG2D, such as carbohydrate groups. Unless otherwise specified or contradicted by context, conformational antigenic determinants comprise NKG2D amino acid residues within about 4 Å distance from an atom of an antigen-binding peptide.

The "solvent excluded surface" is the area of a molecule which, in a computer calculation, cannot be reached by any water molecule, e.g., because of binding of the molecule to a ligand (Lee and Richards, J Mol Biol 1971; 55:379-400, which is incorporated herein by reference).

The phrase "binds to essentially the same epitope or determinant as" an antibody of interest (e.g., MS or 21F2) means that an antibody "competes" with the antibody of interest for NKG2D molecules to which the antibody of interest specifically binds.

A "paratope" is an area or region of an antigen-binding portion of an antibody that specifically binds an antigen. Unless otherwise stated or clearly contradicted by context, a paratope may comprise amino acid residues directly involved in epitope binding, several of which are typically in CDRs, and other amino acid residues, which are not directly involved in the binding, such as amino acid residues which are effectively blocked by the specifically bound antigen (in other words, the amino acid residue is within the "solvent-excluded surface" and/or "footprint" of the specifically bound antigen).

The ability of an anti-NKG2D antibody to "block" the binding of a NKG2D molecule to a natural NKG2D-ligand (e.g., MICA), means that the antibody, in an assay using soluble or cell-surface associated NKG2D and ligand molecules, can detectably reduce the binding of a NKG2D-molecule to the ligand in a dose-dependent fashion, where the NKG2D molecule detectably binds to the ligand in the absence of the antibody. An exemplary assay for determining whether an anti-NKG2D antibody is capable of blocking MICA-binding is provided in Example 3. The same assay can be used for testing antibody-mediated blocking of other NKG2D ligands.

A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence and/or additions at one or both termini.

The term "substantially identical" in the context of two amino acid sequences means that the sequences, when optimally aligned, such as by the programs GAP or BESTFIT using default gap weights, share at least about 50 percent sequence identity. Typically sequences that are substantially identical will exhibit at least about 60, at least about 70, at least about 80, at least about 90, at least about 95, at least about 98, or at least about 99 percent sequence identity.

"Corresponding" amino acid positions in two substantially identical amino acid sequences are those aligned by any of the protein analysis software referred to herein.

A nucleic acid sequence (or element) is "operably linked" to another nucleic acid sequence (or element) when it is placed into a functional relationship with the other nucleic acid sequence. For example, DNA for a pre-sequence or secretory leader is operably linked to DNA for (i.e., coding for expression of) a polypeptide if it is expressed as a pre-protein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, some elements, such as enhancers, do not have to be contiguous with a coding sequence in order to be operably linked. Linking typically is accomplished by ligation at convenient restriction sites. If such sites do not exist, the synthetic oligonucleotide adaptors or linkers may be used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas clinical, curative, or palliative "treatment" of a patient in whom symptoms or clinically relevant manifestations of a disease or disorder have been identified generally does not constitute preventive or prophylactic therapy. Each form of treatment may be considered a distinct aspect of the invention.

DESCRIPTION OF THE INVENTION

The present invention is based, in part, on anti-NKG2D antibodies with properties suitable for treating human patients suffering from NKG2D-related conditions, such as, e.g., autoimmune and inflammatory diseases and disorders. Antibodies of the invention are typically either fully human or humanized in order to minimize the risk for an immune response against the antibody by the patient's own immune system, and bind to hNKG2D in its active form, i.e., a homodimer on the surface of a cell and associated with DAP10.

The antibodies of the invention are typically useful for treatment of conditions where NKG2D activity should be reduced. Such antibodies can reduce or inhibit activation of NKG2D-expressing NK and/or T cells by, e.g., competing with or blocking one or more endogenous NKG2D-ligands for binding to NKG2D, down-modulating or otherwise reducing the amount of cell-surface NKG2D upon binding, and/or eliciting an ADCC or CDC response against the cells.

In one aspect, antibodies of the invention are antagonists and compete with one or more natural ligands such as MICA for binding to human NKG2D, thereby reducing ligand-induced NKG2D-activation. MICA molecules have been clearly implicated in inflammatory diseases, and, as shown in Example 3, several human antibodies were effective at blocking MICA-binding to cell-surface NKG2D, particularly MS and 21F2, and epitope determination showed that MS Fab obstructed MICA from binding (Example 11, FIGS. 20A, 20B and 20C). Both MS and 21F2 were also highly efficient in blocking NK-cell mediated cytotoxicity (Example 6). Thus, these results demonstrate that the invention provides antibodies having such properties.

Figure 19A:
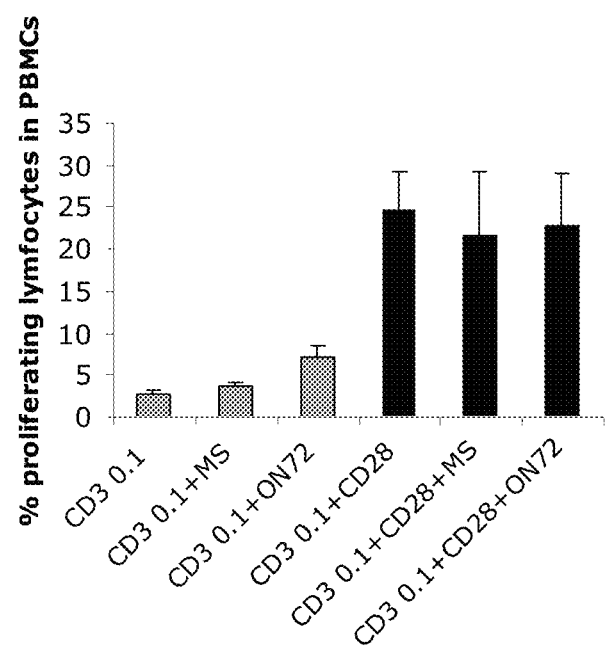
FIGS. 19A and 19B shows the results of an assay testing for an agonistic effect of immobilized MS and ON72 on T cell proliferation, using 2 different sub-optimal doses of CD3 to allow for co-stimulation.
Figure 19B:
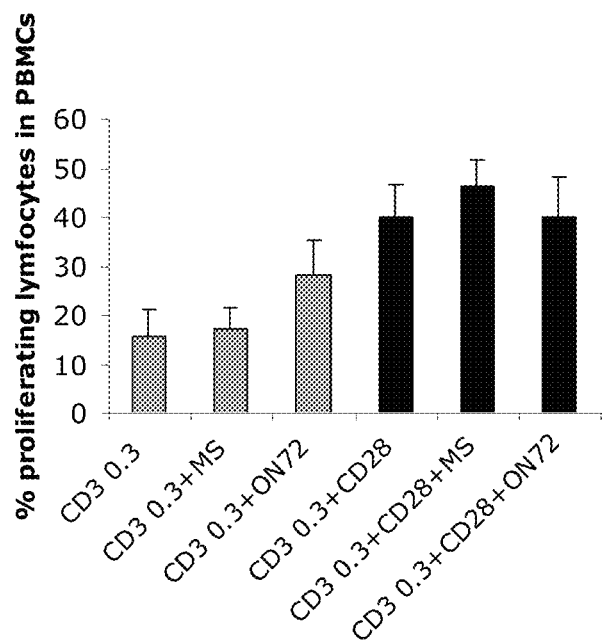

In a more particular aspect, antibodies of the invention are efficient antagonists, but also have insignificant agonistic effect on hNKG2D signaling, thus not contributing to NKG2D-driven inflammation. For example, as shown in FIGS. 19A and 19B, no costimulation of immobilized MS on CD3-triggered proliferation of PBMCs could be detected, whereas immobilized ON72 resulted in a small but significant co-stimulation. Without being limited to theory, this difference may at least in part be due to the differences in epitopes, shown in FIGS. 20A, 20B and 20C-22A, 22B, 22C and 22D. An antigen-binding portion of bivalent MS antibody binds strongly to one monomer in an hNKG2D dimer complex, but blocks binding of a second MS antibody (or a second antigen-binding portion of the same antibody) to the second monomer. By contrast, when an antigen-binding portion of a bivalent hzON72 antibody binds a first monomer in an hNKG2D dimer, it does not block the binding of a second hzON72 antibody (or a second antigen-binding portion of the same antibody) to the second monomer.

In one embodiment, the invention provides human or humanized anti-NKG2D antibodies which, when added to NKG2D-expressing NK or T cells, cross-link not more than 2 hNKG2D dimers. Preferably, such antibodies are bivalent. A bivalent antibody (such as, e.g., MS) for which the binding of the antigen-binding portion to an NKG2D monomer unit blocks further binding to the second NKG2D monomer unit can at most crosslink 2 hNKG2D dimers only. By contrast, a bivalent antibody which can bind an NKG2D monomer unit in an hNKG2D dimer without blocking binding to the second NKG2D monomer unit in an hNKG2D dimer can result in cross-linking of any number of hNKG2D dimers. Clustering of surface receptors commonly occurs in receptor activation.

In one embodiment, the invention provides human or humanized anti-NKG2D antibodies which, when added to NKG2D-expressing NK or T cells, binds strongly only to one monomer in an hNKG2D dimer complex. Without being limited to theory, strong binding to both monomers of the dimer can be a prerequisite for activation of the NKG2D-receptor. MICA and hzON72 bind strongly to both monomer units in an hNKG2D dimer. MS binding to hNKG2D dimer is, however, dominated by binding to one of the monomer units while binding to the second monomer unit is weak and unspecific, and with a smaller solvent-excluded surface area on the second hNKG2D monomer (Example 11). In separate and specific preferred embodiments, the ratio of the solvent-excluded surface areas from the first and second NKG2D monomer units by the binding of an antibody of the invention is more than about 1:1, at least about 2:1, or at least about 3:1.

In one embodiment, the invention provides human or humanized anti-NKG2D antibodies which bind essentially the same epitope as MS. Without being limited to theory, interactions of a ligand with particular residues, or residue combinations, on the hNKG2D dimer could avoid or minimize agonist activity. In separate and specific embodiments, the epitope of an antibody of the invention comprises at least one residue selected from, at least 3 residues selected from, at least 5 residues selected from, at least 8 residues selected from, at least 10 residues selected from, at least 12 residues selected from, or all of the residues selected from the group consisting of Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2).

In one aspect, the present invention provides a fully human antibody, or antigen-binding fragment thereof, that effectively prevents NKG2D-mediated cytotoxicity of a hNKG2D-expressing NK or T cell, competes with at least MICA in binding to hNKG2D; reduces the amount of cell-surface hNKG2D upon binding via, e.g., stimulating downmodulation of hNKG2D, internalization of hNKG2D and/or preventing reappearance of hNKG2D; has an affinity to hNKG2D of 10 nM or less, cross-reacts with cynomolgus and/or rhesus NKG2D; and is non-depleting, e.g., by having an IgG4 isotype. In a particular embodiment, the antibody is a non-depleting fully human antibody of the IgG4 isotype, with an affinity to hNKG2D of 1 nM or less, preferably 300 pM or less, which blocks at least 50%, at least 70%, or at least 90% of endogenous hNKG2D-ligand binding, and reduces the amount of cell-surface hNKG2D with at least 10%, at least 30%, or at least 50%. In another particular embodiment, the antibody is a bivalent non-depleting fully human antibody of the IgG4 isotype, with an affinity below 100 pM, which has an EC50 concentration below 0.01 ng/ml for blocking the binding of full saturation dose of MICA-Fc to cell-surface associated NKG2D, is capable of reducing the amount of cell-surface NKG2D with at least 75% upon binding, and, optionally, has an EC50 concentration for reducing a ligand-induced NK cell cytotoxicity that is lower than the EC50 concentration required for binding to cell-surface associated NKG2D. The antibody may further be capable of achieving, in an assay using NKG2D-expressing cells, its maximum level of hNKG2D down-modulation at a concentration lower than that required to obtain saturation of the hNKG2D receptors (i.e., saturation dose).

The production, characterization, and use of antibodies specifically binding hNKG2D and having some or all of these properties are described in more detail in the following sections, including the Examples.

Anti-NKG2D Antibodies

The antibodies of the invention are characterized by particular functional and/or structural features or properties. Assays to evaluate the functional activities of anti-hNKG2D antibodies are described in detail in the Examples, and structural properties such as, e.g., amino acid sequences, are described below.

Functional Properties

The antibodies of the invention bind to hNKG2D. In one embodiment, an antibody of the invention binds to hNKG2D with high affinity, for example with a KD of $10^{-7}$ M or less, a KD of $10^{-8}$ M or less, a KD of 1 nM or less, a KD of 0.3 nM or less, a KD of 0.2 nM or less, 0.1 nM or less, 0.05 nM or less, or 0.01 nM or less. In a particular embodiment, the antibody binds to hNKG2D with an affinity of 0.1 nM or less.

In one aspect, the invention provides antibodies also binding to one or more NKG2D orthologs in monkey such as cynomolgus monkey (*Macaca fascicularis*, NCBI accession No. AJ426429) and rhesus monkey (*Macaca mulatta*, NCBI accession No. AJ554302), and/or to hNKG2D homodimer, correctly folded monomeric full-length hNKG2D, hNKG2D fragment comprising an extracellular portion of hNKG2D, denatured hNKG2D, or to any combination of the preceding NKG2D forms. For example, as demonstrated in Example 5, the binding of human antibodies 21F2 and M5 to specific cynomolgus cell types were more than about 65% and about 75%, respectively, of their binding to the same human cell types, per the corresponding EC50 (i.e., the half maximal effective concentration) values. Accordingly, in one embodiment, an antibody of the invention binds to cynomolgus and/or rhesus NKG2D with similar affinity or efficacy as it binds to hNKG2D. For example, an antibody can bind to NKG2D-expressing cynomolgus or rhesus NK or T cells with an EC50 of about 50% or more, about 65% or more, or about 75% or more, of the corresponding EC50 for a corresponding population of NKG2D-expressing human NK or T cells. Additionally or alternatively, an antibody can bind to cynomolgus or rhesus NKG2D with an affinity of about 30% or more, about 50% or more, about 65% or more, or about 75% or more, about 80% or more, about 85% or more, or about 90% or more, of the affinity for hNKG2D. Such antibodies have the advantage of allowing for toxicity testing in the most suitable animal model (or models) prior to use in humans.

In one particular aspect, antibodies of the invention also bind a form of NKG2D that known murine anti-hNKG2D antibodies such as ON72 do not bind. Specifically, as described in Example 3, pre-incubation with ON72 only blocked about 82% of subsequently added human 16F16 antibody from binding to hNKG2D, while pre-incubation with 16F16 blocked about 95% of subsequently added ON72 from binding to hNKG2D.

Furthermore, the antibodies of the invention can reduce or inhibit hNKG2D-mediated activation of NK or T cells, i.e., antagonize the hNKG2D receptor. This may be tested in, e.g., one or more cytotoxicity assays described herein or known in the art. For example, an antibody inhibits hNKG2D-mediated activation of an NK or T cell if it inhibits the NK- or T cell-mediated killing of an NKG2D-ligand-expressing target cell by at least 10%, more preferably by at least 30%, even more preferably by at least 40%, at least 50%, at least 60%, at least 70%, at least 80% or at least 90%, as compared to target cell killing in the absence of any anti-hNKG2D antibody or in the presence of a non-specific, control antibody.

Antibodies of the invention that are hNKG2D antagonists can have no or low agonist activity. Preferably, such antibodies are human or humanized. Agonist activity may be tested in one of the assay described herein, or an assay known in the art. For example, one type of assay is a co-stimulation assay measuring proliferation of peripheral blood lymphocytes (PBMCs) stimulated with low levels of CD3 in the presence or absence of immobilized anti-NKG2D antibody (see Example 10). In such an assay, proliferation in the presence of an antibody of the invention is not more than 30%, not more than 20%, not more than 10%, not more than 5% or not significantly higher than in the absence of antibody. Preferably, proliferation in the presence of an antibody of the invention is not significantly higher than in the absence of antibody. In an additional or alternative embodiment, hNKG2D agonist activity of an antibody of the invention in an agonist assay is not more than 30%, not more than 20%, not more than 10%, not more than 5%, or not significantly higher than a control value. The control is preferably a negative control, such as, e.g., in the absence of antibody, in the absence of cell or another reagent, and/or in the presence of an irrelevant antibody. Preferably, agonist activity of an antibody of the invention is not significantly higher than a control value.

In another aspect, the invention provides antibodies that have a lower, preferably substantially lower, EC50 concentration for blocking ligand-induced cytotoxicity than for binding to cell-surface NKG2D of an NK or T cell. For example, for ON72, the EC50 concentration for binding to cell-surface NKG2D expressed on BaF/3 cells (0.062 µg/ml) was similar to the EC50 concentration for blocking NK-cell mediated killing of ligand- (ULBP3-) expressing target cells (0.065 µg/ml), whereas 21F2 had a lower, and MS a substantially lower, EC50 for blocking cytotoxicity (21F2: 0.021 µg/ml; MS: 0.012 µg/ml) than for binding to cell-surface NKG2D (21F2: 0.033 µg/ml; MS: 0.032 g/ml) (see Examples 6 and 9). Further, MS achieved maximum blocking of cytotoxicity at lower concentrations (a concentration corresponding only to about 80% saturation of cell-associated NKG2D-receptors, FIG. 3) than 21F2 and 16F16 (which had concentrations corresponding to saturating concentrations or higher, FIG. 3). Thus, in one embodiment, the invention provides antibodies, preferably human or humanized antibodies, that have a lower EC50 concentration for blocking ligand-induced cytotoxicity than for binding to cell-surface NKG2D of an NK or T cell. The EC50 for blocking cytotoxicity of NK or T cells of a cell line or other suitable preparation can be, e.g., about 95% or less, about 90% or less, about 85% or less, about 80% or less, about 70% or less, about 50% or less, or about 40% or less, of the EC50 for binding to cell-surface NKG2D of the same cell line or preparation. Exemplary cell lines for testing include NK-92 and NKL cells.

In another embodiment, the invention provides antibodies that achieve maximum blockage of NK cell cytotoxicity at a concentration lower than the concentration required to saturate the available hNKG2D-receptors. In a specific embodiment, the antibodies also compete with MS in binding to hNKG2D. In another specific embodiment, such antibodies bind to essentially the same hNKG2D epitope as MS.

The antibodies may reduce or inhibit NKG2D-mediated activation by, e.g., interfering with the hNKG2D-binding of one or more endogenous hNKG2D-ligands. For example, the antibodies may reduce or inhibit the hNKG2D-binding of MICA; MICB; ULBP1; ULBP2; ULBP4; and/or RAET1-family member; e.g., by reducing or inhibiting the hNKG2D-binding of MICA; or of MICA and MICB; or of MICA and ULBP3; or of MICA, MICB, and ULBP3; or of MICA, MICB, and all ULBP1, -2, -3, and 4; or of MICA, MICB, and one or more RAET1 family members. The ability of an antibody to inhibit hNKG2D-binding of endogenous NKG2D-ligands can be evaluated using binding or competition assays described herein. In one embodiment, antibodies of the invention are capable of inhibiting at least 30% of ligand binding, or at least 50% of ligand binding, or at least 70% of ligand binding, or at least 80%, or at least 90% of ligand binding. In another embodiment, the IC50 for an antibody of the invention to inhibit the hNKG2D-binding of 1 µg MICA-mFc is 1 nM or less, 0.5 nM or less, 0.2 nM or less, 0.1 nM or less, 0.05 nM or less, or 0.02 nM or less, 0.01 nM or less, 0.005 or less, or 0.002 or less. In another embodiment, full blockage of 1 µg MICA-mFc binding is achieved at an antibody concentration of 5 nM or less, 1 nM or less, 0.7 nM or less, 0.5 nM or less, or 0.2 nM or less, 0.1 nM or less, 0.05 nM or less, or about 0.02 nM or less. In one embodiment, the invention provides antibodies, especially human antibodies, that are as efficient or more efficient in reducing or inhibiting ligand hNKG2D-binding, such as, e.g., MICA binding to hNKG2D, than any of ON72, BAT221, 5C6, 1D11, ECM217, and 149810.

Figure 15:
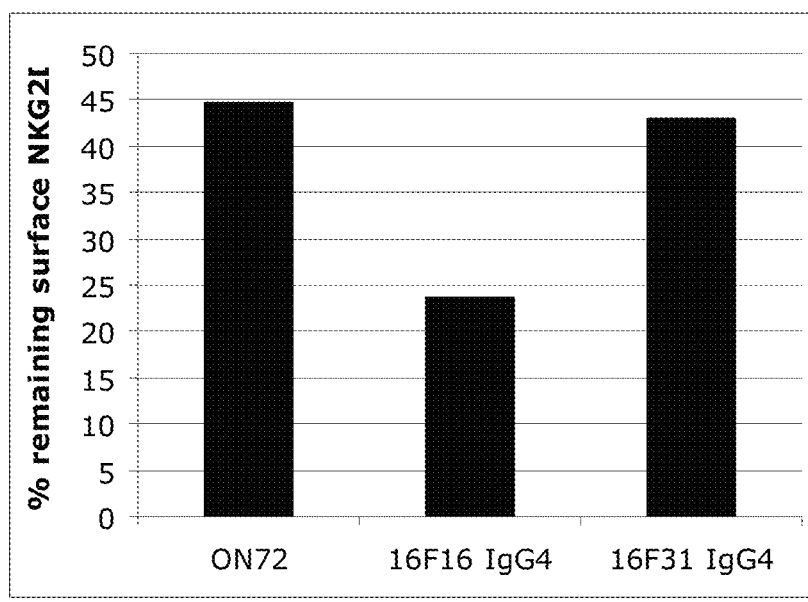
FIG. 15 shows antibody-induced reduction of cell-surface NKG2D, using BaF/3 cells transfected with NKG2D and DAP10. The figure shows the percentage of NKG2D receptor that remained on the surface of the cells after overnight incubation with ON72 (1 µg) or recombinantly expressed and purified human antibodies 16F16 (1 µg; IgG4 isotype) or 16F31 (3 µg; IgG4 isotype), as compared to control (cell surface NKG2D receptor after overnight incubation without anti-NKG2D antibody=100%).
Figure 16A:
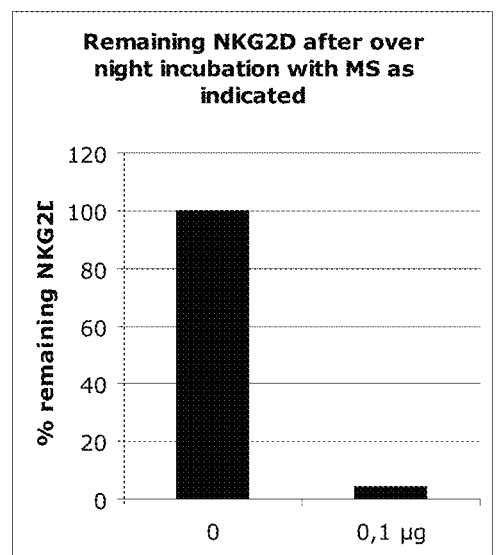
FIGS. 16A and 16B shows MS antibody-induced reduction of cell-surface NKG2D, using BaF/3 cells transfected with NKG2D and DAP10 (performed as for FIG. 15) (FIG. 16A), or freshly prepared human NK cells from peripheral blood (FIG. 16B). In (FIG. 16B), the human NK cells were incubated overnight in the presence of human serum, to mimic a situation in blood with IgGs present, and varying concentrations of MS antibody. Maximum downmodulation was achieved even at the lowest concentration, corresponding to about 60% receptor saturation measured in binding assay under similar conditions on NKG2D+ NK cells.
Figure 16B:
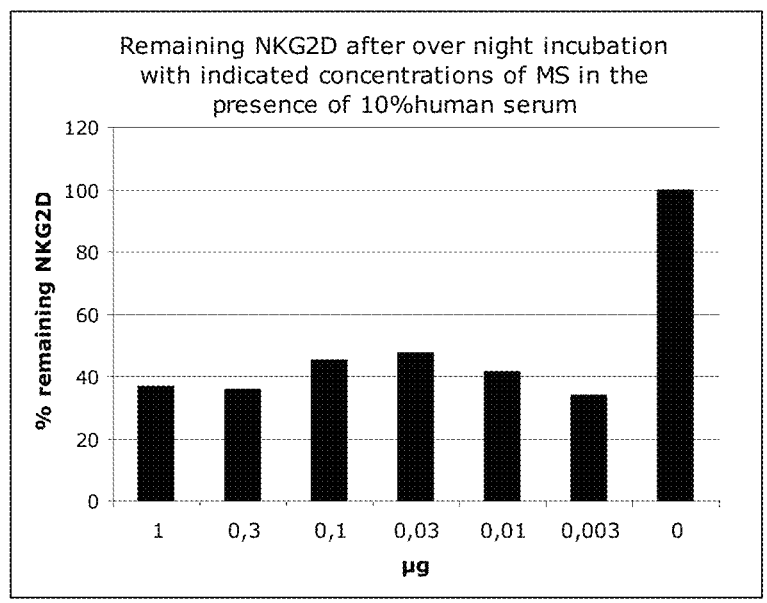
Figure 17:
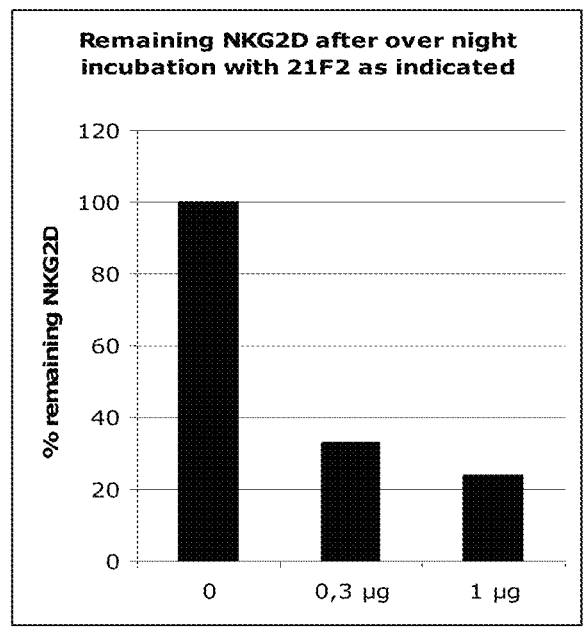
FIG. 17 shows the percentage reduction of cell-surface NKG2D on human NK cells after over-night incubation with indicated 21F2 antibody concentrations.

Additionally or alternatively, an anti-hNKG2D antibody of the invention can be capable of reducing the amount of cell-surface hNKG2D upon (i.e., following) binding. Reduction of cell-surface associated hNKG2D upon binding of an antibody can be an advantageous feature, since it reduces the number of hNKG2D receptors available for ligand binding and subsequent activation. Without being limited to theory, this reduction may be caused by NKG2D down-modulation, internalization, or other mechanism. As shown herein, anti-hNKG2D antibodies having a human Fc-region, such as human antibodies, are capable of effectively reducing the amount of cell-surface hNKG2D. For example, human anti-hNKG2D antibodies 16F16, MS, and 21F2 all reduced the amount of cell-surface hNKG2D with about 75% or more after overnight incubation in the absence of serum, with MS being the most effective, achieving 75-90% downmodulation at a low concentration (FIGS. 15-17). Also, in the presence of serum, an MS concentration corresponding to less than saturating concentration on hNKG2D-expressing BaF/3 cells achieved maximum downmodulation (FIG. 16B). Accordingly, in one embodiment, the invention provides antibodies binding to hNKG2D that are able to achieve maximum down-modulation of hNKG2D at less than saturating concentrations. In another embodiment, such antibodies also compete with MS in binding to hNKG2D. In another embodiment, such antibodies also bind to essentially the same hNKG2D epitope as MS. An antibody of the invention can be capable of reducing cell surface hNKG2D by at least 10%, at least 20%, at least 30%, at least 50%, at least 70%, or at least 90% as compared to cell-surface hNKG2D in the absence of anti-hNKG2D antibody or in the presence of a non-specific control antibody. Preferably, the antibodies achieve reduction of cell-surface NKG2D while causing no or minimal activation of NKG2D-receptor signalling, i.e., with no or minimal agonist activity. Exemplary assays for evaluating cell surface hNKG2D and agonistic activity of anti-hNKG2D antibodies are described herein. In one embodiment, the invention provides antibodies, particularly human antibodies, which are capable of a higher degree of down-modulation than a control antibody selected from ON72, BAT221, 5C6, 1D11, ECM217, and 149810. In another embodiment, an anti-hNKG2D antibody of the invention can be capable of achieving maximum down-modulation of cell-surface NKG2D expressed by a cell or cell-line at a concentration lower than a saturating concentration.

In another embodiment, the invention provides antibodies that compete with and/or bind to the same epitope on hNKG2D as 16F16, 16F31, MS, and/or 21F2, more preferably MS and/or 21F2. Such antibodies can be identified based on their ability to cross-compete with 16F16, 16F31, MS, or 21F2 in standard hNKG2D binding assays as described herein. The ability of a test antibody to inhibit the binding of 16F16, 16F31, MS, or 21F2 to hNKG2D demonstrates that the test antibody can compete with 16F16, 16F31, MS, or 21F2 for binding to hNKG2D and thus can bind to the same epitope on hNKG2D as 16F16, 16F31, MS, or 21F2. In a preferred embodiment, the antibody that binds to the same epitope on hNKG2D as 16F16, 16F31, MS or 21F2 is a human monoclonal antibody. Such human monoclonal antibodies can be prepared and isolated as described in the Examples.

In another preferred embodiment, the antibody binds to a different epitope than any of the mouse monoclonal antibodies ON72, BAT221, 5C6, 1D11, ECM217, and 149810, and cross-competes more with 16F16, 16F31, MS, or 21F2 than with either of the listed mouse monoclonal antibodies.

In one embodiment, the epitope of an antibody of the invention comprises one or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2). In one embodiment, the epitope of an antibody of the invention comprises 5 or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2). In one embodiment, the epitope of an antibody of the invention comprises 8, 10, 12 or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2). In one embodiment, the epitope of an antibody of the invention comprises the residues Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2). In one embodiment, the epitope of an antibody of the invention consists essentially of the residues Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2). In one embodiment, the epitope of an antibody of the invention consists of one or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2). In one embodiment, the epitope of an antibody of the invention consists of the residues Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of hNKG2D (SEQ ID NO: 2).

In one embodiment, the epitope of an antibody of the invention comprises one or more residues involved in hydrogen-binding selected from Lys 150, Ser 151, Tyr 152, Ile 181, Met 184, Gln 185, Lys 197, Thr 205, and Asn 207 of hNKG2D (SEQ ID NO: 2). In one embodiment, the epitope of an antibody of the invention comprises 5 or more residues involved in hydrogen-binding selected from Lys 150, Ser 151, Tyr 152, Ile 181, Met 184, Gln 185, Lys 197, Thr 205, and Asn 207 of hNKG2D (SEQ ID NO: 2). In one embodiment, the epitope of an antibody of the invention comprises Lys 150, Ser 151, Tyr 152, Ile 181, Met 184, Gln 185, Lys 197, Thr 205, and Asn 207 of hNKG2D (SEQ ID NO: 2).

Preferred antibodies of the invention exhibit at least one, more preferably two, three, four, five or more of the following properties: (a) prevents NKG2D-mediated activation of an NKG2D-expressing NK or T cell, optionally with an EC50 for reducing ligand-induced cytotoxicity lower than the EC50 for binding to the cell; (b) competes with at least one NKG2D ligand in binding to NKG2D, preferably with at least MICA and ULBP3; (c) reduces the amount of NKG2D on the surface of a NKG2D-expressing NK or T cell, preferably with at least 75%; (d) binds to cynomolgus and/or rhesus NKG2D, preferably with no less than 50% of the affinity by which it binds to hNKG2D; (e) binds to more than one form or conformation of NKG2D; (f) binds to NKG2D with a Kd of 1 nM or less, preferably 0.1 nM or less; (g) competes with one or more of 16F16, 16F31, MS, or 21F2 in binding to hNKG2D, (h) competes more with 16F16, 16F31, MS, or 21F2 than with any of ON72, BAT221, 5C6, 1D11, ECM217, and 149810 in binding to hNKG2D; (i) blocks more than 90% of 16F16, MS, or 21F2 binding to cell-surface hNKG2D; (j) has insignificant agonist activity, and (k) binds to essentially the same epitope as any of 16F16, 16F31, MS and/or 21F2, preferably essentially the same epitope as MS and/or 21F2. Any combination of the above-described functional features, and/or the functional features as described in the Examples, may be exhibited by an antibody of the invention.

Structural Properties

Preferred antibodies of the invention are the human monoclonal antibodies 16F16, 16F31, MS, and 21F2 produced, isolated, and structurally and functionally characterized as described in the Examples. Full-length, variable, and CDR sequences of these antibodies are set forth in Table 1.

TABLE 1

Full-length, variable, and CDR amino acid sequences for 16F16, 16F31, MS, and 21F2

| Antibody portion | SEQ ID NO: |
| --- | --- |
| 16F16 IgG4 H chain | 7 |
| 16F16 L chain | 8 |
| 16F31 IgG4 H chain | 9 |
| 16F16 L chain | 10 |
| 16F16 VH region | 11 |
| 16F16 VL region | 12 |
| 16F31 VH region | 13 |
| 16F31 VL region | 14 |
| 16F16 VH CDR1 | 15 |
| 16F16 VH CDR2 | 16 |
| 16F16 VH CDR3 | 17 |
| 16F16 VL CDR1 | 18 |
| 16F16 VL CDR2 | 19 |
| 16F16 VL CDR3 | 20 |
| 16F31 VH CDR1 | 21 |
| 16F31 VH CDR2 | 22 |
| 16F31 VH CDR3 | 23 |
| 16F31 VL CDR1 | 24 |
| 16F31 VL CDR2 | 25 |
| 16F31 VL CDR3 | 26 |
| MS IgG4 H chain | 40 |
| MS L chain | 41 |
| 21F2 IgG4 H chain | 42 |
| 21F2 L chain | 43 |
| MS VH region | 44 |
| MS VL region | 45 |
| 21F2 VH region | 46 |
| 21F2 VL region | 47 |
| MS VH CDR1 | 48 |
| MS VH CDR2 | 49 |
| MS VH CDR3 | 50 |
| MS VL CDR1 | 51 |
| MS VL CDR2 | 52 |
| MS VL CDR3 | 53 |
| 21F2 VH CDR1 | 54 |
| 21F2 VH CDR2 | 55 |
| 21F2 VH CDR3 | 56 |
| 21F2 VL CDR1 | 57 |
| 21F2 VL CDR2 | 58 |
| 21F2 VL CDR3 | 59 |

Certain anti-NKG2D antibodies of the invention has the same or a similar paratope as MS. In one embodiment, the antibody has a paratope comprising residues corresponding to one or more of Tyr 33 and Trp 97 of the MS L chain (SEQ ID NO: 41), and/or to one or more of Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 40). In one embodiment, the antibody has a paratope comprising residues corresponding to Tyr 33 and Trp 97 of the MS L chain (SEQ ID NO: 41), and/or to 3, 5, 7, 10 or more of Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 40). In one embodiment, the antibody has a paratope comprising residues corresponding to Tyr 33 and Trp 97 of the MS L chain (SEQ ID NO: 41), and Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 40). In one embodiment, the antibody has a paratope consisting essentially of residues corresponding to Tyr 33 and Trp 97 of the MS L chain (SEQ ID NO: 41), and Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 40). In one embodiment, the antibody has a paratope consisting of residues corresponding to Tyr 33 and Trp 97 of the MS L chain (SEQ ID NO: 41), and Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 40).

Given that all of 16F16, 16F31, 21F2, and MS can bind to hNKG2D, it may be possible to "mix and match" the respective VH and VL sequences of these antibodies to create other anti-hNKG2D binding molecules of the invention. The hNKG2D-binding of such "mixed and matched" antibodies can be tested using the binding assays described herein (e.g. flow cytometry, Biacore, ELISAs) and/or using a cytotoxicity assay as described herein. Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence.

Accordingly, in one aspect, the invention provides an isolated monoclonal antibody, or antigen binding portion thereof, comprising: (a) a VH region comprising an amino acid sequence selected from the group consisting of SEQ ID NOS: 11, 13, 44, and 46, and (b) a VL region comprising an amino acid sequence selected from the group consisting of SEQ ID NOs: 12, 14, 45, and 47; wherein the antibody binds hNKG2D. Preferred heavy and light chain combinations include: (a) a VH region comprising the amino acid sequence of SEQ ID NO: 11; and (b) a light chain variable region comprising the amino acid sequence of SEQ ID NO: 12; (a) a heavy chain variable region comprising the amino acid sequence of SEQ ID NO: 13; and (b) a light chain variable region comprising the amino acid sequence of SEQ ID NO: 14; (a) a VH region comprising the amino acid sequence of SEQ ID NO: 44; and (b) a light chain variable region comprising the amino acid sequence of SEQ ID NO: 46; or (a) a heavy chain variable region comprising the amino acid sequence of SEQ ID NO: 45; and (b) a light chain variable region comprising the amino acid sequence of SEQ ID NO: 47.

In another aspect, the invention provides antibodies that comprise the heavy chain and light chain CDR1s, CDR2s and/or CDR3s of 16F16, 16F31, MS, or 21F2, or combinations thereof. The CDR regions are delineated using the Kabat system (Kabat et al. (1991) Sequences of Proteins of Immunological Interest, Fifth Edition, U.S. Department of Health and Human Services, NIH Publication No. 91-3242). See, e.g., FIGS. 4A and 4B and 5A-5H. Given that each of these antibodies can bind to hNKG2D and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody can contain a VH CDR1, 2 and 3 and a VL CDR1, 2 and 3) to create other anti-hNKG2D binding molecules of the invention. The hNKG2D-binding of such "mixed and matched" antibodies can be tested using the binding assays described above and in the Examples (e.g. flow cytometry, Biacore, or ELISAs). Preferably, when VH CDR sequences are mixed and matched, the CDR1, CDR2 and/or CDR3 sequence from a particular VH sequence is replaced with a structurally similar CDR sequence(s). Likewise, when VL CDR sequences are mixed and matched, the CDR1, CDR2 and/or CDR3 sequence from a particular VL sequence preferably is replaced with a structurally similar CDR sequence(s). For example, the VL CDR1s and CDR3s of 16F16, 16F31, MS, and 21F2 and the VL CDR2 sequences of MS and 21F2 share some structural similarity and therefore are amenable to mixing and matching. It will be readily apparent to the ordinarily skilled artisan that novel VH and VL sequences can be created by substituting one or more VH and/or VL CDR region sequences with structurally similar sequences from the CDR sequences disclosed herein for monoclonal antibodies antibodies 16F16, 16F31, MS, and 21F2.

Accordingly, in another aspect, the invention provides an isolated monoclonal antibody, or antigen binding portion thereof comprising: (a) a VH CDR1 comprising an amino acid sequence selected from the group consisting of SEQ ID NOs: 15, 21, 48, and 54; (b) a VH CDR2 comprising an amino acid sequence selected from the group consisting of SEQ ID NOs: 16, 22, 49, and 55; (c) a VH CDR3 comprising an amino acid sequence selected from the group consisting of SEQ ID NOs: 17, 23, 50, and 56; (d) a VL CDR1 comprising an amino acid sequence selected from the group consisting of SEQ ID NOs:18, 24, 51, and 57; (e) a VL CDR2 comprising an amino acid sequence selected from the group consisting of SEQ ID NOs:19, 25, 52, and 57; and (f) a VL CDR3 comprising an amino acid sequence selected from the group consisting of SEQ ID NOs: 20, 26, 53, and 59; wherein the antibody binds hNKG2D.

In a preferred embodiment, the antibody comprises: (a) a VH CDR1 comprising SEQ ID NO:15; (b) a VH CDR2 comprising SEQ ID NO:16; (c) a VH CDR3 comprising SEQ ID NO:17; (d) a VL CDR1 comprising SEQ ID NO:18; (e) a VL CDR2 comprising SEQ ID NO: 19; and (f) a VL CDR3 comprising SEQ ID NO: 20.

In another preferred embodiment, the antibody comprises: (a) a VH CDR1 comprising SEQ ID NO: 21; (b) a VH CDR2 comprising SEQ ID NO:22; (c) a VH CDR3 comprising SEQ ID NO:23; (d) a VL region CDR1 comprising SEQ ID NO:24; (e) a VL CDR2 comprising SEQ ID NO:25; and (f) a VL CDR3 comprising SEQ ID NO: 26.

In another preferred embodiment, the antibody comprises: (a) a VH CDR1 comprising SEQ ID NO: 48; (b) a VH CDR2 comprising SEQ ID NO:49; (c) a VH CDR3 comprising SEQ ID NO:50; (d) a VL region CDR1 comprising SEQ ID NO:51; (e) a VL CDR2 comprising SEQ ID NO:52; and (f) a VL CDR3 comprising SEQ ID NO: 53.

In another preferred embodiment, the antibody comprises: (a) a VH CDR1 comprising SEQ ID NO: 54; (b) a VH CDR2 comprising SEQ ID NO:55; (c) a VH CDR3 comprising SEQ ID NO:56; (d) a VL region CDR1 comprising SEQ ID NO:57; (e) a VL CDR2 comprising SEQ ID NO:58; and (f) a VL CDR3 comprising SEQ ID NO: 59.

In another preferred embodiment, the antibody comprises: (a) a VH CDR1 consisting of SEQ ID NO:15; (b) a VH CDR2 consisting of SEQ ID NO:16; (c) a VH CDR3 consisting of SEQ ID NO:17; (d) a VL CDR1 consisting of SEQ ID NO:18; (e) a VL CDR2 consisting of SEQ ID NO: 19; and (f) a VL CDR3 consisting of SEQ ID NO: 20.

In another preferred embodiment, the antibody comprises: (a) a VH CDR1 consisting of SEQ ID NO: 21; (b) a VH CDR2 consisting of SEQ ID NO:22; (c) a VH CDR3 consisting of SEQ ID NO:23; (d) a VL region CDR1 consisting of SEQ ID NO:24; (e) a VL CDR2 consisting of SEQ ID NO:25; and (f) a VL CDR3 consisting of SEQ ID NO: 26.

In another preferred embodiment, the antibody comprises: (a) a VH CDR1 consisting of SEQ ID NO: 48; (b) a VH CDR2 consisting of SEQ ID NO:49; (c) a VH CDR3 consisting of SEQ ID NO:50; (d) a VL region CDR1 consisting of SEQ ID NO:51; (e) a VL CDR2 consisting of SEQ ID NO:52; and (f) a VL CDR3 consisting of SEQ ID NO: 53.

In another preferred embodiment, the antibody comprises: (a) a VH CDR1 consisting of SEQ ID NO: 48; (b) a VH CDR2 consisting of SEQ ID NO:49; (c) a VH CDR3 consisting of SEQ ID NO:50; (d) a VL region CDR1 consisting of SEQ ID NO:51; (e) a VL CDR2 consisting of SEQ ID NO:52; and (f) a VL CDR3 consisting of SEQ ID NO: 53, and residues corresponding to one, two, or all of Gln 1, Asp 26, and Asp 27 in the MS H chain (SEQ ID NO: 40).

In another preferred embodiment, the antibody comprises: (a) a VH CDR1 consisting of SEQ ID NO: 54; (b) a VH CDR2 consisting of SEQ ID NO:55; (c) a VH CDR3 consisting of SEQ ID NO:56; (d) a VL region CDR1 consisting of SEQ ID NO:57; (e) a VL CDR2 consisting of SEQ ID NO:58; and (f) a VL CDR3 consisting of SEQ ID NO: 59.

In certain embodiments, an antibody of the invention comprises a VH region from a particular germline H chain immunoglobulin gene, or a combination of particular germline H chain immunoglobulin genes; and/or a VL region from a particular germline L chain immunoglobulin gene, or a combination of particular germline L chain immunoglobulin genes. Such combinations can be obtained, e.g., in vivo via somatic recombination in a B cell.

For example, in one embodiment, the invention provides an isolated anti-hNKG2D antibody, or an antigen-binding fragment thereof, wherein the antibody: (a) comprises a VH region from a human VH3_21, VH3_20, VH4_59, or VH5_51 gene recombined with a human D3-9, D3-10, or D3_10_R3 gene and a JH3, JH4 or JH6 gene, (b) comprises a VL region derived from a human VKI_L15 or VKIII_A27 or VKIII_L6 gene recombined with a human JK1, JK2 or JK3 gene, and (c) the antibody binds to hNKG2D.

In another embodiment, the invention provides an isolated anti-hNKG2D antibody, or an antigen-binding fragment thereof, comprising a VH region obtained by a recombination of human VH3_21, D3-9, and JH4 genes and a VL region obtained by a recombination of human VKI_L15 and JK2 genes.

In another embodiment, the invention provides an isolated anti-hNKG2D antibody, or an antigen-binding fragment thereof, comprising a VH region obtained by a recombination of human VH3_20, D3-10, and JH6 genes and a VL region obtained by a recombination of human VKIII_A27 and JK3 genes.

In another embodiment, the invention provides an isolated anti-hNKG2D antibody, or an antigen-binding fragment thereof, comprising a VH region obtained by a recombination of human VH4_59, a D gene, and JH3 genes and a VL region obtained by a recombination of human VKIII_A27 and JK1 genes.

In another embodiment, the invention provides an isolated anti-hNKG2D antibody, or an antigen-binding fragment thereof, comprising a VH region obtained by a recombination of human VH5_51, D3_10_R3, and JH4 genes and a VL region obtained by a recombination of human VKIII_L6 and JK1 genes.

In separate and specific embodiments, the invention provides isolated anti-NKG2D antibodies obtained by introducing one, two, three, four or more amino acid substitutions and/or somatic hypermutations in the VH and/or VL region of an anti-hNKG2D antibody described above.

As used herein, a human antibody comprises heavy or light chain variable regions "of" or "derived from" or that are "the product of" a particular germline sequence if the variable regions of the antibody are obtained from a system (as described below) that uses human germline immunoglobulin genes. Such "systems" include immunizing a transgenic mouse carrying human immunoglobulin genes with the antigen of interest or screening a human immunoglobulin gene library displayed on phage with the antigen of interest. A human antibody that is "of" or "derived from" or "the product of" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "of" or "derived from" or "the product of" a particular human germline immunoglobulin sequence may contain amino acid differences as compared to the germline sequence, due to, for example, naturally-occurring somatic mutations or intentional introduction of site-directed mutation(s) (which may be selected substitutions).

However, a human antibody is typically at least 90% identical in amino acid sequence to an amino acid sequence encoded by a recombed germline immunoglobulin sequence and can usually be identified as human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the recombed germline immunoglobulin gene.

Typically, a human antibody derived from a particular human germline sequence will display no more than 10 amino acid differences from the amino acid sequence encoded by the human germline immunoglobulin gene. In certain cases, the human antibody may display no more than 8, no more than 5, or even no more than 4, 3, 2, or 1 amino acid difference, or no amino acid difference, from the amino acid sequence encoded by the recombed germline immunoglobulin gene.

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-hNKG2D antibodies of the invention. For example, the invention provides an isolated antibody, or antigen binding portion thereof, comprising a heavy chain variable region and a light chain variable region, wherein: (a) the VH region comprises an amino acid sequence that is at least 80% identical to an amino acid sequence selected from the group consisting of SEQ ID NOs: 11, 13, 44, and 46; (b) the VL region comprises an amino acid sequence that is at least 80% identical to an amino acid sequence selected from the group consisting of SEQ ID NOs: 12, 14, 45, and 47; (c) the antibody binds to hNKG2D and exhibits at least one of the functional properties described herein, preferably several of the functional properties described herein.

In other embodiments, the VH and/or VL amino acid sequences may be 85%, 90%, 95%, 96%, 97%, 98% or 99% identical to the sequences set forth above. An antibody having VH and VL regions having high (i.e., 80% or greater) identity to the VH and VL regions of the sequences set forth above, can be obtained by mutagenesis (e.g., site-directed or PCR-mediated mutagenesis) of nucleic acid molecules encoding SEQ ID NOs:11-14 or 44-47, followed by testing of the encoded altered antibody for retained function (e.g., hNKG2D binding affinity, hNKG2D-ligand blocking, hNKG2D downmodulation, or reduction of NKG2D-mediated activation of an NK or T cell) using the functional assays described herein.

The percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm in sequence-analysis software. Protein analysis software matches similar sequences using measures of similarity assigned to various substitutions, deletions and other modifications, including conservative amino acid substitutions.

The percent identity between two amino acid sequences can be determined, e.g., using the Needleman and Wunsch (J. Mol. Biol. 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183: 63-98; Pearson, Methods Mol. Biol. 2000; 132:185-219).

The percent identity between two amino acid sequences can also be determined using the algorithm of E. Meyers and W. Miller (Comput. Appl. Biosci., 1988; 11-17) which has been incorporated into the ALIGN program (version 2.0), using a PAM120 weight residue table, a gap length penalty of 12 and a gap penalty of 4.

Another algorithm for comparing a sequence to a other sequences contained in a database is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. The protein sequences of the present invention can there be used as a "query sequence" to perform a search against public databases to, for example, identify related sequences. Such searches can be performed using the XBLAST program (version 2.0) of Altschul, et al. 1990 (supra). BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 (supra). When utilizing BLAST and Gapped BLAST programs, the default parameters of the respective programs (e.g., XBLAST and NBLAST) can be used. See http://www.ncbi.nlm.nih.gov.

In certain embodiments, an antibody of the invention comprises a VH region comprising CDR1, CDR2 and CDR3 sequences and a VL region comprising CDR1, CDR2 and CDR3 sequences, wherein one or more of these CDR sequences comprise specified amino acid sequences based on the preferred antibodies described herein; 16F16, 16F31, MS, or 21F2, wherein one or more CDRs optionally contains one or more conservative amino acid modifications, and wherein the antibodies retain the desired functional properties of the anti-hNKG2D antibodies of the invention. Accordingly, the invention provides an isolated antibody, or antigen-binding fragment thereof, comprising a heavy chain variable region comprising CDR1, CDR2, and CDR3 sequences and a light chain variable region comprising CDR1, CDR2, and CDR3 sequences, wherein: (a) the VH region CDR3 sequence comprises an amino acid sequence selected from the group consisting of amino acid sequences of SEQ ID NOs:17, 23, 50, and 56; (b) the VL region CDR3 sequence comprises an amino acid sequence selected from the group consisting of amino acid sequences of SEQ ID NOs: 20, 26, 53 and 59; (c) one or more CDRs optionally contains one or more conservative amino acid modifications, and (d) the antibody binds to hNKG2D and exhibits at least one of the functional properties described herein, more preferably several of the functional properties described herein.

In a further embodiment, the VH region CDR2 sequence comprises an amino acid sequence selected from the group consisting of amino acid sequences of SEQ ID NOs: 16, 22, 49, and 55; and the VL region CDR2 sequence comprises an amino acid sequence selected from the group consisting of amino acid sequences of SEQ ID NOs: 19, 25, 52, and 58, wherein one or more CDRs optionally contains one or more conservative amino acid modifications.

In a still further embodiment, the VH region CDR1 sequence comprises an amino acid sequence selected from the group consisting of amino acid sequences of SEQ ID NOs:15, 21, 48, and 54, and conservative modifications thereof; and the VL region CDR1 sequence comprises an amino acid sequence selected from the group consisting of amino acid sequences of SEQ ID NOs:18, 24, 51, and 57, wherein one or more CDRs optionally contains one or more conservative amino acid modifications.

As used herein, the term "conservative amino acid modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as, e.g., site-directed mutagenesis and PCR-mediated mutagenesis. An antibody sequence comprising amino acid modifications as compared to a parent antibody is typically at least 90%, preferably at least 95%, 98%, or 99% identical to the corresponding amino acid sequence in the parent and/or comprises at most 10, preferably at most 5, 4, 3, 2 amino acid modifications as compared to the parent antibody sequence.

"Conservative" amino acid substitutions are typically those in which an amino acid residue is replaced with an amino acid residue having a side chain with similar physicochemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function (i.e., the functions set forth in (c), (d) and (e) above) using the functional assays described herein.

Antigen-Binding Fragments

The anti-hNKG2D antibodies of the invention may be prepared as full-length antibodies or antigen-binding fragments thereof. Examples of antigen-binding fragments include Fab, Fab', F(ab)2, F(ab')2, F(ab)3, Fv (typically the VL and VH domains of a single arm of an antibody), single-chain Fv (scFv; see e.g., Bird et al., Science 1988; 242:423-426; and Huston et al. PNAS 1988; 85:5879-5883), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23:1126-1136; WO2005040219, and published U.S. Patent Applications 20050238646 and 20020161201.

Antibody fragments can be obtained using conventional recombinant or protein engineering techniques, and the fragments can be screened for antigen-binding or other function in the same manner as are intact antibodies.

Various techniques have been developed for the production of antibody fragments. Traditionally, these fragments were derived via proteolytic digestion of full-length antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. Alternatively, Fab'-SH fragments can be directly recovered from E. coli and chemically coupled to form F(ab')2 fragments (Carter et al., Bio/Technology, 10:163-167 (1992)). According to another approach, F(ab')2 fragments can be isolated directly from recombinant host cell culture. In other embodiments, the antibody of choice is a single-chain Fv fragment (scFv). See WO 1993/16185; U.S. Pat. Nos. 5,571, 894; and 5,587,458. The antibody fragment may also be a "linear antibody", e.g., as described in U.S. Pat. No. 5,641, 870, for example. Such linear antibody fragments may be monospecific or bispecific.

Multispecific Molecules

In another aspect, the present invention features multispecific molecules comprising an anti-hNKG2D antibody, or an antigen-fragment thereof, of the invention. Such multispecific molecules include bispecific molecules comprising at least one first binding specificity for hNKG2D and a second binding specificity for a second target epitope.

One type of bispecific molecules are bispecific antibodies. Bispecific antibodies are antibodies that have binding specificities for at least two different epitopes. Methods for making bispecific antibodies are known in the art, and traditional production of full-length bispecific antibodies is usually based on the coexpression of two immunoglobulin heavy-chain-light-chain pairs, where the two chains have different specificities (Millstein et al., Nature, 305: 537-539 (1983)). Bispecific antibodies can be prepared as full-length antibodies or antibody fragments (e.g. F(ab')2 bispecific antibodies) or any other antigen-binding fragments described herein.

In the bispecific antibodies according to the present invention, at least one binding epitope is on the hNKG2D protein. The anti-NKG2D-binding moiety may be combined with second moiety that binds to a molecule on a pro-inflammatory leukocyte, e.g., a T-cell receptor molecule (e.g. CD2, CD3, CD4, or CD8), so as to focus cellular defense mechanisms to a pro-inflammatory hNKG2D-expressing cell. In this embodiment, the bispecific antibodies can, e.g., be used to direct cytotoxic agents to, or an ADCC/CDC attack on, pro-inflammatory cells that express NKG2D. The cytotoxic agent could be, e.g., saporin, an anti-interferonalpha agent, a vinca alkaloid, the ricin A chain, methotrexate, or a radioactive isotope.

In another embodiment, the second moiety binds a cell-associated target that is presented on or expressed by cells associated with a disease state normally regulated by effector lymphocytes, such as cancer, viral infection, or the like. Thus, for example, a typical target may be a cell stress-associated molecule such as a MIC molecule (e.g., MIC-A or MIC-B) or a ULBP (e.g., Rae-1, H-60, ULBP2, ULBP3, HCMV UL18, or Rae-1β) or a pathogen-associated molecule such as a viral hemagglutinin.

Other multispecific molecules include those produced from the fusion of a hNKG2D-binding antibody moiety to one or more other non-antibody proteins. Such multispecific proteins and how to construct them have been described in the art. See, e.g., Dreier et al. (Bioconjug. Chem. 9(4): 482-489 (1998)); U.S. Pat. No. 6,046,310; U.S. Patent Publication No. 20030103984; European Patent Application 1 413 316; US Patent Publication No. 20040038339; von Strandmann et al., Blood (2006; 107:1955-1962.), and WO 2004056873. According to the present invention, the non-antibody protein could be, for example, a suitable ligand for any of the antigens of "second moiety" described I the preceding section; e.g., a ligand for a T-cell or Fc receptor, or a cell-stress molecule such as MIC-A, MIC-B, ULBP, or a pathogen-associated molecule such as a viral hemagglutinin.

Multispecific molecules with more than two valencies are also contemplated. For example, trispecific antibodies can be prepared. Tutt et al., J. Immunol, 147: 60 (1991).

The multispecific molecules of the present invention can be prepared by conjugating the constituent binding specificities using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described or reviewed in, for example in U.S. Pat. Nos. 5,260,203; 5,455,030; 4,881,175; 5,132,405; 5,091,513; 5,476,786; 5,013,653; 5,258,498; 5,482,858; U.S. Patent application publication 20030078385, Kontermann et al., (2005) Acta Pharmacological Sinica 26(1):1-9; Kostelny et al., (1992) J. Immunol. 148(5):1547-1553; Hollinger et al., (1993) PNAS (USA) 90:6444-6448; and Gruber et al. (1994) J. Immunol. 152: 5368.

Antibody Variants

An antibody of the invention further can be prepared using an antibody having one or more of the VH and/or VL sequences disclosed herein as starting material to engineer a modified antibody or antibody "variant", which modified antibody may have altered properties from the parent antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody. Additionally, from antigen-binding portions of an antibody, other constructs such as antigen-binding fragments, antibody derivatives, immunoconjugates, and multispecific molecules can be prepared.

Standard molecular biology techniques can be used to prepare and express the altered antibody sequence.

Though an antibody variant or derivative typically has at least one altered property as compared to the "parent" antibody, the antibody variant or derivative can retain one, some or most of the functional properties of the anti-hNKG2D antibodies described herein, which functional properties include, but are not limited to: (a) prevents NKG2D-mediated activation of an NKG2D-expressing NK or T cell, optionally with an EC50 for reducing ligand-induced cytotoxicity lower than the EC50 for binding to the cell; (b) competes with at least one NKG2D ligand in binding to NKG2D, preferably with at least MICA and ULBP3; (c) reduces the amount of NKG2D on the surface of a NKG2D-expressing NK or T cell, preferably with at least 75%; (d) binds to cynomolgus and/or rhesus NKG2D, preferably with substantially similar efficacy or affinity; (e) binds to more than one form or conformation of NKG2D; (f) binds to NKG2D with a Kd of 1 nM or less, preferably 0.1 nM or less; (g) competes with one or more of 16F16, 16F31, MS, or 21F2, (h) competes more with 16F16, 16F31, MS, or 21F2 than with any of ON72, BAT221, 5C6, 1D11, ECM217, and 149810 in binding to hNKG2D; (i) blocks more than 90% of 16F16, MS, or 21F2 binding to cell-surface hNKG2D; (j) has less agonist activity on hNKG2D than any of ON72, BAT221, 5C6, 1D11, ECM217, and 149810. Any combination of the above-described functional features, and/or the functional features as described in the Examples, may be exhibited by an antibody of the invention.

The functional properties of the antibody variants and derivatives can be assessed using standard assays available in the art and/or described herein. For example, the ability of the antibody to bind hNKG2D can be determined using standard binding assays, such as those set forth in the Examples (e.g., Biacore, flow cytometry, or ELISAs).

Variable Region Modifications

One type of variable region engineering that can be performed is CDR grafting. Antibodies interact with target antigens predominantly through amino acid residues that are located in the six heavy and light chain complementarily determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. Sci. U.S.A. 86:10029-10033; U.S. Pat. No. 5,225,539 to Winter, and U.S. Pat. Nos. 5,530,101; 5,585,089; 5,693,762 and 6,180,370 to Queen et al.) Accordingly, another embodiment of the invention pertains to an isolated antibody, or antigen binding portion thereof, comprising: a VH region comprising CDR1, CDR2, and CDR3 sequences comprising an amino acid sequence selected from the group consisting of SEQ ID NOs: 15, 21, 48, and 54, SEQ ID NOs: 16, 22, 49, and 55, and SEQ ID NOs: 17, 23, 50, and 56, respectively, and a VL region comprising CDR1, CDR2, and CDR3 sequences comprising an amino acid sequence selected from the group consisting of SEQ ID NOs: 18, 24, 51, and 57, SEQ ID NOs: 19, 25, 52, and 58, and SEQ ID NOs: 20, 26, 53, and 59, respectively. Thus, such antibodies contain the VH and VL CDR sequences of antibodies 16F16, 16F31, MS, or 21F2, yet may contain framework sequences different from these antibodies.

The invention also provides a chimeric or humanized version of a murine anti-hNKG2D monoclonal antibody, or antigen-binding fragment thereof, which binds hNKG2D, and the use of such antibodies (e.g., in the modulation of hNKG2D-mediated physiological processes in a mammalian host). In one embodiment, the murine antibody is one of ON72, BAT221, 5C6, 1D11, 149810, and ECM217. In another embodiment, the murine antibody is not one of ON72, BAT221, 5C6, 1D11, 149810, and ECM217. Thus, such antibodies contain the VH and VL CDR sequences of ON72, BAT221, 5C6, 1D11, 149810, or ECM217, or murine monoclonal antibody different from ON72, BAT221, 5C6, 1D11, 149810, ECM217, framework sequences different from these antibodies. In one embodiment, the humanized antibody is a humanized version of ON72, comprising e.g. the amino acid sequences of SEQ ID NOS:70 and 71 heavy- and light chain, respectively.

Such framework sequences can be obtained from public DNA databases or published references that include germline antibody gene sequences. For example, germline DNA sequences for human heavy and light chain variable region genes can be found in the "dBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24:827-836; the contents of each of which are expressly incorporated herein by reference.

Preferred framework sequences for use in the antibodies of the invention are those that are structurally similar to the framework sequences used by selected antibodies of the invention, e.g., similar to the VH3_21, D3-9, JH4, VKI_L15, and JK2, or VH3_20, D3-10, JH6, VKIII_A27, and JK3, or VH4_59, JH3, VKIII_A27, and JK1, or VH5_51, D3_10_R3, JH4, VKIII_L6, and JK1 framework sequences used by the 16F16, 16F31, MS, and 21F2 antibodies. The VH CDR1, 2 and 3 sequences of 16F16, 16F31, MS, or 21F2, and the VL CDR1, 2 and 3 sequences of 16F6, 16F31, MS, or 21F2 can be grafted onto framework regions that have the same sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

In another aspect of the invention, the structural features of anti-hNKG2D antibodies of the invention, e.g., 16F16 and 16F31, are used to create structurally related anti-hNKG2D antibodies that retain at least one functional property of the antibodies of the invention, such as binding to hNKG2D. For example, one or more CDR regions of 16F16 or 16F31, or variants thereof, can be combined recombinantly with known framework regions and/or other CDRs to create additional, recombinantly-engineered, anti-hNKG2D antibodies of the invention. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-hNKG2D antibody comprising: (a) providing: (i) a heavy chain variable region antibody sequence comprising a CDR1 sequence selected from SEQ ID NOs:15, 21, 48, and 54, a CDR2 sequence selected from SEQ ID NOs:16, 22, 49, and 55, and/or a CDR3 sequence selected from SEQ ID NOs:17, 23, 50, and 56; and (ii) a light chain variable region antibody sequence comprising a CDR1 sequence selected from SEQ ID NOs: 18, 24, 51, and 57, a CDR2 sequence selected from SEQ ID NOs:19, 25, 53, and 59 and/or a CDR3 sequence selected from SEQ ID NOs:20, 26, 53, and 59; (b) altering at least one amino acid residue within the first antibody sequence and/or the second antibody sequence to create at least one altered antibody sequence; and (c) preparing the altered antibody sequence; and (d) expressing the altered antibody sequence as a protein.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions. Moreover, typically no more than 8, more typically no more than 5 residues are altered within a single CDR region.

Accordingly, in another embodiment, the invention provides isolated anti-hNKG2D antibodies, comprising a heavy chain variable region comprising: (a) a VH CDR1 region comprising an amino acid sequence selected from SEQ ID NOs: 15, 21, 48, and 54, or an amino acid sequence having one, two, three, four, five, six, seven, or eight amino acid substitutions, deletions or additions as compared to an amino acid sequence selected from SEQ ID NOs:15, 21, 48, and 54; (b) a VH CDR2 region comprising an amino acid sequence selected from SEQ ID NOs:16, 22, 49, and 55, or an amino acid sequence having one, two, three, four, five, six, seven or eight amino acid substitutions, deletions or additions as compared to an amino acid sequence selected from SEQ ID NOs:16, 22, 49, and 55; (c) a VH CDR3 region comprising an amino acid sequence selected from SEQ ID NOs:17, 23, 50, and 56, or an amino acid sequence having one, two, three, four, five, six, seven or eight amino acid substitutions, deletions or additions as compared to an amino acid sequence selected from SEQ ID NOs:17, 23, 50, and 56; (d) a VL CDR1 region comprising an amino acid sequence selected from SEQ ID NO:18, 24, 51, and 57, or an amino acid sequence having one, two, three, four, five, six, seven, or eight amino acid substitutions, deletions or additions as compared to an amino acid sequence selected from SEQ ID NO:18, 24, 51, and 57; (e) a VL CDR2 region comprising an amino acid sequence selected from the group consisting of SEQ ID NOs:19, 25, 52, and 58, or an amino acid sequence having one, two, three, four, five, six, seven, or eight amino acid substitutions, deletions or additions as compared to an amino acid sequence selected from the group consisting of SEQ ID NOs:19, 25, 52, and 58; and (f) a VL CDR3 region comprising an amino acid sequence selected from the group consisting of SEQ ID NOs: 20, 26, 53, and 59, or an amino acid sequence having one, two, three, four, five, six, seven, or eight amino acid substitutions, deletions or additions as compared to an amino acid sequence selected from the group consisting of SEQ ID NOs:20, 26, 53 and 59.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for 16F16, amino acid residue R111 (Kabat residue 103; within FR4) of VH is an arginine whereas this residue in the corresponding germline sequence is a tryptophan (see FIG. 5A). To return the framework region sequences to their germline configuration, some or all of the somatic mutations can be "backmutated" to the germline sequence by, for example, site-directed mutagenesis or PCR-mediated mutagenesis (e.g., residue 111 of the VH of 16F16 can be "backmutated" from threonine to alanine). As another example, for 16F31, amino acid residue Y95 (within FR3) of the VH region is a tyrisone whereas this residue in the corresponding germline sequence is a histidine (see FIG. 5C). To return the framework region sequences to their germline configuration, the somatic mutation can be "backmutated" from tyrosine to histidine. As another example, for MS, Kabat residues 3, 6, and 7 of the VH region are histidine (H), aspartic acid (D), and D, respectively, whereas these residues in the corresponding germline sequences are glutamine (Q), glycine (G), and G, respectively (see FIG. 5E). For 21F2, Kabat residues 13, 24, 76, and 93 are glutamic acid (E), asparagine (N), N, and G, respectively, whereas these residues in the corresponding germline sequences are lysine (K), G, serine (S), and alanine (A), respectively. To return the framework region sequences to their germline configuration, the somatic mutations can be similarly "backmutated". Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Fc Modifications

In addition or as an alternative to modifications made within the framework or CDR regions, antibodies of the invention may be engineered to include modifications within the Fc region, typically to alter one or more functional properties of the antibody, such as serum half-life, complement fixation, Fc receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The residues in the Fc region are numbered according to Kabat.

If desired, the class of an antibody may be "switched" by known techniques. Such techniques include, e.g., the use of direct recombinant techniques (see e.g., U.S. Pat. No. 4,816,397) and cell-cell fusion techniques (see e.g., U.S. Pat. No. 5,916,771). For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses. Exemplary cDNA sequences for constant regions are available via, e.g., GenBank (accessible via NCBI and other public websites), each of which incorporated by reference in its entirety, are as follows:

Human IgG1 constant heavy chain region: GenBank accession No.: J00228;
Human IgG2 constant heavy chain region: GenBank accession No.: J00230;
Human IgG3 constant heavy chain region: GenBank accession No.: X04646;
Human IgG4 constant heavy chain region: GenBank accession No.: K01316; and
Human kappa light chain constant region: GenBank accession No.: J00241.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, and T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effecter function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both to Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for Fcγ RI, Fcγ RII, Fcγ RIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcRIII. Additionally, the following combination mutants were shown to improve Fcγ RIII binding: T256A/S298A, S298A/E333A, S298A/K224A and S298A/E333A/K334A.

The constant region may further be modified to stabilize the antibody, e.g., to reduce the risk of a bivalent antibody separating into two monovalent VH-VL fragments. For example, in an IgG4 constant region, residue S241 may be mutated to a proline (P) residue to allow complete disulphide bridge formation at the hinge (see, e.g., Angal et al., Mol Immunol. 1993; 30:105-8).

Glycosylation Modifications

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation "machinery". Cells with such alterations have been described in the art and can be used as host cells in which to express recombinant antibodies of the invention to thereby produce an antibody with altered glycosylation. For example, EP1176195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 7:176 180).

In certain embodiments of the methods of engineering antibodies of the invention, mutations can be introduced randomly or selectively along all or part of an anti-hNKG2D antibody coding sequence (e.g., 16F16, 16F31, MS, or 21F2 coding sequence) and the resulting modified antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof.

Alternatively, PCT Publication WO 03/074679 by Lazar et al. describes methods of using computational screening methods to optimize physiochemical properties of antibodies.

Antibody Derivatives

Antibody derivatives (or immunoconjugates) within the scope of this invention include anti-hNKG2D antibodies conjugated or covalently bound to a second agent.

For example, in one aspect, the invention provides immunoconjugates comprising an antibody conjugated or covalently bonded to a cytotoxic agent. The term "cytotoxic agent" as used herein is a molecule that is capable of killing a cell bearing a hNKG2D receptor on its cell surface. Any type of moiety with a cytotoxic or cytoinhibitory effect can be conjugated to the present antibodies to form a cytotoxic conjugate of the present invention and to inhibit or kill specific NK receptor expressing cells, including therapeutic radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

In another embodiment, the antibody is derivatized with a radioactive isotope, such as a therapeutic radionuclide or a radionuclide suitable for detection purposes. Any of a number of suitable radioactive isotopes can be used, including, but not limited to, I-131, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

The antibody conjugates of the invention can be used to modify a given biological response, where the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-y; or, biological response modifiers such as, for example, lymphokines, interleukin-I ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The second agent can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antibody, Immunicon. Radiopharm. 2:217; the entire disclosures of each of which are herein incorporated by reference). See, also, e.g. Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et a/. (eds.), pp. 303-16 (Academic Press 1985), and Thorpe et al., "The Preparation And Cytotoxic Properties Of Antibody-Toxin Conjugates", Immunol. Rev., 62:119-58 (1982).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

In other embodiments, the second agent is a detectable moiety, which can be any molecule that can be quantitatively or qualitatively observed or measured. Examples of detectable markers useful in the conjugated antibodies of this invention are radioisotopes, fluorescent dyes, or a member of a complementary binding pair, such as a member of any one of: and antigen/antibody (other than an antibody to NKG2D), lectin/carbohydrate; avidin/biotin; receptor/ligand; or molecularly imprinted polymer/print molecule systems.

The second agent may also or alternatively be a polymer, intended to, e.g., increase the circulating half-life of the antibody. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties. As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. For example, a full-length antibody or antibody fragment can be conjugated to one or more PEG molecules with a molecular weight of between about 1,000 and about 40,000, such as between about 2000 and about 20,000, e.g., about 3,000-12,000. To pegylate an antibody or fragment thereof, the antibody or fragment typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). In certain embodiments, the antibody to be pegylated is an aglycosylated antibody. Methods for pegylating proteins are known in the art and can be applied to the antibodies of the invention. See for example, EP154316 by Nishimura et al., International patent application PCT/US04/11494, and EP401384 by Ishikawa et al.

Nucleic Acids

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule. While the following paragraphs refer to DNA sequences or use thereof, the same methods or principles can generally be applied to mRNA sequences.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acids encoding the antibody can be recovered from the library.

Preferred nucleic acids molecules of the invention are those that encode (or comprise a nucleic acid sequence that encodes) the H and L chain sequences of the 16F16, 16F31, MS, or 21F2 antibodies of the IgG4 isotype. DNA sequences encoding the 16F16 VH and VL sequences are shown in SEQ ID NOs: 3 and 4, respectively. DNA sequences encoding the 16F31 VH and VL sequences are shown in SEQ ID NOs: 5 and 6, respectively. DNA sequences encoding the MS VH and VL sequences are those that encode for SEQ ID NOS:44 and 45, respectively. DNA sequences encoding the 21F2 VH and VL sequences are those that encode for SEQ ID NOS:46 and 47, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Antibody Production

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One preferred animal system for preparing hybridomas is the murine system. Immunization protocols and techniques for isolation of immunized splenocytes for fusion are known in the art, as are fusion partners (e.g., murine myeloma cells) and fusion procedures. Chimeric or humanized antibodies of the present invention can also be prepared based on the sequence of a murine monoclonal antibody using established techniques. For example, DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against hNKG2D can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice." The HuMAb mouse (Medarex, Inc.) contains human immunoglobulin gene miniloci that encode unrearranged human heavy (p and y) and K light chain immunoglobulin sequences, together with targeted mutations that inactivate the endogenous, u and K chain loci (see e.g., Lonberg, et al. (1994) Nature 368: 856-859). Accordingly, the mice exhibit reduced expression of mouse IgM or K, and, in response to immunization, the introduced human heavy and light chain transgenes undergo class switching and somatic mutation to generate high affinity human IgGK monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N. Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4: 117-123; Chen, J. et al. (1993) EMBO J. 12: 821-830; Tuaillon et al. (1994) J. Immunol. 152:2912 2920; Taylor, L. et al. (1994) International immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al. In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al. Still further, alternative transgenic animal systems expressing human immunoglobulin genes are available in the art and can be used to raise anti-hNKG2D antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al. Moreover, alternative transchromosomic animal systems expressing human immunoglobulin genes are available in the art and can be used to raise anti-hNKG2D antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-hNKG2D antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

When human Ig mice are used to raise human antibodies of the invention, such mice can be immunized with a purified or enriched preparation of hNKG2D antigen and/or cells expressing hNKG2D, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or enriched preparation (5-50 µg) of hNKG2D antigen can be used to immunize the human Ig mice intraperitoneally. In the event that immunizations using a purified or enriched preparation of hNKG2D antigen do not result in antibodies, mice can also be immunized with cells expressing hNKG2D, e.g., a human NK or T-cell line, or a mammalian cell expressing recombinant hNKG2D with or without DAP10, to promote immune responses.

Detailed procedures to generate fully human monoclonal antibodies to hNKG2D are described in Example 1 below. The form and amount of antigen administered (e.g., hNKG2D polypeptide or cell expressing hNKG2D), as well as administration schedules and the possible use of adjuvants such as, e.g., complete Freund's adjuvant or incomplete Freund's adjuvant, are typically optimized for each antigen-mouse system according to established methods in the art.

The immune response can be monitored over the course of the immunization protocol with plasma samples being obtained by retroorbital bleeds, and the plasma or serum can be screened by ELISA (as described below), and mice with sufficient titers of anti-hNKG2D human immunoglobulin can be used for fusions. Mice can be boosted intravenously with antigen 3 days before sacrifice and removal of the spleen. It is expected that 2-3 fusions for each immunization may need to be performed.

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the cells can be fused by electrofusion. Cells are plated at approximately $2 \times 10^5$ in a flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1× HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization. To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by spectroscopy. The monoclonal antibodies can be aliquoted and stored at −80°

Antibodies of the invention can also be produced in a host cell transfectoma using, for example, a combination of recombinant DNA techniques and gene transfection methods as is well known in the art (e.g., Morrison, S. (1985) Science 229:1202).

For example, to express the antibodies, DNAs encoding partial or full-length light and heavy chains, can be obtained by standard molecular biology techniques (e.g. PCR amplification or cDNA cloning using a hybridoma that expresses the antibody of interest) and the DNAs can be inserted into expression vectors such that the genes are operatively linked to transcriptional and translational control sequences and may serve their intended function of regulating the transcription and translation of the antibody gene.

The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)).

It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or p-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the invention may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr-CHO cells, described in Urlaub and Chasin, (1980) Proc. Nail. Acad. Sci. USA 77:4216-4220, used with a DHFR selectable marker, e. g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibody Characterization

After production or purification, or as part of a screening or selection procedure, the functional characteristics of an anti-hNKG2D antibody of the invention can be investigated. Functional properties of interest include, e.g., antibody binding specificity for hNKG2D, antibody competition with hNKG2D-ligands, antibody competition with reference antibodies (such as, e.g., 16F16, 16F31, MS, and 21F2), the epitope to which the antibody binds, the affinity of the antibody-antigen interaction, and antagonistic/agonistic properties of the antibody.

The following are brief descriptions of exemplary assays for antibody characterization. Some are further described in subsequent sections and/or described in the Examples.

(1) Antibody specificity for hNKG2D can be evaluated by confirming that the monoclonal antibody (or, as part of animal screening procedures, serum containing polyclonal antibodies) binds NKG2D expressing cells but not NKG2D negative cells. Cell lines with or without NKG2D are incubated with antibody followed by incubation with secondary antibody directly labelled, and visualised by, e.g., flow cytometry.

(2) Blockade of ligand binding can be evaluated by incubating cells expressing NKG2D with or without antibody or hybridoma supernatant, followed by incubation with a ligand-mFc protein and a secondary antibody specific for the ligand, and the level of ligand binding and blockade thereof determined by flow cytometry. Blockade can be calculated as the % ligand binding with pre-incubation compared to without pre-incubation, when lower binding is seen upon pre-incubation.

(3) Competition for binding site used by one or more reference anti-NKG2D antibodies can be evaluated in a similar manner, except that the pre-incubation can either performed with an antibody of the invention or the reference antibody (e.g., ON72 or 149810), followed by incubation with and detection of the subsequently added antibody.

(4) Affinity parameters, including on- and off-rate, of antibodies can determined on a Biacore machine. For example, hNKG2D-Fc protein can be immobilized on a chip, the antibody passed over the chip, the on- and off-rates determined, and the KD calculated.

(5) Induction of NKG2D internalisation by antibodies can be measured by incubating hNKG2D-expressing cells with or without antibody overnight, followed by re-addition of the antibody and detection of the level of NKG2D (i.e. the level of antibody bound) in a flow cytometer.

(6) The ability of an antibody to block hNKG2D-ligand mediated killing can be assessed, using, e.g., the NK cell lines NK92 or NKL as effector cells that kill $^{51}$Cr-loaded target cells expressing NKG2D ligand, either MICA, MICB, or ULBP1-4.

(7) Cross-reactivity of the human anti-NKG2D antibodies with monkey NK and CD8+ T cells but not CD4+ T cells (as in humans), can be demonstrated by flow cytometry after incubation of monkey and human PBMC's with hNKG2D antibody and secondary antibody, along with markers of the different cell types in PBMCs, and analysing NKG2D staining of the various subsets.

(8) Activation of NKG2D upon antibody binding can be measured as induction of cell-proliferation of CD8+ cells in a PBMC population upon stimulation via the T-cell receptor, CD28 and or NKG2D, with or without pre-stimulation (e.g., via TCR, CD28 and IL-2 or IL-15).

Binding Assays

The present invention provides for antibodies, and antigen-binding fragments and immunoconjugates thereof, that bind hNKG2D. Any of a wide variety of assays can be used to assess binding of an antibody to hNKG2D. Protocols based upon ELISAs, radioimmunoassays, Western blotting, BIACORE, and other competition assays, inter alia, are suitable for use and are well known in the art. Further, several binding assays, including competition assays, are described in the Examples.

For example, simple binding assays can be used, in which a test antibody is incubated in the presence of a target protein or epitope (e.g., NKG2D or a portion thereof), unbound antibodies are washed off, and the presence of bound antibodies is assessed using, e.g., radiolabels, physical methods such as mass spectrometry, or direct or indirect fluorescent labels detected using, e.g., cytofluorometric analysis (e.g. FACScan). Such methods are well known to those of skill in the art. Any amount of binding above the amount seen with a control, non-specific antibody indicates that the antibody binds specifically to the target.

In such assays, the ability of the test antibody to bind to the target cell or human NKG2D can be compared with the ability of a (negative) control protein, e.g. an antibody raised against a structurally unrelated antigen, or a non-Ig peptide or protein, to bind to the same target. Antibodies or fragments that bind to the target cells or NKG2D using any suitable assay with 25%, 50%, 100%, 200%, 1000%, or higher increased affinity relative to the control protein, are said to "specifically bind to" or "specifically interact with" the target, and are preferred for use in the therapeutic methods described below. The ability of a test antibody to affect the binding of a (positive) control antibody against NKG2D, e.g. 16F16, 16F31, MS, or 21F2, may also be assessed.

In one aspect, the invention provides for anti-hNKG2D antibodies sharing biological characteristics and/or substantial VH and/or VL sequence identity with 16F16, 16F31, MS, or 21F2. One exemplary biological characteristic is the binding to the 16F16, 16F31, MS, or 21F2 epitope, i.e., the respective regions in the extracellular domain of hNKG2D to which the 16F16, 16F31, MS, or 21F2 antibodies bind. To screen for antibodies that bind to the 16F16, 16F31, MS, or 21F2 epitope, a routine cross-blocking assay, such as that described in Antibodies, A Laboratory Manual, Cold Spring Harbor Laboratory, Ed Harlow and David Lane (1988), can be performed.

In an exemplary cross-blocking or competition assay, 16F16, 16F31, MS, or 21F2 (control) antibody and a test antibody are admixed (or pre-adsorbed) and applied to a sample containing NKG2D. In certain embodiments, one would pre-mix the control antibodies with varying amounts of the test antibody (e.g., 1:10 or 1:100) for a period of time prior to applying to the NKG2D-containing sample. In other embodiments, the control and varying amounts of test antibody can simply be admixed during exposure to the antigen/target sample. As long as one can distinguish bound from free antibodies (e.g., by using separation or washing techniques to eliminate unbound antibodies) and the control antibody from test antibody (e.g., by using species- or isotype-specific secondary antibodies, by specifically labeling the control antibody with a detectable label, or by using physical methods such as mass spectrometry to distinguish between different compounds) one will be able to determine if the test antibody reduces the binding of the control antibody to the antigen, indicating that the test antibody recognizes substantially the same epitope as the control. In this assay, the binding of the (labeled) control antibody in the presence of a completely irrelevant antibody is the control high value. The control low value is be obtained by incubating the labeled (positive) control antibody with unlabeled control antibody, where competition would occur and reduce binding of the labeled antibody.

In a test assay, a significant reduction in labeled antibody reactivity in the presence of a test antibody is indicative of a test antibody that recognizes the same epitope, i.e., one that "cross-reacts" with the labeled control antibody. Any test antibody or compound that reduces the binding of the labeled control to the antigen/target by at least 50% or more preferably 70%, at any ratio of control:test antibody or compound between about 1:10 and about 1:100 is considered to be an antibody or compound that binds to substantially the same epitope or determinant as the control. Preferably, such test antibody or compound will reduce the binding of the control to the antigen/target by at least 90%. Nevertheless, any compound or antibody that reduces the binding of a control antibody or compound to any measurable extent can be used in the present invention.

In one embodiment, competition can be assessed by a flow cytometry test. Cells bearing hNKG2D are incubated first with a control antibody that is known to specifically bind to the receptor (e.g., T or NK cells expressing hNKG2D or BaF/3 cell recombinantly expressing hNKG2D, and 16F16, 16F31, MS, or 21F2 antibody), and then with the test antibody that may be labeled with, e.g., a fluorochrome or biotin. The test antibody is said to compete with the control if the binding obtained with preincubation with saturating amounts of control antibody is 80%, preferably, 50%, 40% or less of the binding (mean of fluorescence) obtained by the antibody without preincubation with the control. Alternatively, a test antibody is said to compete with the control if the binding obtained with a labeled control (by a fluorochrome or biotin) on cells preincubated with saturating amount of antibody to test is 80%, preferably 50%, 40%, or less of the binding obtained without preincubation with the antibody. See Example 5 for an exemplary antibody competition assay.

Similar cross-blocking assays can also be used to evaluate whether a test (humanized) antibody affects the binding of a natural ligand for human NKG2D, such as MICA, MICB, ULBP1, ULBP2, ULBP3, ULBP4, or a member of the RAET1 family, simply by exchanging 16F16, 16F31, MS, or 21F2 for a suitable form of the hNKG2D-ligand. One suitable form, described in the Examples, are fusion proteins of the ligand (e.g., MICA) with the Fc-portion of an antibody. Having the ligand conjugated to an Fc-region allows for detection of the fusion protein by antibodies specific for the animal species from which the Fc-region derives, using, e.g., goat-anti-mouse antibodies to detect a murine Fc-region.

In one embodiment, a cellular assay is used in which hNKG2D-expressing cells, e.g., $CD4^+CD28^-$ cells from rheumatoid arthritis patients (or the equivalent cells from another autoimmune or inflammatory disorder) are incubated with an NKG2D ligand such as MICA, MICB, or a ULBP protein, e.g., in the form of an Fc-fusion protein, or a cell expressing any of these ligands, and the ability of an anti-NKG2D antibody or other molecule to block the activation of the cell is assessed. In an alternative assay, a baseline level of activity for the NKG2D receptor is obtained in the absence of a ligand, and the ability of the antibody or compound to cause a decrease in the baseline activity level is detected. In one type of embodiment, a high-throughput screening approach is used to identify compounds capable of blocking the activation of the receptor, or otherwise downregulating it. See Example 3 for an exemplary ligand competition assay.

Preferably, monoclonal antibodies that recognize an NKG2D epitope will react with an epitope that is present on a substantial percentage of CD4+ T cells, particularly CD4+ CD28− T cells, in patients such as rheumatoid arthritis patients, but will not significantly react with other cells, i.e., immune or non-immune cells that do not express NKG2D. Accordingly, once an antibody that specifically recognizes hNKG2D on NK or T cells, it can be tested for its ability to bind to T cells taken from patients with autoimmune or inflammatory disorders such as rheumatoid arthritis. It will be appreciated that the present invention can be used for the treatment of any disorder in which NKG2D activity is linked to the pathology of the disorder, regardless of the cell type expressing the receptor (e.g., CD4+ T cells, CD8+ T cells, NK cells, etc.), and the antibodies can be tested for their ability to bind to the receptor on whichever cell type is relevant for the particular disorder. For example, if it is observed that a particular disorder is associated with excess activity or proliferation of NKG2D-expressing NK cells, then the antibodies can be developed and tested using NK cells expressing the same receptor.

In one embodiment, the antibodies are validated in an immunoassay to test its ability to bind to NKG2D-expressing cells, e.g. CD4+CD28− T cells taken from patients with rheumatoid arthritis. For example, peripheral blood lymphocytes (PBLs) are taken from a plurality of patients, and CD4+, preferably CD4+ CD28−, cells are enriched from the PBLs, e.g., by flow cytometry using relevant antibodies. The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express NKG2D, e.g. NK cells, CD8 T cells, CD4 T cells from RA patients, etc., from a significant percentage of patients (e.g., 5%, 10%, 20%, 30%, 40%, 50% or more) can be deemed suitable for use in the present invention, both for diagnostic purposes to determine the expression of the NKG2D receptor in a patient's cells or for use in the herein-described therapeutic methods, e.g., for use as human-suitable blocking or, alternatively, cytotoxic antibodies. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACS). Such methods are well known in the art.

In some aspects of the invention, e.g., where it is not desired to kill NKG2D-expressing cells, the antibodies of the invention preferably do not demonstrate substantial specific binding to Fc receptors. Such antibodies may comprise constant regions of various heavy chains that are known not to bind Fc receptors. One such example is an IgG4 constant region. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any other antibody type can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

Functional Assays

Any suitable physiological change that reflects NKG2D activity can be used to assess the utility of a test compound or antibody. For example, one can measure a variety of effects in, e.g., cell-based assays, such as changes in gene expression, cytokine production, signaling molecule phosphorylation, cell growth, cell proliferation, pH, intracellular second messengers, e.g., Ca2+, IP3, cGMP, or cAMP, or activity such as cytotoxic activity or ability to activate other T cells. For example, the activity of the receptor can be assessed by detecting the expression of NKG2D-responsive genes, e.g., CD25, IFN-gamma, or TNF-alpha (see, e.g., Groh et al. (2003) PNAS 100: 9452-9457; André et al. (2004) Eur. J. Immunol 34: 1-11). Alternatively, NKG2D activity can be assessed by incubating CD4+CD28− NKG2D+ cells in the presence of a ligand or activating anti-NKG2D antibody, as well as an anti-CD3 antibody, to evaluate the ability of the compound or test antibody to inhibit the release of TNF-alpha or IFN-gamma by the T cells. Alternatively, CD4+CD28−NKG2D+ T cells can be incubated in the presence of ligand, e.g., MICA, MICB, ULBP-1, ULBP-2, ULBP-3, etc., or ligand-producing cells, e.g., autologous MIC+RA synoviocytes, and the ability of the test antibody or compound to inhibit cytokine production (e.g., IFN-gamma or TNF-alpha), or T cell proliferation assessed.

In vitro assays can optionally use cells taken from patients with autoimmune or inflammatory disorders such as RA, e.g. CD4+CD28− cells expressing NKG2D taken from (or cell lines derived therefrom) patients with RA, but in general any NKG2D-expressing cells can be used. For example, non-RA immune cell lines, e.g. T cell lines, can be transfected with an NKG2D-encoding transgene and used in the present assays, so long that the expression of the receptor alters the activity of the cells in a detectable way, e.g., renders them activatable by NKG2D ligand. Cell lines can, for example, be established using CD4+CD28−NKG2D+ cells from RA patients, e.g. PBLs or T cells isolated from synovial tissue. Such cells can be cultured in the presence of IL-15 to ensure continued expression of NKG2D (see, e. g., Groh et al. (2003) PNAS 100: 9452-9457, the entire disclosure of which is herein incorporated by reference).

If an anti-hNKG2D antibody reduces or blocks NKG2D interactions with one or more of its ligands, or competes with an antibody known to block hNKG2D ligand interaction, it can be useful for reducing NKG2D-mediated activation of NK or T cells. This can be evaluated by a typical cytotoxicity assays. Example 6 describes an exemplary cytotoxicity assay, NKG2D-ligand mediated killing of target cells. Here, the ability of anti-hNKG2D antibodies to reduce or inhibit the NK cell-mediated killing of MICA-transfected BaF/3 is assessed by measuring target cell release of 51Cr.

In other aspects, it may be desirable to ensure that antibodies of the invention lack substantial agonistic activity. Several assays can be used for this purpose, including the following.

One assay can evaluate proliferation and cytokine production after activation with antibodies, either soluble or plate-bound, in combination with anti-CD3 and/or anti-CD28 antibodies, of PBMCs from healthy volunteers or IBD patients. In this method, PBMCs are purified by conventional methods from healthy subjects or inflammatory bowel disease (IBD) patients. The cells are stained with CFSE (from Molecular probes, cat #C34554). To $10^7$ cells (in 0.5 ml PBS with 2% FCS) is added 1 μl CFSE (0.5 mM) and the cells are incubated at 37° C. for 10 min. Then, 2 ml FCS is added, and the mixture is left for 1 min at room temperature. The cells are then washed 3 times by centrifugation with RPMI-1640 medium (12 ml). After wash, the cells are resuspended in 1 ml media (e.g. RPMI-1640) with 2% FCS.

Ninety-six well plates are coated with 30 μl anti-mouse Fc (Jackson—Immuno Research 115-006-008) for 2 hours at room temperature, and then washed with PBS. Antibodies (anti-CD3 Bioscience cat #14-0037-82, anti-CD28 cat #348046 Becton Dickison) are added according to the scheme below and left in the well:

Cells Alone
CD3 0.1 or 0.3 ng/ml
CD3 0.1 or 0.3 ng/ml+CD28 0.2 μg/ml
CD3 0.1 or 0.3 ng/ml+CD28 0.2 μg/ml+anti-NKG2D 0.2 μg/ml
CD3 0.1 or 0.3 ng/ml+anti-NKG2D 0.2 μg/ml Next, 100.000 CFSE-labelled PBMCs are added and left for 3 days. Supernatant is then collected for analysis of cytokines, and the PBMCs are analysed by flow cytometry with regard to the type of lymphocyte with anti-CD56, anti-CD4, anti-CD8, and CFSE labelling for proliferation.

In another assay, the effect on the cytotoxic potential of CD8+ T cells towards a target cells lacking NKG2D ligands, is tested. If binding boosts the cytotoxic potential of the cells, agonistic activity is present. Briefly, IL-2 stimulated PBMC from healthy subjects are incubated with p815 cells expressing MICA, or with untransfected p815 cells and an anti-CD3 antibody, (which will lead to redirected killing by binding to the Fc receptors on p815 cells) and CD8 cytotoxic T cells. It is then analyzed whether an anti-NKG2D antibody that does not bind to p815 cells (e.g., an antibody of human IgG4 isotype) blocks MICA-NKG2D-directed binding and/or if the antibody boosts CD3-p815 redirected binding. In this manner, it can be shown that the activity of the CD8+ T cells is not enhanced by incubating p815 cells with an anti-CD3 antibody and an additional anti-NKG2D antibody, while the same anti-NKG2D antibody can shown to be functional by demonstrating that it blocks NK-MICA interaction on p815-induced killing in the same PBMC population.

In another assay, it can be explored whether NKG2D-signaling pathways and -molecules are activated by addition of one or more anti-NKG2D antibodies. NK cell lines (such as, e.g., NKL cells or NK-92 cells), or human NK or CD8+ T cells isolated from peripheral blood, can be used. For example, NKL cells can be incubated with a human anti-NKG2D antibody in solution or plate bound, with, e.g., Fc-MICA or irradiated MICA expressing cells as a control. After incubation for suitable time periods, (e.g., 5, 10, 30 min), the cells are lysed in the presence of protease and phosphatase inhibitors on ice, and analyzed for the levels of one or more phosphorylated signaling molecules that are known to be downstream of stimulation of NKG2D (e.g., Pi3K, Akt, and vav), by standard Western blotting techniques.

In animal-based assays, any physiological or pathological consequence of NKG2D activation in cells within the animal can be used to assess antibody or test compound activity.

For example, CD4+CD28−NKG2D+ cells can be introduced into the joints of an animal model, with or without co-administration of ligand producing cells such as MICA-producing synoviocytes, and inflammation or tissue damage is assessed. Test compounds or antibodies can then be introduced, and their ability to inhibit, slow, reverse, or in any way affect the inflammation or tissue damage is detected.

Experiments with rheumatoid arthritis (RA) synovial explants can also be performed to study the effects of blocking NKG2D on spontaneous release of pro-inflammatory cytokines (see, e.g., Brennan et al., Lancet 1989; 2 (8657); 244-247). In such an assay, human or humanized anti-hNKG2D antibodies are tested on RA synovial membrane cultures and compared to, e.g., murine anti-hNKG2D antibodies at concentrations shown to be useful to block ligand binding and function of NKG2D. RA synovial cells are cultured for 48 hrs in the absence or presence of anti-NKG2D antibodies or an isotype control antibody. Known anti-inflammatory drugs can be used as positive controls. The effects of the anti-NKG2D antibodies are initially tested at concentrations up to 30 μg/ml on 6 RA synovial membranes. Viability of the cells is analysed in a assay staining living cells (e.g. a MTT assay) to determine if the added reagent has any cytotoxicity. ELISA is then used to detect cytokines such as, e.g., TNFα, IL-1β and IL-6 levels in culture supernatants.

Alternatively, antibodies of the invention can be tested in experimental models of, e.g., psoriasis or ulcerative colitis. Psoriasis-affected skin sample can be transplanted onto a SCID mouse together with the patients own PBMC's, and the effect of introduction of a test compound and their ability to inhibit, slow, reverse, or in any way affect the inflammation or tissue damage, can be detected. Kjellev et al. (Eur J Immunol 2008; 37:1397-1406) and Ito et al. (Am J Physiol Gastrointest Liver Physiol 2008; 294:G199-G207) describe experimental models for assessing treatment of ulcerative colitis using anti-murine NKG2D antibody.

Pharmaceutical Formulations

In one embodiment, the present invention provides a pharmaceutical composition or formulation comprising anti-hNKG2D antibodies as described herein together with one or more carriers.

Accordingly, one exemplary aspect of the invention is a pharmaceutical formulation comprising such an antibody which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers, and/or surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient may add solvents and/or diluents prior to administration.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the formulation includes a buffer that is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation also or alternatively comprises a pharmaceutically acceptable preservative. The preservative may be selected from, e.g., the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxpropane-1,2-diol) or mixtures thereof. The preservative may, e.g., be present in a concentration from 0.1 mg/ml to 20 mg/ml, from 0.1 mg/ml to 5 mg/ml, from 5 mg/ml to 10 mg/ml, or from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19$^{th}$ edition, 1995.

In a further embodiment, the formulation also or alternatively comprises an isotonic agent. The isotonic agent may be, e.g., selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. The sugar or sugar alcohol concentration can, e.g., be between about 1 mg/ml and about 150 mg/ml. The isotonic agent can be present in a concentration from, e.g., 1 mg/ml to 50 mg/ml, from 1 mg/ml to 7 mg/ml, from 8 mg/ml to 24 mg/ml, or from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19th edition, 1995.

In a further embodiment, the formulation also or alternatively comprises a chelating agent. The chelating agent can, for example, be selected from salts of ethylenediaminetetraacetic acid (EDTA), citric acid, and aspartic acid, and mixtures thereof. The chelating agent may, for example, be present in a concentration from 0.1 mg/ml to 5 mg/ml, from 0.1 mg/ml to 2 mg/ml, or from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19$^{th}$ edition, 1995.

In a further embodiment of the invention the formulation also or alternatively comprises a stabilizer. The use of a stabilizer in pharmaceutical compositions is well-known to the skilled person. For convenience reference is made to Remington: The Science and Practice of Pharmacy, 19$^{th}$ edition, 1995. More particularly, compositions of the invention can be stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essex, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may alternatively or further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. The term "inhibit" in this context is intended to mean minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment, the formulation further or alternatively comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also or alternatively comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment, the formulation further or alternatively comprises a surfactant. The surfactant may, for example, be selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (e.g., oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

In a further embodiment, the formulation further or alternatively comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may also or alternatively be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the antibody, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block copolymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of an antibody, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the antibody compound in the form of a nasal or pulmonal spray. As a still further option, the pharmaceutical compositions containing an antibody of the invention can also be adapted to transdermal administration, e.g. by needle-free injection or from a patch, optionally an iontophoretic patch, or transmucosal, e.g. buccal, administration.

The antibody can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

$$d_a = \sqrt{\frac{\rho}{\rho_a}} d$$

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the antibody may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the antibody to form biologically inactive and/or insoluble aggregates as a result of exposure of the antibody to thermo-mechanical stresses and/or interaction with interfaces and surfaces that are destabilizing, such as hydrophobic surfaces and interfaces. Physical stability of the aqueous antibody formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to antibody aggregation, when it shows visual turbidity in daylight. Alternatively, the turbidity of the formulation can be evaluated by simple turbidity measurements well-known to the skilled person. Physical stability of the aqueous antibody formulations can also be evaluated by using a spectroscopic agent or probe of the conformational status of the antibody. The probe is preferably a small molecule that preferentially binds to a non-native conformer of the antibody. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the antibody formulation as used herein refers to chemical covalent changes in the antibody structure leading to formation of chemical degradation products with potential less biological potency and/or potential increased immunogenic properties compared to the native antibody structure. Various chemical degradation products can be formed depending on the type and nature of the native antibody and the environment to which the antibody is exposed. Elimination of chemical degradation can most probably not be completely avoided and increasing amounts of chemical degradation products is often seen during storage and use of the antibody formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the antibody formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the antibody is stable for more than 6 weeks of usage and for more than 3 years of storage.

In another embodiment of the invention the pharmaceutical formulation comprising the antibody is stable for more than 4 weeks of usage and for more than 3 years of storage.

In a further embodiment of the invention the pharmaceutical formulation comprising the antibody is stable for more than 4 weeks of usage and for more than two years of storage.

In an even further embodiment of the invention the pharmaceutical formulation comprising the antibody is stable for more than 2 weeks of usage and for more than two years of storage.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym, Humira and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and sterile water for injection. The pH is adjusted to 6.5. Alternatively, the antibody can be formulated in a solution comprising histidin, sucrose, and Polysorbate 80.

Diagnostic Applications

The hNKG2D-antibodies of the invention also have non-therapeutic applications. For example, anti-hNKG2D antibodies may also be useful in diagnostic assays for NKG2D protein, e.g. detecting its expression in specific cells, tissues, or serum. For example, anti-hNKG2D antibodies could be used in assays selecting patients for anti-hNKG2D treatment. For such purposes, the anti-hNKG2D antibodies could be used for analyzing for the presence of hNKG2D in serum or tissue specimens, testing for the presence of CD4+ T cells expressing NKG2D, or the presence of disease promoting cells expressing NKG2D (e.g., NK or CD4+ or CD8+ T cells). Such analyses could be combined with analyses testing, e.g., for the levels of soluble MICA in blood (see, e.g., WO2003089616 by Spies et al.).

For diagnostic applications, the antibody typically will be labeled with a detectable moiety. Numerous labels are available that can be generally grouped into the following categories:

(a) Radioisotopes, such as 35S, $^{14}$C, $^{125}$I, $^{3}$H, and $^{131}$I. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare-earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, "Methods for the Preparation of Enzyme-Antibody Conjugates for use in Enzyme Immunoassay," in Methods in Enzym. (Ed., J. Langone & H. Van Vunakis), Academic Press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) beta-D-galactosidase (beta-D-Gal) with a chromogenic substrate (e.g., p-nitrophenyl-beta-D-galactosidase) or fluorogenic substrate 4-methylumbelliferyl-p-beta-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin, and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-NKG2D antibody need not be labeled, and the presence thereof can be detected using a labeled secondary antibody that binds to the NKG2D antibody.

The antibodies of the present invention may be employed in any known assay method, such as competitive-binding assays, direct and indirect sandwich assays, and immuno-precipitation assays. Zola, Monoclonal Antibodies: A Manual of Techniques, pp. 147-158 (CRC Press, Inc. 1987).

For immunohistochemistry, the tissue sample may be fresh or frozen or may be embedded in paraffin and fixed with a preservative such as formalin, for example.

The antibodies may also be used for in vivo diagnostic assays. Generally, the antibody is labeled with a radionuclide or a non-radioactive indicator detectable by, e.g., nuclear magnetic resonance, or other means known in the art. Preferably, the label is a radiolabel, such as, e.g., $^{125}$I, $^{131}$I, $^{67}$Cu, $^{99m}$Tc, or $^{111}$In. The labeled antibody is administered to a host, preferably via the bloodstream, and the presence and location of the labeled antibody in the host is assayed. This imaging technique is suitably used in the detection, staging and treatment of neoplasms. The radioisotope is conjugated to the protein by any means, including metal-chelating compounds or lactoperoxidase, or iodogen techniques for iodination.

As a matter of convenience, the antibodies of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor that provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration.

Therapeutic Applications

Methods of treating a patient using a human or humanized anti-hNKG2D antibody as described herein are also provided for by the present invention. In one embodiment, the invention provides for the use of a human or humanized antibody as described herein in the preparation of a pharmaceutical composition for administration to a human patient. Typically, the patient suffers from, or is at risk for, an autoimmune or inflammatory disease or disorder.

For example, in one aspect, the invention provides a method of reducing or inhibiting hNKG2D-mediated activation of NK or T cells in a patient in need thereof, comprising the step of administering a human or humanized anti-NKG2D antibody to the patient, which antibody reduces or prevents ligand-mediated activation of the NKG2D receptor. In one embodiment, the method directed at decreasing the activity of such lymphocytes in patients having a disease in which increased NK or T cell activity is detrimental, which involves, affects or is caused by cells susceptible to lysis by NK or T cells, or which is caused or characterized by increased NK and/or T cell activity, such as an autoimmune disease or disorder or an inflammatory condition. In one aspect, the invention provides a method of reducing chronic inflammation in the patient.

Exemplary conditions or disorders to be treated with the polypeptides, antibodies and other compounds of the invention, include, but are not limited to systemic lupus erythematosis, rheumatoid arthritis, juvenile chronic arthritis, psoriatic arthritis, osteoarthritis, spondyloarthropathies (ankylosing spondylitis), systemic sclerosis (scleroderma), idiopathic inflammatory myopathies (dermatomyositis, polymyositis), Sjogren's syndrome, vasculitis, systemic vasculitis, temporal arteritis, atherosclerosis, sarcoidosis, myasthenia gravis, autoimmune hemolytic anemia (immune pancytopenia, paroxysmal nocturnal hemoglobinuria), pernicious anemia, autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis, autoimmune oophiritis), autoimmune orchitis, autoimmune uveitis, anti-phospholipid syndrome, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B. C, D, E and other non-hepatotropic viruses), autoimmune chronic active hepatitis, viral hepatitis, primary biliary cirrhosis, granulomatous hepatitis, Wegener's granulomatosis, Behcet's disease, and sclerosing cholangitis, inflammatory bowel diseases such as ulcerative colitis or Crohn's disease, celiac disease, gluten-sensitive enteropathy, and Whipple's disease, autoimmune or immune-mediated skin diseases including bullous skin diseases, erythema multiforme and contact dermatitis, dermitis herpetiformis, psoriasis, pemphigus vulgaris, vitiligo (leukoderma), allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, chronic obstructive pulmonary disease, and transplantation associated diseases including graft rejection and graft-versus-host-disease.

For example, in one aspect, the anti-NKG2D antibody is used in combination with one or more other anti-inflammatory agents, including, but not limited to, analgesic agents, immunosuppressive agents (e.g., B- or T-cell antagonists such as B-cell depletion agents and T cell inhibiting agents; complement inhibiting agents), corticosteroids, and anti-TNFalpha agents or other anti-cytokine or anti-cytokine receptor agents, and anti-angiogenic agents. Specific examples include metothrexate, TSG-6, Rituxan® or other B-cell therapies, anti-IL12 (p40) antibodies, CTLA4-Fc fusion proteins, IL-1-receptor antagonists, IL-1 antibodies, IL-15 antibodies, IL-18 antibodies, and anti-IL6R antibodies. Further examples of combination therapies are provided below.

When one or more other agents or approaches are used in combination with the present therapy, there is no requirement for the combined results to be additive of the effects observed when each treatment is conducted separately. Although at least additive effects are generally desirable, any decrease in NKG2D activity or other beneficial effect above one of the single therapies would be of benefit. Also, there is no particular requirement for the combined treatment to exhibit synergistic effects, although this is certainly possible and advantageous. The NKG2D-based treatment may precede, or follow, the other treatment by, e.g., intervals ranging from minutes to weeks and months. It also is envisioned that more than one administration of either the anti-NKG2D composition or the other agent will be utilized. The agents may be administered interchangeably, on alternate days or weeks; or a cycle of anti-NKG2D treatment may be given, followed by a cycle of the other agent therapy. In any event, all that is required is to deliver both agents in a combined amount effective to exert a therapeutically beneficial effect, irrespective of the times for administration.

The following describes some selected inflammatory and/or autoimmune diseases or disorders for which anti-hNKG2D antibodies of the invention can be used as therapeutic agents. Preferably, the anti-hNKG2D antibody is full-length bivalent MS or 21F2, or an antigen-binding fragment, variant or derivative thereof.

Rheumatoid Arthritis

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space is infiltrated by similar cells with the addition of numerous neutrophils. The pathological T cell produces cytokines and other soluble factors adding to the attraction and activation of other cells, and to the destruction of the tissue. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rhematoid nodules.

Accordingly, in one aspect, the invention provides a method for treating and/or preventing rheumatoid arthritis (RA). The method comprises delivering an effective amount of an anti-hNKG2D antibody to a patient having RA or being identified/diagnosed as being at substantial risk of developing RA, such that RA is treated or prevented. In one aspect, the anti-NKG2D antibody is demonstrated to be effective in ameliorating RA in an acceptable model of RA, such as is described in U.S. Pat. No. 6,414,218 and US Patent Publication No. 20030005469 (related principles and models are described in, e.g., Wooley, P. H., Animal Models of Arthritis, eds. J. H. Klippel and P. A. Dieppe, Mosby Publishers (London), 1998; Erning et al., Arthritis Res, 4 Suppl 3:S 133-40, 2002; Holmdahl et al., Aging Res Rev, 1(1): 135-47, 2002; Anthony et al., Clin Exp Rheumatol, 17(2):240-4, 1999; Durie et al., Clin Immunol Immunopathol, 73(1):11-8, 1994; and Muller-Ladner et al., Drugs Today (Bare), 35(4-5):379-88, 1999). In a further aspect, the antibody that is capable of detectably reducing ligand-induced NKG2D activation of NKG2D-expressing leukocytes and/or impairing expansion of NKG2D+ T cells or NK cells (e.g., impairing the expansion and/or function of auto-reactive CD8+ T cells) (in contrast to, e.g., at least some of the antibodies described in US Patent Publication No. 20040115198), without significantly depleting such cells (e.g., causing a reduction of about 10% or less of such cells as compared to a suitable control). In one aspect, the method results in a modulation of one or more biomarkers in a manner consistent with the treatment or prevention (as applicable) of RA (e.g., serum IL-6, TNF-α, IL-1, VEGF, TIFF R, IL-2R, shed CD4, shed CD8, and/or C reactive protein). In another aspect, the practice of the method results in a detectable reduction of synovial inflammation in the peripheral joints of the patient/host. In one aspect, the method results in preventing radiographic deterioration and improving physical function in the patient or host as exhibited by, e.g., a reduction in radiographic progression in the patient or host, reduction in swollen and tender joints (as determined by acceptable analytical criteria), and/or significantly improved quality of life (e.g., as determined by a reduction in disability scores on the RA Health Assessment Questionnaire). The antibody can be used alone or in combination with one or more other anti-RA agent, such as a non-steroidal anti-inflammatory drug (NSAID), a COX-2 inhibitor, an analgesic, a corticosteroid (e.g., predinisone, hydrocortisone), gold, an immunosuppressant (e.g., methotrexate), a B-cell depletion agent (e.g., Rituxan®), a B-cell agonist (e.g., LymphoStatB®) and an anti-TNFalpha agent (e.g., Embrel®, Humira® and Remicade®), an anti-IL1 receptor antagonist (e.g., Kineret®), an anti-IL-15 antibody, or a disease-modifying anti-rheumatic drug (DMARD).

Demyelinating Diseases

Demyelinating diseases of the central and peripheral nervous systems, including Multiple Sclerosis (MS); idiopathic demyelinating polyneuropathy or Guillain-Barre syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. MS is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions.

Thus, in another aspect, the invention provides a method for treating and/or preventing MS. The method comprises delivering an effective amount of an anti-hNKG2D antibody to a human patient having MS or being identified/diagnosed as being at substantial risk of developing MS, such that MS is treated or prevented in the patient or host. In a particular aspect, the anti-NKG2D monoclonal antibody is capable of detectably reducing ligand-induced NKG2D activation of NKG2D-expression leukocytes and/or impairing expansion of NKG2D+ T cells or NK cells, without significantly depleting such cells. The antibody can be used alone or in combination with other anti-MS agents such as Tyzabri®.

Inflammatory Bowel Disease

In CD8+ T cells in the intestine, NKG2D acts as a co-stimulator of CD28− cells (Roberts et al., J Immunol 2001; 167:5527-30). Furthermore, in inflammation of the intestine (celiac disease), NKG2D is upregulated, and intestinal epithelial lymphocytes are stimulated via NKG2D to kill and produce cytokines (Hue et al., Immunity 2004; 21:367-77; Meresse et al., Immunity 2004; 21:357-66).

Additionally, IL-15, often found during intestinal inflammation, upregulates NKG2D on intestinal epithelial lymphocytes (Roberts et al., J Immunology 2001; 167:5527-30). Furthermore, during intestinal inflammation, MICA, a ligand for NKG2D, is upregulated (Meresse et al, supra, Hue et al., supra). NKG2D is also upregulated on proinflammatory lymphocytes of patients with Crohn's disease (Allez et al., presentation at 16th European Congress of Immunology (EC12006), Sep. 6-9, 2006; Paris, France).

Thus, in another aspect, the invention provides a method for treating and/or preventing inflammatory bowel disease (IBD), such as Crohn's disease or ulcerative colitis. As shown by Kjellev et al. (Eur J Immunol 2008; 37:1397-1406), inhibition of NKG2D-receptor function by early antibody therapy attenuated transfer-induced colitis in SCID mice, an animal model of colitis.

The method of treating an inflammatory bowel disease comprises delivering an effective amount of an anti-NKG2D antibody to a human patient having IBD or being identified/diagnosed as being at substantial risk of developing IBD, such that IBD is treated or prevented in the patient. In a particular aspect, the inventive IBD treatment/prevention method is practiced by use of an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells. The antibody can be used alone or in combination with other anti-IBD agents, such as drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., predinisone, hydrocortisone), TNF-inhibitors (including adilimumab (Humira®), etanercept (Enbrel® and infliximab (Remicade®), anti-IL12 antibodies, immunosuppressants (such as 6-mercaptopurine, azathioprine and cyclosporine A), and antibiotics.

Psoriasis

Psoriasis is a T lymphocyte-mediated inflammatory disease. Lesions contain infiltrates of T lymphocytes, macrophages and antigen processing cells, and some neutrophils.

Thus, in another aspect, the invention provides a method for treating and/or preventing psoriasis. The method comprises delivering an effective amount of an anti-hNKG2D antibody to a human patient having psoriasis or being identified/diagnosed as being at substantial risk of developing psoriasis, such that psoriasis is treated or prevented in the patient. In a more particular aspect, the agent is an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells. The antibody can be used alone or in combination with one or more other antipsoriasis treatments such as phototherapy, topical therapy (e.g., tar, topical glucocorticoids), or systemic therapy (e.g., methotrexate, a synthetic retinoid, cyclosporine), an anti-TNFα lpha agent (e.g., Embrel®, Humira®, Remicade®), a T-cell inhibitor (e.g., Raptiva®), vitamin D analogs, p38 mitogen-activated protein kinase (MAPK) inhibitors, as well as a biologic agent such as Rituxan®.

Psoriatic Arthritis

Psoriatic arthritis is a chronic inflammatory arthritic condition affecting the skin, the joints, the insertion sites of tendons, ligaments, and fascia, and is commonly associated with psoriasis. (approximately 7% of patients with psoriasis develop psoriatic arthritis). Much evidence suggests that a T-cell-mediated process drives the pathophysiology of psoriatic arthritis. Monocytes also play a role in psoriatic arthritis and are responsible for the production of matrix metalloproteinases, which may mediate the destructive changes in the joints of patients with psoriatic arthritis. Furthermore, NK cells are also found in affected joints, suggesting a role in the disease pathology.

Thus, in another aspect, the invention provides a method for treating and/or preventing psoriatic arthritis. The method comprises delivering an effective amount of an anti-hNKG2D antibody to a human patient having psoriatic arthritis or being identified/diagnosed as being at substantial risk of developing psoriatic arthritis, such that the psoriatic arthritis is treated or prevented in the patient. In a more particular aspect, the agent is an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells. The antibody can be used alone or in combination with one or more other anti-psoriatic arthritis treatments such as nonsteroidal anti-inflammatory drugs (aspirin, ibuprofen), methotrexate, a synthetic retinoid, cyclosporine, a corticosteroid, an anti-TNFα lpha agent (e.g., Embrel®, Humira®, Remicade®).

Systemic Lupus Erythematosus

In systemic lupus erythematosus (SLE), the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Thus, in another aspect, the invention provides a method for treating and/or preventing SLE. The method comprises delivering an effective amount of an anti-hNKG2D antibody to a human patient having SLE or being identified/diagnosed as being at substantial risk of developing SLE, such that the SLE is treated or prevented in the patient. In a more particular aspect, the agent is an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells. The antibody can be used alone or in combination with other anti-SLE agents, such as non-steroidal anti-inflammatory drugs (NSAIDs), analgesics, corticosteroids (e.g., predinisone, hydrocortisone), immunosuppressants (such as cyclophosphamide, azathioprine, and methotrexate), anti-malarials (such as hydroxychloroquine) and biologic drugs that inhibit the production of dsDNA antibodies (e.g. LJP 394).

Diabetes

Type I diabetes mellitus or insulin-dependent diabetes is the autoimmune destruction of pancreatic islet B cells; this destruction is mediated by auto-antibodies and autoreactive T cells. Antibodies to insulin or the insulin receptor can also produce the phenotype of insulin-non-responsiveness.

Thus, in another aspect, an anti-NKG2D antibody is delivered to a patient suffering from or at substantial risk of developing type I diabetes mellitus in an amount and under conditions sufficient to treat or prevent the condition in the patient. The antibody can be used alone or in combination with other anti-diabetic agents, such as insulin, or beta cell growth or survival factors, or immunomodulatory antibodies such as anti-CD3 antibodies.

Transplantation

Transplantation associated diseases, including graft rejection and Graft-Versus-Host-Disease (GVHD) are T lymphocyte-dependent; inhibition of T lymphocyte function is ameliorative.

Thus, in another aspect, the invention provides methods of reducing the likelihood of transplant rejection (or reducing the severity or prolonging the time to onset of a transplant rejection-related condition, i.e., to prolong allograft survival). The method comprises delivering an effective amount of an anti-hNKG2D antibody to a human patient that is about to be, is, or recently was the recipient of a tissue/organ transplant, such that the likelihood of rejection is detectably reduced (e.g., as compared to a control). In a particular aspect, the anti-NKG2D antibody is capable of detectably reducing ligand-induced NKG2D activation of NKG2D-expression leukocytes and/or impairing expansion of NKG2D+ T cells or NK cells, without significantly depleting such cells. Examples of tissue transplants that can be treated include, but are not limited to, liver, lung, kidney, heart, small bowel, and pancreatic islet cells, as well as in bone marrow-transplantation and in the treatment of graft versus host disease (GVHD). The antibody can be used alone or in combination with other agents for inhibiting transplant rejection, such as immunosuppressive agents (e.g. cyclosporine, azathioprine, methylprednisolone, prednisolone, prednisone, mycophenolate mofetil, sirilimus, rapamycin, tacrolimus), anti-infective agents (e.g., acyclovir, clotrimazole, ganciclovir, nystatin, trimethoprimsulfarnethoxazole), diuretics (e.g. bumetanide, furosemide, metolazone) and ulcer medications (e.g., cimetidine, farnotidine, lansoprazole, omeprazole, ranitidine, sucralfate). For hematopoietic transplantation, hematopoietic growth factor(s) (e.g., erythropoietin, G-CSF, GM-CSF, IL-3, IL-11, thrombopoietin, etc.) or antimicrobial(s) (e.g., antibiotic, antiviral, antifungal) may be administered as an adjunct therapy.

Other Autoimmune or Inflammatory Diseases

In other separate aspects, the invention provides methods for treating and/or preventing other autoimmune or inflammatory diseases or disorders, comprising delivering an effective amount of an anti-hNKG2D antibody to a human patient having the disease or disorder or being identified/diagnosed as being at substantial risk of developing the disease or disorder, such that it is treated or prevented in the patient, where the disease or disorder is one described below. In a more particular aspect, the agent is an anti-NKG2D monoclonal antibody that is capable of detectably reducing ligand-induced NKG2D activation of NKG2D-expressing leukocytes and/or impairing expansion of NKG2D+ T cells or NK cells, without significantly depleting such cells. The antibody can be used alone or in combination with one or more other therapeutic agents used for treating the disease or disorder.

Juvenile chronic arthritis is a chronic idiopathic inflammatory disease which begins often at less than 16 years of age. Its phenotype has some similarities to RA; some patients which are rhematoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often unregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNAs, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or Fc-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte dependent.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Another disease suitable for treatment with a human anti-NKG2D antibody is viral hepatitis, as shown in WO2007130642 and by Chen et al. (Hepatology, Vol. 46 (3) pp. 706-715 (2007)).

It will be understood that the effective amount of the NKG2D modulator, as well as the overall dosage regimen, may vary according to the disease and the patient's clinical status, which, in turn, may be reflected in one or more clinical parameters such as clinically accepted disease scores. For example, for rheumatoid arthritis, the severity of disease and/or outcome of treatment, may be evaluated by monitoring number of swollen joints; pain; mobility; and/or the official disease score ACR 20/50 or 70. For Type 1 diabetes, severity of disease and/or outcome of treatment may be evaluated by measuring blood glucose levels or variations thereof, HbIC levels, the amount of insulin needed, and the like. For multiple sclerosis, brain inflammation can be assessed through scanning the brain. For hematopoietic transplant rejection, severity of the disease (failure to engraft) and/or outcome of treatment may be evaluated by evidence of prolonged neutropenia, thrombocytopenia, and red-cell transfusion dependence in patients that have undergone myeloablative conditioning, and by failure to observe chimerism in patients that have undergone non-myeloablative conditioning. In general, detectable effects on treatment outcome using the methods and compositions of the present invention include a decrease in the necessity for other treatments (including, e.g., a decrease in the amount and/or duration of other drugs or treatments), a decrease in number and/or duration of hospital stays, a decrease in lost work days due to illness, and the like. It will be further understood that the effective amount may be determined by those of ordinary skill in the art by routine experimentation, by constructing a matrix of values and testing different points in the matrix.

Dosages

For administration of the antibody, the dosage ranges from about 0.0001 to 100 mg/kg, and more usually 0.01 to 5 mg/kg, of the host body weight. For example, dosages can be about 0.3 mg/kg body weight, about 1 mg/kg body weight, about 3 mg/kg body weight, about 5 mg/kg body weight or about 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Preferred dosage regimens for an anti-hNKG2D antibody of the invention include about 1, 3 or 10 mg/kg body weight body weight via intravenous administration or subcutaneous injection, with the antibody being given using one of the following dosing schedules: (i) loading doses every 1-3 weeks for 2-4 dosages, then every two; months (ii) every four weeks; (iii) every week, or any other optimal dosing. In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or non-prophylactic (e.g., palliative or curative). In prophylactic applications, a relatively low dosage is administered at relatively infrequent intervals over a long period of time. Some patients continue to receive treatment for the rest of their lives. In palliative or curative applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The appropriate doses of anti-inflammatory agents will approximate those already employed in clinical therapies wherein the anti-inflammatory agents are administered alone or in combination with other agents. Variation in dosage will likely occur depending on the condition being treated. The physician administering treatment will be able to determine the appropriate dose for the individual subject.

Articles of Manufacture

In another embodiment of the invention, an article of manufacture containing materials useful for the treatment of the disorders described above is provided. For example, the article of manufacture can comprise a container containing a human or humanized anti-hNKG2D antibody as described herein together with instructions directing a user to treat a disorder such as an autoimmune or inflammatory disease or disorder in a human with the antibody in an effective amount. The article of manufacture typically comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example, the container may be an intravenous solution bag or a vial having a stopper pierceable by a hypodermic injection needle). At least one active agent in the composition is the human or humanized anti-hNKG2D antibody herein, or an antigen-binding fragment or antibody derivative (e.g., an immunoconjugate) comprising such an antibody. The label or package insert indicates that the composition is used for treating the condition of choice, such as, e.g., rheumatoid arthritis.

Moreover, the article of manufacture may comprise (a) a first container with a composition contained therein, wherein the composition comprises the human or humanized antibody herein, and (b) a second container with a composition contained therein, wherein the composition comprises a therapeutic agent other than the human or humanized antibody. The article of manufacture in this embodiment of the invention may further comprise a package insert indicating that the first and second compositions can be used in combination to treat an autoimmune or inflammatory disease or disorder. Such therapeutic agents may be any of the adjunct therapies described in the preceding section. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Further details of the invention are illustrated by the following non-limiting Examples.

Example 1: Generation and Initial Screening of Human Monoclonal Antibodies Against hNKG2D Materials and Methods
Antigen.
Soluble NKG2D-hFc fusion protein (R&D, cat: 1299-NK) or NKG2D expressed on the surface of cells (NK, BAF, or CHO) were used as antigens for immunization. The BAF cells were co-transfected with full-length NKG2D and DAP10. The CHO cells were transfected with an NKG2D point mutant that transports to the cell surface without DAP10 (Wu et al., Science 1999; 385:730-2). The NK cells were primary NK cells naturally expressing NKG2D.
Mice.
Fully human monoclonal antibodies against NKG2D were produced in the KM Mouse™ strain of transgenic mice that express human antibody genes (PCT publication WO 02/43478 to Ishida et al.). In this mouse strain, the endogenous kappa light chain gene has been homozygously disrupted as described in Chen et al (1993) EMBO J. 12:811-820, and the endogenous mouse heavy chain has been homozygously disrupted as described in Example 1 of PCT Publication WO 01/09187 for Humab mice. The mouse strain carries a human kappa light chain transgene, KC05, as described in Fishwild et al (1996) Nature Biotechnology 14:845-851. The mouse strain also carries a human heavy chain transchromosome, SC20, as described in WO0243478.
Immunizations.
In a first series of immunizations, animals were immunized intraperitoneally with alternating injections of NKG2D-transfected BAF cells and NKG2D-transfected CHO cells, or primary human NK cells with or without any adjuvant. Each mouse was immunized IP with $5\times10^6$ cells every or every other week (6 times in total). The mice were boosted with $5\times10^6$ NKG2D-transfected BAF cells intravenously 3 and 2 days before sacrifice and removal of the spleen. The animal experiments were performed according to Danish National Research Council guidelines.

In a second series of immunizations, animals were immunized intraperitoneally and in the foot path with NKG2D-hFc with different adjuvant. Each mouse was immunized 7×25 ug NKG2F-hFc/Ribi/ip/sc, 1×25 ug NKG2D-hFc/CFA/ip/sc, 1×25 ug NKG2D-hFc/IFA/ip/sc, 1×30 ug anti-CTLA4+40 ug NKG2D-hFc/IFA/ip/sc, 1×25 ug NKG2D-hFc/Ribi/ip/sc and boosted 2×30 ug/PBS/ip/iv 3 and 2 days before sacrifice and removal of the spleen. The animal experiments were performed according to American National Research Council guidelines.

Screening of Mouse Sera.

The sera from the immunized mice were screened by flow cytometry analysis for NKG2D-specificity and selected sera were also tested for their ability to neutralize binding of the MICA ligand, as described in Example 3. Mice that had generated high titers of antibodies that specifically bound NKG2D and neutralized MICA binding were selected for hybridoma production.

Generation of Hybridomas.

The spleen from each selected immunized mouse was homogenised and a single cell suspension of splenocytes used for fusion to X61 Ag8653 myeloma cells (ATCC, CRL 1580). The fusions were performed using polyethyleneglycol (PEG) 1500 as previously described (Harlow and Lane, ANTIBODIES: A LABORATORY MANUAL, Cold Spring Harbor Laboratory Press, Cold Spring Harbor, N.Y., (1988)) and electrofusion using the The Cyto Pulse™ CEEF-50 Electrofusion System (Cyto Pulse Sciences, Inc.).

The fused cells were initially seeded in 96-well tissue culture plates in selective DMEM HAT medium, supplemented with 10% FBS and 5% origin (Hybridoma cloning Factor, BioVeris). The plates were incubated for 10-14 days with 1-2 medium changes, respectively, to DMEM HT medium supplemented with 5% FBS and 0.7% origin, before harvest and screening of the supernatants. Clones tested positive were expanded and subcloned by limiting dilution until stable clones had been generated. The selected clones were continuously screened for the presence of anti-NKG2D specific antibodies by FACS analysis as well as for their ability to neutralize MICA binding.

Screening of Hybridoma Supernatants.

The primary screening of the hybridoma supernatants from the first series of immunizations was performed using direct ELISA or flow cytometry analysis (FACS) to test for the presence of anti-NKG2D specific antibodies. Briefly, the ELISA was performed by coating maxisorp plates with 50 µl 0.4 µg/ml mFc-NKG2D (comprising the extracellular portion of NKG2D fused to murine Fc and expressed in CHO cells) overnight in PBS at 4° C., followed by blocking with PBS, 0.05% Tween 20, for 15 min at room temperature. The plates were subsequently incubated with 50 µl hybridoma supernatant, and NKG2D-specific antibodies detected using Goat-Anti-human IgG-HRP Fcγ Fragment specific (Jackson, 109-036-098). These incubations were performed for 1 hr at room temperature, and between each step the plates were washed with PBS, 0.05% Tween 20. Bound antibodies were visualized using 100 µl TMB substrate (Kem-En-Tec), and stopped with 4M H$_3$PO$_4$. The plates were read at 450 and 620 nm. For FACS, binding to NKG2D-expressing BaF/3 cells and control BaF/3 cells not expressing NKG2D was analyzed by incubation of 50000 cells in 10 µl with 90 µl hybridoma supernatant for 30 min at 4° C., followed by washing with PBS with 2% FCS, and subsequently incubated with secondary Goat-Anti-human IgG-HRP Fcγ Fragment specific (Jackson, 109-036-098). The cells were then analysed on a B&D FACSArray (BD Biosciences). Antibodies that only stained NKG2D-expressing BaF/3 cells and not control cells were deemed NKG2D-specific.

The primary screen for the second series of immunizations was a direct ELISA to test for the presence of anti-NKG2D specific antibodies. Briefly, the ELISA was performed by coating maxisorp plates with 1-2 mg/ml hFc-NKG2D (R&D Systems) overnight in PBS at 4° C., followed by blocking with PBS, 0.05% Tween 20, 5% chicken serum for 30-60 min at room temperature. The plates were subsequently incubated with 50 µl hybridoma supernatant and 50 µl blocking buffer, and NKG2D-specific antibodies detected using Anti-human IgG-HRP (Bethyl, A80-115P) in blocoking buffer. These incubations were performed for 1 hr at room temperature, and between each step the plates were washed with PBS, 0.05% Tween 20. Bound antibodies were visualized using ABTS substrate (Moss Inc, product: ABTS-1000). The plates were read at 415 nm with Molecular Devices Software.

Hybridomas selected from an ELISA primary screen were subjected to a secondary screen using FACS, as described above.

Commercially available murine antibodies (149810 and ON72) were used as controls.

Results

Figure 1B:
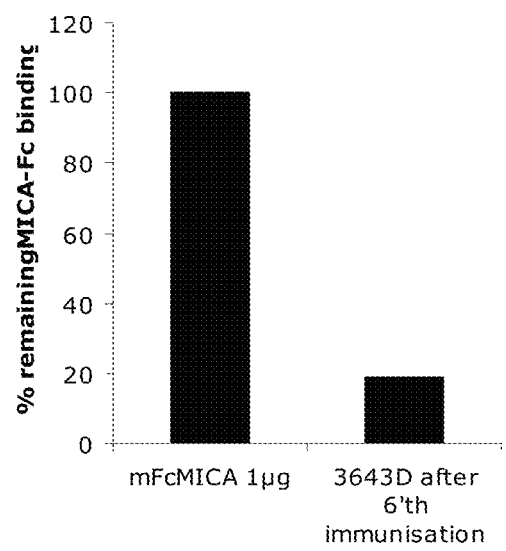
Figure 2A:
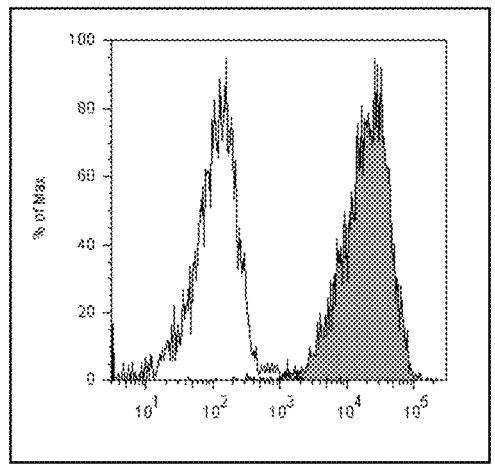
FIGS. 2A-D shows an example of a human antibody in the form of a hybridoma supernatant bound specifically to NKG2D expressing cells (FIG. 2A) but not to the same cell-line not expressing NKG2D (FIG. 2B). Antibody was added to the cells in the form of hybridoma supernatant. The binding of a directly labelled positive control, murine anti-NKG2D antibody 149810, to NKG2D expressing cells (FIG. 2C) and non expressing cells (FIG. 2D), is also shown. The black outline represents background staining, and solid peaks represent specific staining.
Figure 2B:
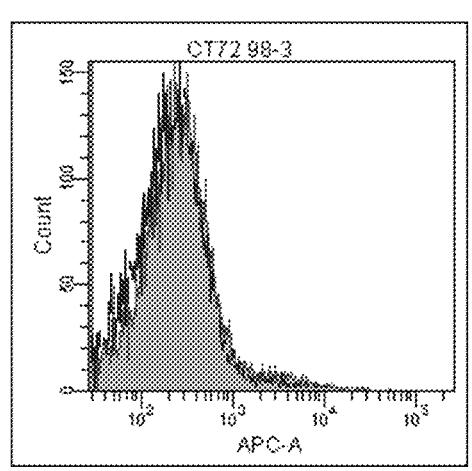
Figure 2C:
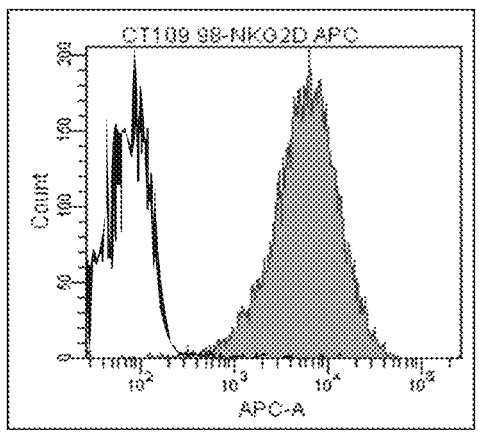
Figure 2D:
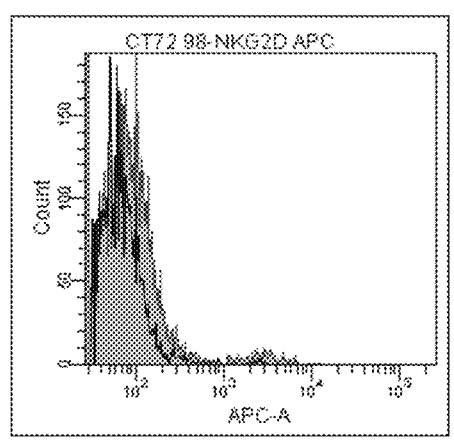

Highly selective sera from immunized mice were identified by NKG2D-binding and ligand blocking ability (exemplary results shown in FIGS. 1A and 1B), and selected mice were used for fusion and hybridoma generation. About 2500 hybridomas were screened by ELISA and flow cytometry and NKG2D-specific clones identified. FIGS. 2A-2D shows that human antibody in a hybridoma supernatant bound to NKG2D-expressing cells but not NKG2D-negative cells, comparing to a commercial antibody (149810). Antibodies from three hybridomas (16F16, 16F31 and 21F2) from the first series of immunization, and several antibodies from the second series of immunizations (including MS), were selected for recombinant production and further testing.

Example 2: Recombinant Production and Sequencing

A second batch of several hundreds of hybridomas from fusions mice spleens expressing human antibodies were obtained from a separate round of immunization(s). These were screened for NKG2D-specificity using FACS in the same manner as described in Example 1. Antibodies from one hybridoma, MS, were selected for recombinant production and further testing.

The variable regions of the heavy and light chains of the antibodies were identified by PCR and subsequent sequencing of the isolated product, of mRNA from the hybridoma.

Materials and Methods

RNA purification.

Total RNA was purified using RNeasy from Qiagen according to the manufactures instructions, except that β-mercaptoethanol was omitted from the procedure. The quality of the RNA was checked by light spectroscopy (260/280 nm, 1.8<ratio<2.0) and occasionally RNA degradation was evaluated using a bioanalyser.

RT-PCR.

Full length cDNA was synthesised by SMART-RACE (kit from Clonetech).

PCR.

PCR was performed with the HFII polymerase from Clonetech. The 5' primer (with EcoRI) annealed to a conserved sequence introduced during SMART-RACE. Two 3' primers were designed that anneal to conserved regions of the IgG (VH) and kappa chains (VL), respectively. Restriction sites were also present in the 3' primers (BsiWI (VL) and NheI (VH)). The PCR was performed in duplicate (to check for PCR introduced mutations) for all VH and VL amplifications. If the PCR reaction failed, the VL and VH were amplified using a degenerate 5' primer mix from Novagen.

PCR Product Purification.

The PCR product (~550 bp) was separated on a 1% agarose gel, excised, purified on GFX columns (from Amersham) and eluted in DNAse free water.

Ligation.

The PCR products and the expression vector (ampicillin resistance) were cut with appropriate restriction enzymes (VH, EcoRI+NheI and VL, EcoRI+BsiWI). The ligation of the variable domains into the isotype-dictating vector (IgG4 for NKG2D) was catalyzed by the T4-ligase (Roche). The plasmid used was pTT5 (Durocher et al., Nucleic Acids Res 2002; 30(2):e9; Pham et al., Biotechnol Bioeng 2003; 84(3): 332-42).

Check of Insert in the Expression Vector (Colony PCR).

Competent E. coli (Top 10) were transformed with the ligation mix and ampicillin resistant clones were selected overnight. In total, 8 positive colonies for both VH and VL were picked. Via colony PCR and gel electrophoresis (1% agarose), all colonies were checked for inserts matching the expected size.

Sequencing/Miniprep.

An aliquot from all positive colony PCRs was prepared for sequencing (using ExoSAPit). In total, 32 PCR products were sequenced for each clone ((8*VH+8*VL)*2 (PCR in duplicate)). The sequences were analysed (using VectorNTI) and positive bacteria clones corresponding to the cloned VH and VL were up-scaled (mini/maxiprep), and the DNA purified for HEK293/6E transfection (GFX columns). If more than one VH and VL sequence was identified, then all possible VL and VH combinations were expressed in HEK293/6E cells.

Recombinant Production.

The identified variable regions of heavy and light chains were inserted into heavy and light chain human IgG4 framework respectively and expressed from two vectors in HEK293 cells at a high level. The antibodies were purified on a protein A column.

Antibody Expression in HEK293/6E Cells.

HEK293 cells were passaged in Freestyle293 medium from Gibco. On the day of transfection, cells were diluted to a concentration of 1 million cells/ml. For a 30 ml transfection, 15 µg of heavy-chain vector and 15 µg of light-chain vector were mixed with 2 ml Opti-MEM and 40 µl 293fectin (then Freestyle293 medium to a total volume of 30 ml). After 6 days of incubation, cells were pelleted by centrifugation (1000 rpm, 10 min) and the supernatant was harvested for protein A purification.

Purification.

The recombinantly expressed IgG4 variants of the human antibodies was purified on MabSelect™ SuRe protein-A columns. After column application of antibody, the column was washed with 10 column volumes of PBS buffer, and antibody eluted with 100 mM Glycine, 100 mM NaCl buffer, pH 3.0, followed by buffer exchange into PBS buffer using a HighTrap™ Desalting column. All operations were controlled by an Aktaxpress system from GE Healthcare Amersham Biosciences AB.

The typical concentration range of purified antibody was from 10-130 mg/l (0.3-3.3 mg/30 ml).

Results cDNA sequences encoding 16F16 (IgG4) H chain, 16F16 L chain, 16F31 (IgG4) H chain, and 16F31 L chain are set forth in SEQ ID NOS:3-6, respectively, and respective sequence identifiers of full-length, variable, and CDR amino acid sequences of 16F16 (IgG4), 16F31 (IgG4), MS (IgG4) and 21F2 (IgG4) are set forth in Table 1. FIGS. 4A and 4B shows the amino acid sequences for 16F16, 16F31, MS, and 21F2 of IgG4 isotype, high-lighting variable (bold) and CDR (bold underline) regions.

Using the JointMLc algorithm for IgH joint composition and the D-classification described in Ohm-Laursen et al., (Immunology 2006; 119:265-77), the following germline sequences for the variable regions were identified for 16F16 and 16F31:

| | |
|---|---|
| 16F16 VH: VH3_21/D3-9/JH4 | (SEQ ID NOS: 31/32/33, respectively) |
| 16F16 VL: VKI_L15/JK2 | (SEQ ID NOS: 34/35, respectively) |
| 16F31 VH: VH3_20/D3-10/JH6 | (SEQ ID NOS: 36/(EL)/37, respectively) |
| 16F31 VL: VKIII_A27/JK3 | (SEQ ID NOS: 38/39, respectively) |
| MS VH: VH4_59/D3_27_R3/JH3 | (SEQ ID NOS: 64/(NWG)/65, respectively) |
| MS VL: VKIII_A27/JK1 | (SEQ ID NOS: 38/66, respectively) |
| 21F2 VH: VH5_51/D3_10_R3/JH4 | (SEQ ID NOS: 67/68/33, respectively) |
| 21F2 VL: VKIII_L6/JK1 | (SEQ ID NOS: 69/66, respectively) |

Alignments of VH and VL sequences with the corresponding recombined germline sequences (SEQ ID NOS: 27-30 correspond to recombined VH3_21/D3-9/JH4, VKI_L15/JK2, VH3_20/D3-10/JH6, and VKIII_A27/JK3, respectively, and SEQ ID NOS:60-63 correspond to recombined VH4_59/D7_27_3/JH3, VKIII_A27/JK1, VH5_51/D3_10_R3/JH4, and VKIII_L6/JK1, respectively) indicating somatic hypermutations, are shown in FIGS. 5A-5H.

Example 3: MICA Blocking Experiments

Materials and Methods

Flow Cytometry Assays—MICA Blockade.

For analysis of blockade of ligand binding, 50000 NKG2D/DAP10-expressing BaF/3 cells were incubated in 100 µl total (PBS with 2% FBS at pH7.4) with varying amounts of hybridoma supernatant or purified antibody for 1 h at 16° C., followed by incubation with mFc-MICA (for human antibodies) or hFc-MICA (for ON72) (1 µg) for 30 min at 4° C. The cells were thereafter washed, and secondary Goat-Antimouse IgG-HRP Fcγ Fragment specific, Jackson (109-036-151) was added for detection of MICA-mFc binding. The cells were then analysed on a B&D FACSArray flow cytometer. The degree of reduction of MICA binding by preincubation was analysed as MFI (mean fluorescence intensity) of binding with pre-incubation in % of binding of MICA without preincubation.

A more detailed dose-response curve was also performed, analysing the concentrations of recombinantly expressed and purified antibody needed for 50% inhibition (IC50) and full blockade of 1 µg MICA-mFc binding.

Results

Figure 6:
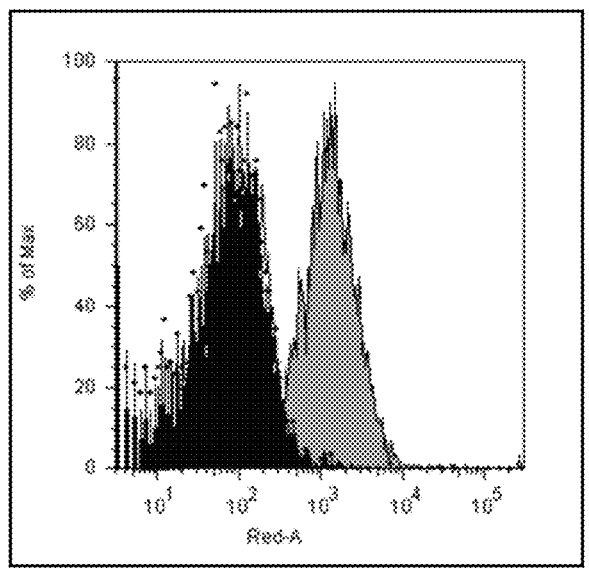
FIG. 6 shows blockade of ligand- (MICA-) binding by an exemplary human anti-NKG2D antibody, demonstrated by blockade of ligand binding by preincubation with antibody in a hybridoma supernatant. The outline represents background, grey represents ligand binding without pre-incubation, and black with dotted line represents ligand binding with preincubation.
Figure 7:
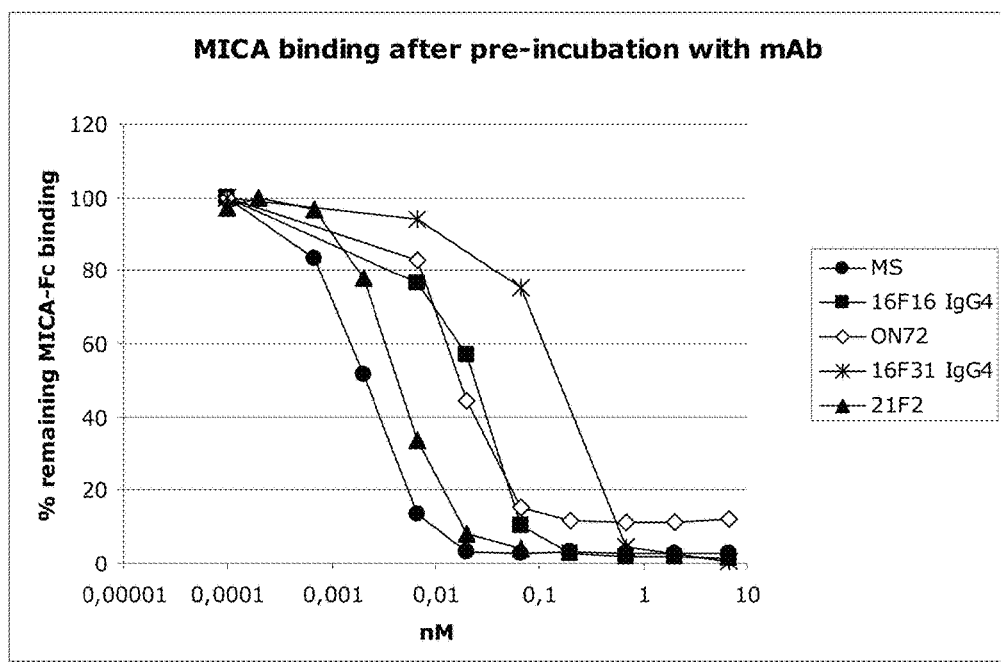
FIG. 7 shows a dose-response curve obtained when analyzing various concentrations of recombinantly expressed and purified fully human anti-hNKG2D antibodies (16F16, 16F31, MS, and 21F2; IgG4 isotype), giving the IC50 and dose needed for full blockade of 1 µg MICA-mFc binding.

The antibodies were analysed for their ability to block ligand binding. FIG. 6 demonstrates that pre-incubation with a hybridoma supernatant virtually blocked all binding of the ligand, MICA. A dose-response curve was performed using recombinantly expressed antibodies, demonstrating IC50 and full blockade of a NKG2D saturating dose of MICA-mFc (1 µg) binding at 0.017 and 0.2 nM 16F16 and at 0.16 and 0.7 nM 16F31 (FIG. 7). The corresponding results for ON72 were 0.02 and 0.24 nM for IC50 and full blockade of 1 µg MI-CA-Fc, respectively. Detailed results are shown in Table 2 below. The IC50 of MS and 21F2 were the lowest, 0.0016 nM and 0.0048 nM, respectively.

TABLE 2

| Antibody | IC50 (µg/ml) | Full blockade of 1 µg MICA-Fc (µg/ml) |
|---|---|---|
| 16F16 | 0.019 | 0.59 |
| 16F31 | 0.24 | 4.8 |
| MS | 0.0025 | 0.053 |
| 21F2 | 0.0063 | 0.16 |
| ON72 | 0.019 | 0.54 |

Example 4: Competition with Murine Antibodies

Materials and Methods

Flow Cytometry Assay—Competition with Murine Antibodies.

For analysis of blockade of commercially available murine anti-hNKG2D antibodies, 50000 NKG2D-expressing cells were incubated in 100 µl final (PBS with 2% FBS at pH7.4) with hybridoma supernatant or purified and recombinantly expressed antibody (at 0.3 µg or as indicated) for 1 h at 16° C., followed by incubation with a murine anti-hNKG2D antibody (ON72, 149810, 1D11 or 5C6 (for 1D11 and 5C6, see, e.g., Bauer et al., Science 1999:285: 727-9 and WO02068615); at 0.3 µg or as indicated) for 30 min at 4° C. The cells were thereafter washed, and secondary Goat-Anti-mouse IgG-HRP Fcγ Fragment specific, Jackson (109-036-151) was added for detection of binding of the murine antibody. The cells were analysed on a B&D FACSArray. This setup was also performed by pre-incubation with murine antibody followed by the hybridoma supernatant or purified human antibody, using secondary Goat-anti-human IgG-HRP Fcγ Fragment specific (Jackson, 109-036-098) for detection. The degree of reduction of binding by pre-incubation was analysed as MFI of binding with pre-incubation in % of binding without pre-incubation.

Results

Figure 8:
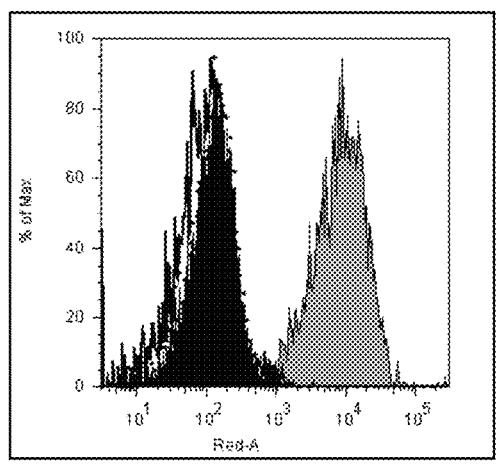
FIG. 8 shows that NKG2D-binding of ON72 to NKG2D was completely prevented by pre-incubation with hybridoma supernatant containing 16F16. Outline represents background, gray represents ON72-binding without pre-incubation, and black dotted represents ON72-binding with pre-incubation.
Figure 9A:
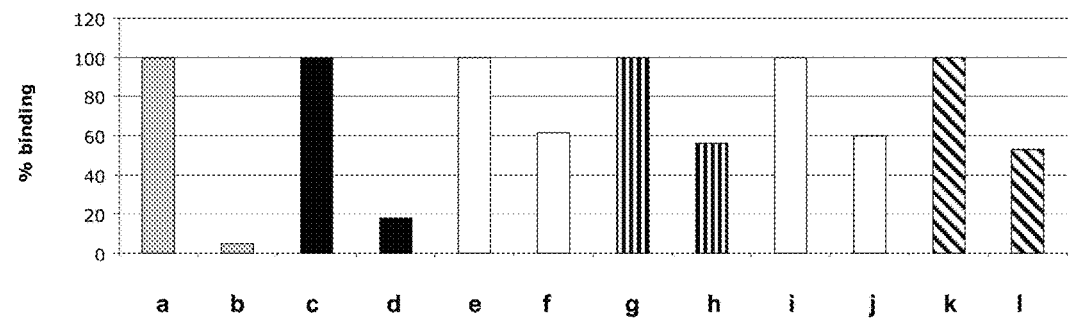
FIGS. 9A-9C shows the capability of fully human anti-hNKG2D antibodies to block the subsequent binding of murine anti-hNKG2D antibodies to NKG2D, or vice versa.
Figure 9B:
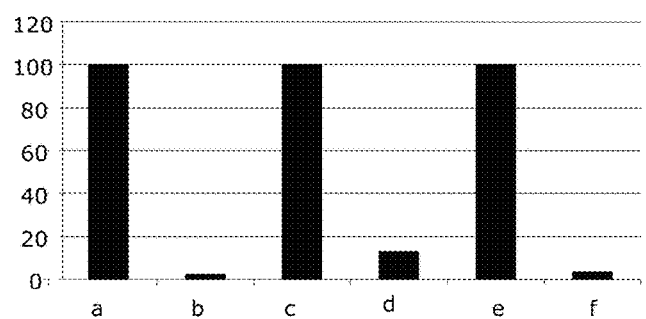
Figure 9C:
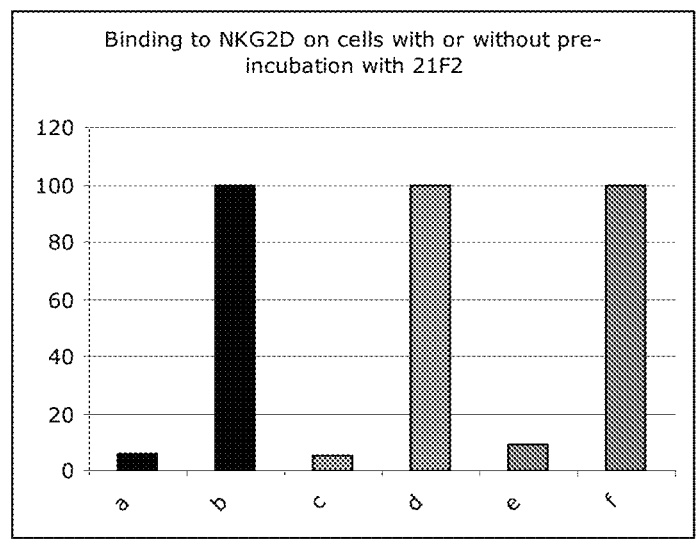

Pre-incubation of cells with a hybridoma supernatant followed by incubation with ON72 demonstrated that 95% of ON72-binding was blocked (FIG. 8). Performing the same type of assay with recombinantly expressed 16F16 antibody demonstrated that 16F16 blocked 95% of ON72 binding, while pre-incubation with ON72 only blocked 82% of subsequent 16F16 binding (FIG. 9A). Likewise, for 149810 and 16F16, only about 50% blockade was observed by either antibody, irrespective of the order of incubation or relative antibody concentration (FIG. 9A). For the other available murine anti-hNKG2D antibodies, cross inhibition is presented in Table 2, demonstrating near full blockade of ON72 by 1D11 and 5C6 and approximately 85% by 149810. Performing the same type of assay with recombinantly expressed MS demonstrated that pre-incubation with MS inhibited 98% of ON72-binding, 88% of 1D11-binding and 96.5% of 149810 binding (FIG. 9B).

TABLE 3

| "Pre-incubation" antibody | "Post-incubation" antibody | Inhibition (%) |
|---|---|---|
| 149810 | ON72 | 85 |
| 1D11 | ON72 | 97 |
| 5C6 | ON72 | 97 |

Example 5: Blood Cell Binding and Cross-Reactivity with Monkey NKG2D

Materials and Methods

Flow Cytometry Assay—Man and Monkey PBMC.

Perifieral blood mononuclear cells (PMBCs) were isolated from humans, or from Cynomologous or Rhesus monkey. All animal work were performed according to Danish National Research Council guidelines. Each PBMC sample was labelled with a marker for the different cellular subsets (NK, CD8+, CD4+ and γδ T cells, as well as for NKG2D, with either ON72 or recombinantly expressed and purified 16F16. The cells were washed and analysed on a BD FACSDiva (BD Biosource) for staining of subsets of cells for NKG2D with the two antibodies. The MFI of the staining was calculated for the individual antibodies.

In a separate experiment, the binding of MS and 21F2 to both PBMC preparations and full blood from healthy volunteers or cynomologous monkey was tested by adding a full dose range of MS or 21F2 followed by detection with anti-human IgG4 antibody, and EC50 values were calculated. Briefly, incubation with antibody was performed at 4° C. for 30 min followed by washing, then directly labelled secondary anti-hIgG4 antibody was added and incubated for 30 min at 4° C. along with antibodies specific for the various cell populations of interest, CD8, CD4, NK and γδ-T cells, then the cells were washed twice in PBS with 2% FCS and the red blood cell lysed. The cells were then analyzed by flow cytometry and binding to the different cell populations assessed.

Results

Results for 16F16 and ON72 are shown in FIGS. 10A-10D. All NK and CD8+ T cells stained positive for NKG2D, whereas no CD4+ T cells stained positive in cynomolgous or rhesus PMBC's. The same results were obtained for human PBMC's that were run in parallel. This agrees with literature, i.e., that in man, NKG2D is normally expressed on NK cells and CD8+ T cells but not on CD4+ T cells.

Staining PBMC's from cynomologous and rhesus monkey with ON72 or 16F16 demonstrated similar binding of the two antibodies to NK cells and CD8+ T cells, but no binding to CD4+ T cells. These results validated the two monkey strains as suitable species for toxicity studies.

No cross-reactivity to mouse, rat, dog or pig NKG2D was observed with either commercially available antibody or any of 16F16 or 16F31.

Figure 11A:
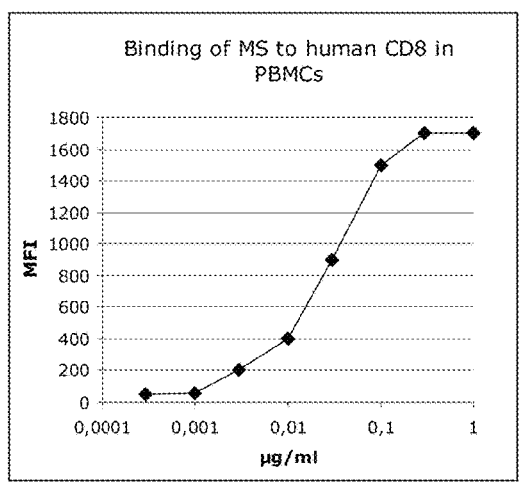
Figure 11B:
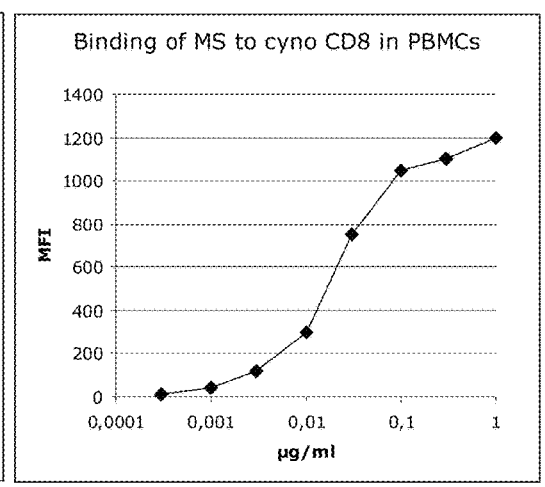

Results for MS binding to human and cynomolgous CD8 T cells are shown in FIGS. 11A and 11B, respectively, and EC50 values for the binding of MS and 21F2 to the PBMC preparations are shown in Table 4, along with the relative EC50 values for cynomolgous to human cells (%). This demonstrates that both MS and 21F2 have very similar affinities to human and cynomologous NKG2D.

TABLE 4

| | EC50 (µg/ml) for MS | | | EC50 (µg/ml) for 21F2 | | |
|---|---|---|---|---|---|---|
| Cell Type | Cyno | Human | % | Cyno | Human | % |
| Gd | 0.0301 | 0.0355 | 85.5 | 0.0464 | 0.0572 | 81.1 |
| CD8 | 0.0286 | 0.0357 | 80.1 | 0.0435 | 0.0605 | 71.9 |
| NK | 0.0309 | 0.0411 | 75.2 | 0.0475 | 0.0712 | 66.7 |

Example 6: Bioassay

To test that the fully human antibodies actually blocked activity of NKG2D, an NKG2D-ligand-driven cytotoxicity assay was developed. A 51Cr-release assay was used, where the target cells were loaded with the radioactive dye and its release measured as a consequence of NK killing of the cell.

Materials and Methods

NKG2D-MICA interaction mediated killing assay. Biological assays for measuring NKG2D-ligand mediated killing of target cells are suitable for testing anti-NKG2D antibodies. The NK cell lines NK92 or NKL (ATCC No. CRL-2407; Robertson et al., Exp Hematol 1996; 24:406-15) both kill MICA-transfected BaF/3 cells in an NKG2D-dependent fashion, and can be used as effector cells, killing 51Cr-loaded target cells expressing an NKG2D-ligand (either MICA, MICB or ULBP1-4).

In a first assay, NKL cells were incubated for 4 h with 51Cr-loaded, MICA-expressing BaF/3 cells in the ratio 10:1, in the presence or absence of 1 or 5 µg ON72 or recombinantly expressed 16F16 of IgG4 isotype. After incubation, the supernatant was transferred to microtiter plates, scintillant added, and the release of 51Cr was measured, as a result of killing of the target cells, in a Topcounter (Wallach). The reduction in release of 51Cr was a measure of inhibition of killing by the added antibody, and the percentage of cells that were killed was calculated.

In a second assay, NK-92 cells was incubated with either $^{51}$Cr-labelled MICA- or ULBP3 expressing BaF/3 cells, and the reduction in killing by addition of increasing concentration of recombinantly expressed and purified 16F16, 16F31, MS, or 21F2 of IgG4 isotype. The results are presented as % inhibition of killing.

Results

Figure 12:
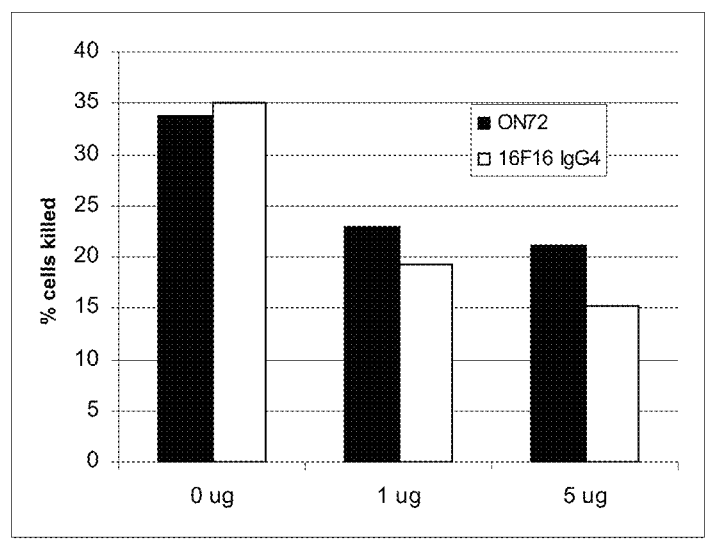
FIG. 12 shows that addition of ligand-blocking antibodies, (ON72 or recombinantly expressed and purified 16F16 (IgG4 isotype)), blocked NK-mediated killing of MICA-expressing target cells in a dose-dependent fashion in a $^{51}$Cr-release assay.

Addition of an ligand blocking antibody, using either ON72 or 16F16, blocked killing of MICA-bearing cells by NKL cells in a dose-dependent fashion, depicted as % inhibition of killing (See FIG. 12). Control cells not expressing MICA were not killed by the NKL cells.

Figure 13A:
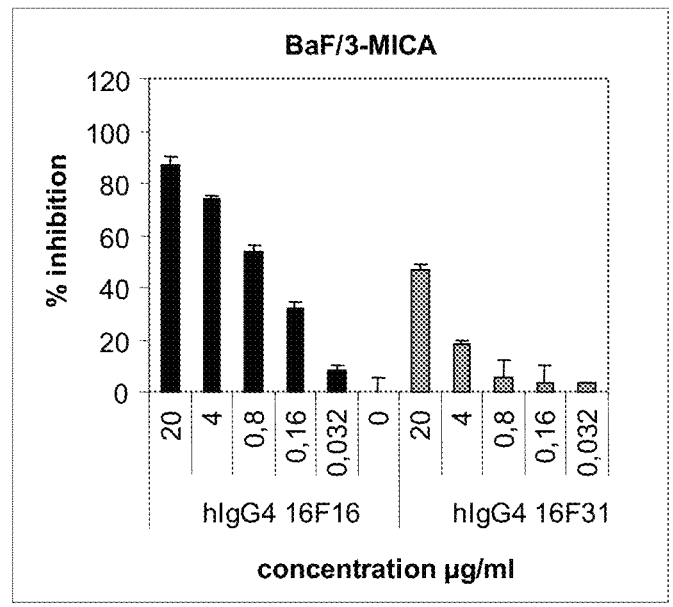
FIGS. 13A and 13B shows that recombinantly expressed and purified 16F16 and 16F31 (both IgG4 isotype) were capable of inhibiting killing of both MICA (FIG. 13A) and ULBP3 (FIG. 13B) bearing target cells (BaF/3) by NK-92 cells in a dose dependent manner, with near total blockade by 16F16 at 0.8 µg/ml for both ligands, and partial blockade by 16F31 at the highest tested dose of 20 µg/ml for both ligands.
Figure 13B:
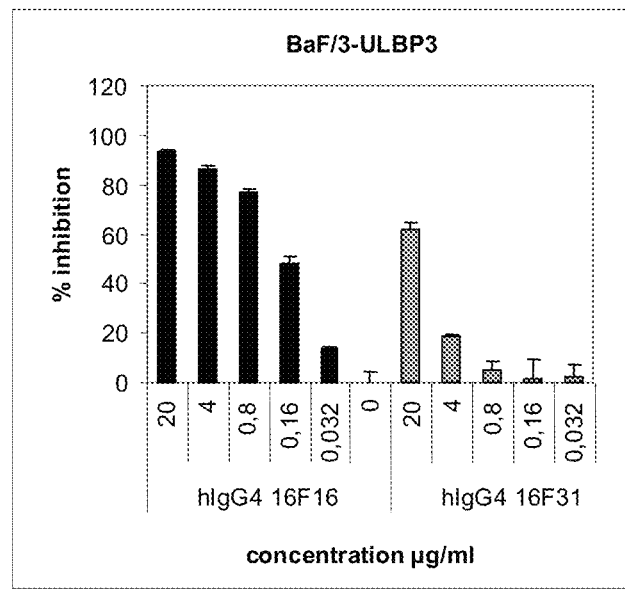

16F16 also inhibited killing of both MICA- and ULBP-bearing BaF/3 target cells by NK-92 cells in a dose dependent manner (FIGS. 13A and 13B), depicted as % inhibition of the killing, with near total blockade at 0.8 µg/ml of both MICA- and ULBP-NKG2D induced killing. 16F31 (IgG4) blocked about 75% of killing at the highest dose tested (20 µg/ml; FIGS. 13A and 13B).

Figure 14A:
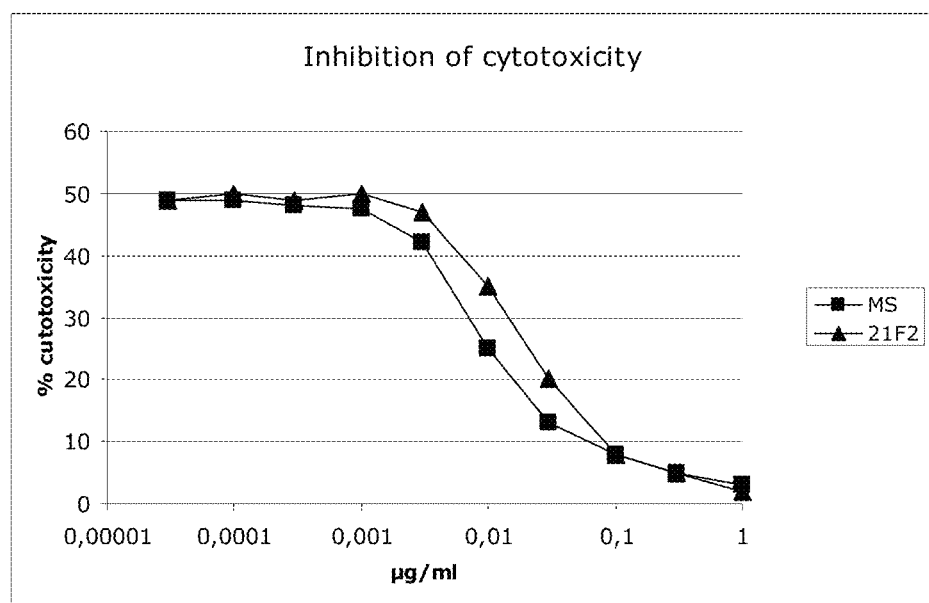
FIGS. 14A and 14B shows that recombinantly expressed and purified MS, 21F2, and 16F16 (all IgG4 isotype) were capable of inhibiting NK-mediated killing of ligand-expressing target cells.
Figure 14B:
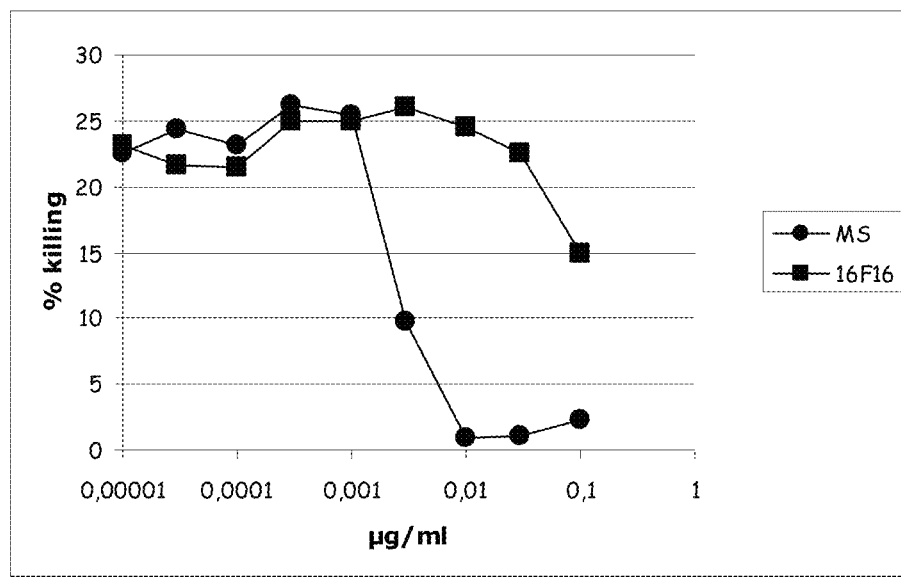

As shown in FIG. 14A, MS and 21F2 both inhibited killing of ULBP3-bearing cells by NK-92 cells in a 51Cr-release assay. In FIG. 14A, blocking of cytotoxicity is depicted as inhibition, with 0 being the two cells incubated together without addition of antibody, with MS being more efficient. As shown in FIG. 14B, maximum inhibition of killing of ligand-(MICA-) bearing cells by NKL cells in a 51Cr-release assay was obtained at a very low concentration of MS (0.01 µg/ml) while the highest tested concentration of 16F16 (0.1 µg/ml) only lead to about 40% inhibition. A summary of IC50 data are provided in Table 5.

TABLE 5

| | EC50 (µg/ml) | |
|---|---|---|
| Antibody | ULPB3-expressing target cells | MICA-expressing target cells |
| 16F16 | 0.35 | 0.14 |
| 16F31 | 14.8 | 14.9 |
| MS | 0.012 | 0.0016 |
| 21F2 | 0.021 | |
| ON72 | 0.065 | |

Example 7: Antibody-Induced NKG2D Downmodulation

When hNKG2D expressing cells are incubated with antibody, down-modulation, e.g., via internalization, of NKG2D was shown to occur in a similar manner previously demonstrated for certain anti-mNKG2D antibodies in mouse models. This will lead to a different mode of action, and, possibly, a longer effect-time of the antibody. Here, down-modulation was analysed by measuring how much the NKG2D level decreased after overnight incubation with antibody.

Materials and Methods

Flow Cytometry Assay—Down-Modulation.

Antibody-mediated down-modulation of NKG2D was analysed on different types of NKG2D-expressing cells by incubation overnight with ON72, 16F16, 16F31, MS, or 21F2. Without being limited to theory, differences in down-modulation can reflect differences in antigen-interaction, e.g., epitope. The human antibodies were recombinantly expressed as IgG4 isotype, which isotype binds the Fc-receptor with low affinity.

In a first experiment, 1 mL containing 1 µg of ON72 or 16F16; 3 µg 16F31; 0.1 µg MS, or 0.3 or 1 µg 21F2, was added to NKG2D- and DAP10-expressing cells.

In a second experiment, freshly prepared NK cells were incubated with different amounts of MS (0; 0.003; 0.01; 0.03; 0.1; 0.3; 1 µg) or 21F2 (0.1 µg) in the presence of 10% human serum to mimic the situation in full blood, with the presence of IgGs with higher affinity for the Fc receptors.

In a third experiment, 0.1 µg/ml MS, ON72, or 21F2 was added to whole blood containing NK, CD8+, and γδ T cells. After incubation, staining with anti-CD8, anti-CD56 (NK cells), anti-γδ, and anti-human antibody identified binding to the various subtypes As controls in the above experiments, cells were left untreated at 37° C. overnight. The next day, both untreated and antibody-treated cells were incubated with 0.1 µg of the pre-treatment antibody, followed by either Goat-Anti-mouse IgG-HRP Fcγ Fragment specific, Jackson (109-036-151) for detecting ON72, or Goat-Anti-human IgG-HRP Fcγ Fragment specific, Jackson (109-036-098) for detecting human antibody. The cells were then washed and analyzed on a B&D FACSArray. The difference in staining between untreated and antibody-treated staining levels was analyzed as a measure of NKG2D down-modulation, and the % remaining cell surface NKG2D was calculated as % staining after pre-treatment compared to staining of untreated cells.

Results

As shown in FIG. 15, ON72, 16F16, and 16F31 all induced NKG2D downmodulation in NKG2D-expressing BAF/3 cells. For ON72 and 16F31, approximately 55% down-modulation was observed, as compared to about 75% down-modulation using 16F16. This suggests that 16F16 induces down-modulation more effectively, as it has a similar Kd value to that of ON72. Without being limited to theory, this might be due to different binding epitopes. After incubation with MS, there was about 95% reduction in surface NKG2D (FIG. 16A). In freshly isolated NK cells, an MS concentration corresponding only to about 60% of saturation (0.03 µg/ml) induced maximum internalization of cell-surface NKG2D in the presence of serum, with, in this case, only about 35% NKG2D available for binding after overnight incubation with antibody (FIG. 16B). For 21F2, in the absence of serum, a concentration of 1 µg/mL induced 78% (FIG. 17) downmodulation of NKG2D.

Figure 18A:
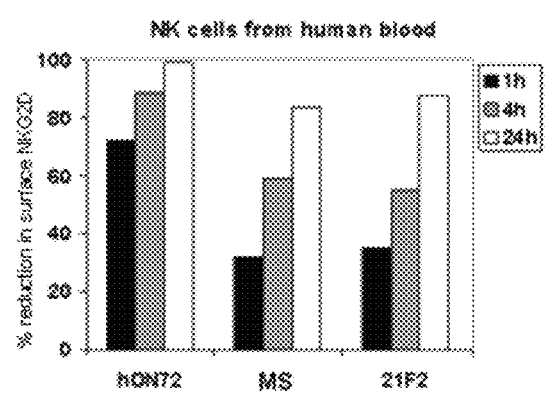
FIGS. 18A, 18B and 18C show the effect of ON72, MS, and 21F2 on surface-presented NKG2D in different types of cells in human blood samples, at the indicated time points. The concentration of each antibody was 0.1 µg/ml. While not being limited to theory, the reduction of surface-presented NKG2D in the experiments likely represents NKG2D internalization. Figures (FIG. 18A) to (FIG. 18C) shows antibody-induced NKG2D internalization of NKG2D-expressing NK cells, CD8+ T cells, and δγ T cells, respectively. MS and 21F2 resulted in less reduction of surface-associated NKG2D than ON72.
Figure 18B:
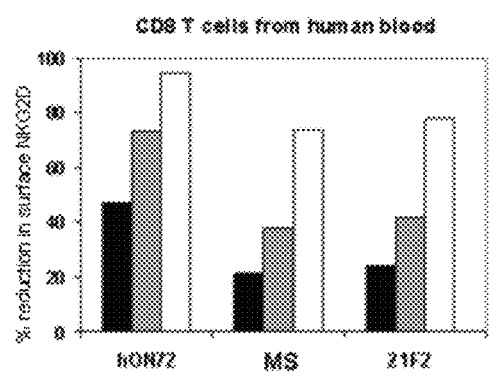
Figure 18C:
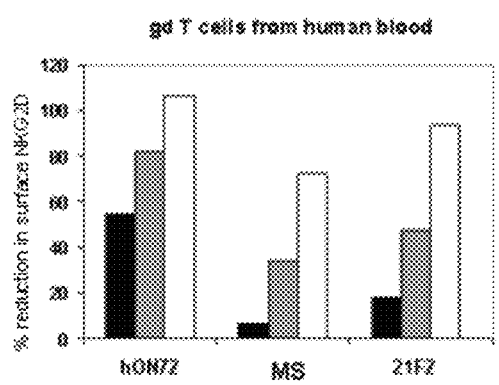

In 3 different populations of NKG2D+ lymphocytes in whole blood, for MS and 21F2 approximately 80% internalization was observed at 24 h, whereas ON72 induced internalization to nearly 100% (FIGS. 18A, 18B and 18C). Additionally, ON72 induced internalization faster than MS and 21F2 (FIGS. 18A, 18B and 18C), reaching 50-75% in 1 h.

Example 8: Non-Depleting IgG4 Versions of Human Antibodies

Antibodies cross-linking cells in blood may induce depletion of the antibody-bound cells. However, the affinity of IgG4 antibodies to the activating Fc-receptors is so low compared to that of IgG1 that IgG4 antibodies do not lead to depletion.

Materials and Methods
Whole Blood Cell Depletion Assay.

To demonstrate non-depletion of NKG2D-expressing cells, whole human blood is incubated with 1 μg of IgG4-versions of human antibodies for 4 hours, and the relative distribution of NKG2D-positive and NKG2D-negative cells analyzed and compared to whole human blood incubated in the absence of antibody. The analysis described in Example 4 can then be used for evaluation.

Example 9: Affinity Determination

Surface plasmon resonance measurements were performed on a Biacore 1000 upgrade apparatus (Biacore GE Healthcare; Biacore Upgrade CA0396) at 25° C. In all Biacore experiments HBS-EP buffer (Biacore GE Healthcare; BR-1001-88) served as running buffer and sensorgrams were analyzed with Biaevaluation 4.1 software.

Protein Immobilisation.

Recombinant MICA-Fc proteins were obtained from R&D systems or were recombinantly produced. Recombinant ULBP-1, 2, 3, MICB and NKG2D-Fc were purchased from R&D systems. Recombinant NKG2D-Fc proteins were immobilized covalently to carboxyl groups in the dextran layer on a Sensor Chip CM5 (Biacore GE Healthcare; BR-1000-14). The sensor chip surface was activated with EDC/NHS (N-ethyl-N'-(3-dimethylaminopropyl) carbodi-imidehydrochloride and N-hydroxysuccinimide (Biacore GE Healthcare; BR-1000-50)). Proteins were diluted to 10 μg/ml in coupling buffer (10 mM acetate, pH 5.2) and injected until the appropriate immobilization level was reached (i.e. 500 to 1000 RU). Deactivation of the remaining activated groups was performed using 100 mM ethanolamine pH 8 (Biacore GE Healthcare; BR-1000-50).

Affinity Measurement.

Human antibodies 16F16, 16F31, MS, and 21F2, both recombinantly expressed as IgG4 isotype, were compared to murine antibody ON72. For kinetic experiments, serial dilutions of soluble antibodies (from 0.3 to 30 nanoM) were injected for 2 min at a constant flow rate of 40 μl/min on dextran layers containing immobilized NKG2D-Fc proteins (500 to 1000 RU), and allowed to dissociate for 3 min before regeneration by a eight second injection of 500 mM NaCl and 10 mM NaOH buffer. The resulting sensorgrams were analysed by global fitting using the Langmuir model. The dissociation constant (KD) was calculated as KD=kd/ka.

Affinity on Cellular Membrane-Situated NKG2D.

Full dose-response curves for binding of antibody to cells expressing NKG2D were performed to analyze binding affinity to the naturally occurring receptor.

Results

The affinity determination results for 16F16 is shown in Table 6A, at two different NKG2D-densities on the chip in the Biacore, demonstrating high affinity (KD 1.72 E-10M) and slow off rate (kd 3.7 E-5/s). ON72 was similar, with a ka=9.6E5/(M*s); kd=1.1E-4/s; and KD=1.7E-10M. Both MS and 21F2, however, had a higher affinity (KD 2.52 E-12M and 7.79 E-11M, respectively), and MS had a slower off-rate (kd 1.45 E-05/s) (Table 6B).

Figure 3:
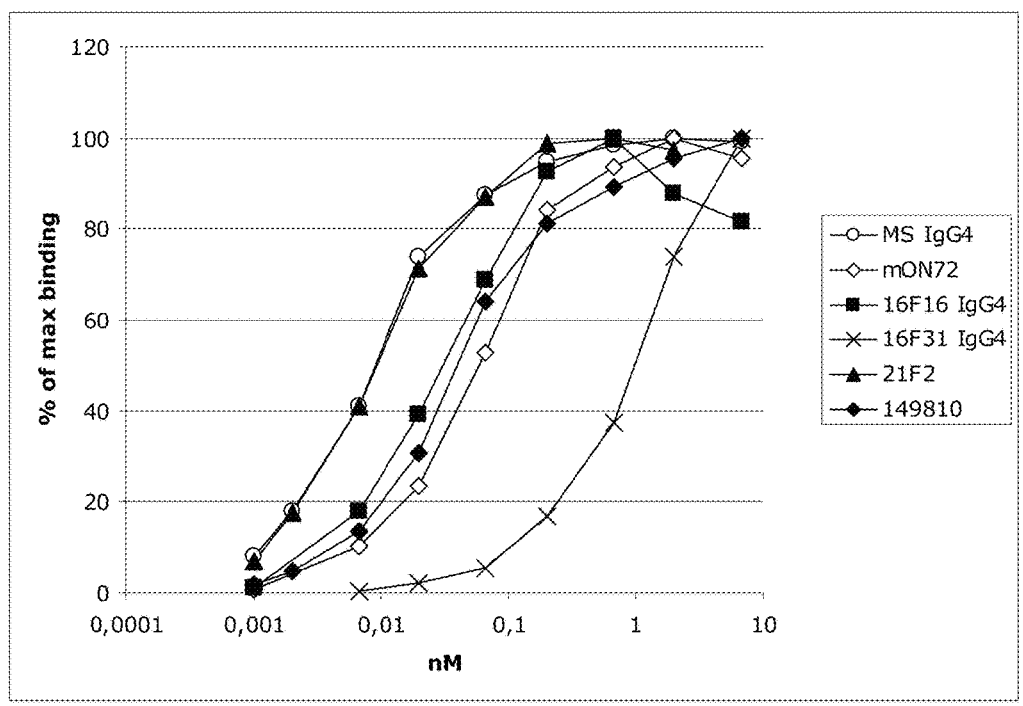
FIG. 3 demonstrates dose-response of NKG2D-binding to NKG2D-expressing cells of recombinantly expressed and purified fully human IgG4 antibodies (16F16, 16F31, MS, and 21F2) as compared to commercial murine antibodies (ON72 and 149810).

FIG. 3 demonstrates dose-dependent NKG2D binding of recombinantly produced and purified human antibodies 16F16, 16F31, MS and 21F2 to NKG2D- and DAP10-expressing BaF/3 cells, as compared to commercially available murine antibodies (ON72 and 149810), using flow cytometry. The EC50 values for binding were as follows:
16F16: 0.051 μg/ml (0.034 nM)
16F31: 0.31 μg/ml (0.21 nM)
MS: 0.032 μg/ml (0.021 nM)
21F2: 0.033 μg/ml (0.023 nM)
ON72: 0.062 μg/ml (0.048 nM)
149810: 0.063 μg/ml (0.042 nM).

TABLE 6A

Biacore analysis of 16F16 NKG2D-binding

| NKG2D density (RU) | Ka (M(-1)s(-1)) | Kd (s(-1)) | Rmax | KD (M) | Chi | Fi |
|---|---|---|---|---|---|---|
| 1200 | 2.08E+05 | 3.71E-05 | 1.61E+03 | 1.78E-10 | 0.56 | v. good |
| 600 | 4.19E+05 | 6.91E-05 | 657 | 1.65E-10 | 0.43 | v. good |
| | Mean ± SD | | | (1.72E-10 ± 9.19E-12) M | | |

TABLE 6B

Biacore analysis of MS and 21F2 NKG2D-binding

| NKG2D density (RU) | Ka (1/Ms) | Kd (1/s) | KD (M) | Rmax (RU) | Chi$^2$ (RU$^2$) | fit |
|---|---|---|---|---|---|---|
| MS - 350 | 5.75+0E6 | 1.45E-05 | 2.52E-12 | 89.7 | 2.9 | v. good |
| 21F2 - 400 | 1.85E+06 | 1.44E-04 | 7.79E-11 | 112.3 | 1.42 | v. good |

Example 10: Agonist Activity of Immobilized Anti-NKG2D Antibodies

To analyse antibody agonistic activity, proliferation of peripheral blood lymphocytes (PBMCs) stimulated with low levels of CD3 was assessed in the presence or absence of immobilized anti-NKG2D antibody, using CD28 as control. The stimulation was done under circumstances where NKG2D have been shown to act as a co-stimulatory molecule (Mashoo et al, Immunol. 2005; 174; 4480-4484), believed to reflect the triggering of NKG2D in the presence of pro-inflammatory cytokines as under chronic inflammatory conditions. In this assay, PBMCs were stimulated for 3 days with surface bound antibodies, followed by 4 days of IL-2 stimulation, and the proliferation assessed by CFSE dilution in either all lymfocytes, CD8+, or CD4+ T cells.

Materials and Methods
PBMC Proliferation Assay.

PBMCs were purified by gradient centrifugation. Ninety-six-well Maxisorp plates were coated with anti-Fc antibody (Jackson—Immuno Research 115-006-008), then washed and followed by addition of anti-CD3 (0.1 or 0.3 ng/ml, Bioscience cat #14-0037-82), anti-NKG2D (MS or ON72, 0.2 µg/ml) and/or anti-CD28 antibody (0.2 µg/ml, Becton Dickison cat #348040). One hundred-and-fifty thousand PBMCs were added to each well, and the cells incubated at 37° C. for 3 days. The cells were thereafter labelled with CFSE (molecular probes cat #C34554). Ten million cells were incubated in 0.5 ml 1 µM CFSE for 10 min at 37° C., followed by a wash, and 150.000 PBMCs per well in 60-well plates were incubated for 4 days with IL-2 (10 U/ml). Finally, the cells were stained with anti-CD8 and anti-CD4 antibody and the proliferation measured by CFSE dilution in either all lymphocytes (total presented in FIGS. 19A and 19B) or CD8+ or CD4+ T cells (similar results obtained)

Results

As shown in FIGS. 19A and 19B, MS did not significantly co-stimulate proliferation of lymphocytes at either 0.1 or 0.3 ng/ml CD3 stimulation, whereas ON72 resulted in a small but significant co-stimulation at both CD3 concentrations. See Table 7. In both cases the control, anti-CD28, gave strong co-stimulation, and anti-NKG2D did not add significantly to this. This shows that there is a difference in binding mode of the two antibodies, with immobilized ON72 having detectable agonistic activity, whereas MS is a more pure antagonist.

TABLE 7

Results from PBMC proliferation assay

| Stimulation | % proliferation | SEM |
| --- | --- | --- |
| CD3 0.1 | 2.82 | 0.39 |
| CD3 0.1 + MS | 3.60 | 0.65 |
| CD3 0.1 + ON72 | 7.12 | 1.35 |
| CD3 0.1 + CD28 | 24.53 | 4.71 |
| CD3 0.1 + CD28 + MS | 21.64 | 7.59 |
| CD3 0.1 + CD28 + ON72 | 22.86 | 6.09 |
| CD3 0.3 | 15.80 | 5.30 |
| CD3 0.3 + MS | 17.32 | 4.41 |
| CD3 0.3 + ON72 | 28.38 | 7.00 |
| CD3 0.3 + CD28 | 39.90 | 6.91 |
| CD3 0.3 + CD28 + MS | 46.08 | 5.71 |
| CD3 0.3 + CD28 + ON72 | 40.12 | 7.93 |

Example 11: Crystal Structure of Soluble hNKG2D in Complex with MS-Fab

The crystal structure of a soluble fragment of hNKG2D in complex with a Fab fragment of the human monoclonal antibody MS was solved and refined to 1.7 Å resolution with X-ray crystallography. The results confirmed that the antibody, when bound to hNKG2D, blocks the binding of a MICA molecule (FIGS. 20A, 20B and 20C-22A-22D). It was also shown that each hNKG2D dimer bound only one MS Fab fragment. The MS Fab portion bound primarily to one of the two hNKG2D monomers ("NKG2D monomer unit 1"), but, although it only interacted weakly with the other monomer ("NKG2D monomer unit 2"), any further MS Fab was blocked from binding monomer unit 2.

A list of literature referred to in this Example is provided in Example 12.

Materials and Methods

Soluble hNKG2D (residues 89-216 of SEQ ID NO:2) and MS Fab (comprising a light chain corresponding to SEQ ID NO:41 and a heavy chain fragment corresponding to residues 1-213 of SEQ ID NO: 40) were mixed with a slight molar excess of hNKG2D and the complex was purified on a gel-filtration column. The complex was then concentrated to about 9.5 mg/ml. Crystals were grown with the hanging drop-technique in 17% PEG3350, 200 mM sodium malonate and 100 mM bis-tris-propane buffer with a pH of 7.5. Crystals were transferred to a cryo-solution containing 75% of the precipitant solution and 25% of glycerole. The crystal was allowed to soak for about 15 seconds. The crystal was then flash frozen in liquid $N_2$ and kept at 100 K during data collection by a cryogenic $N_2$ gas stream. Crystallographic data were collected, originally to 2.4 Å resolution at a Rigaku 007HF rotating anode source and thereafter, using a new crystal, to 1.7 Å resolution at beam-line BL911-3(2) at MAX-lab, Lund, Sweden. Space group determination, integration and scaling of the data were made in the XDS software package(3). Cell parameters for the synchrotron data were determined to be 82.1, 54.2, 169.4 Å, 90°, 102.62° and 90°, respectively. Molecular replacement, using the MOLREP(4) and PHASER software program(5; 6) of the CCP4 suite(7), a Fab molecule from the PDB-deposited(8) structure 1L71(9) and a hNKG2D molecule from the deposited 1MPU structure(10), were used for structure determination. The Fab molecule was divided into two domains, the variable and the constant domains, and for the NKG2D a monomer was used as a search model in the molecular replacement calculations. Crystallographic refinements, using the REFMACS software program(11), was followed by computer graphics inspection of the electron density maps, model corrections and building using the Coot software program (12). The procedure was cycled until no further significant improvements in could be made to the model. The structure was originally interpreted in the C2 space group, using the rotating anode data. With the synchrotron data XDS(3) indicated a non-centric monoclinic space group though and data were integrated in space group P2, later changed to $P2_1$. A C-centered orthorhombic cell did also score highly. Also the POINTLESS software(13) proposed the $P2_1$ as the correct space group when testing the synchrotron data. The PHASER software program was used for a new round of molecular replacement, using the preliminary models prepared in the first round of molecular replacement in the C2 space group. Molecular replacement run successfully but as R- and R-free values (a comparisons of observed experimental data with, from the model, calculated data) during refinements did not decrease as expected (R- and R-Free of 0.35 and 0.43), despite reasonable electron density maps, further investigations of the data and refinements were started. Different space groups were tested, including P1, but did not improve the refinements. Instead data was inspected for twinning and data was transferred to the SHELXL refinement software program(14). Using a twin relation-ship of (h,k,l)→(h,k,−h−l) the R- and R-free for all data dropped from 0.34 and 0.40 to 0.30 and 0.34, respectively, and with a refined twinning factor, BASF, of 0.25. Manual modifications to the model were made with the COOT graphics software program. Refinement was carried out in the SHELXL computer program. Final R- and R-free for all data, with no cut-offs, after 14 cycles of manual intervention and following refinements were 0.277 and 0.320, respectively, and the model showed a root-mean-square deviation (RMSD) from ideal bond lengths of 0.008 Å (Table 8). The refined twinning factor was calculated by SHELXL to be 0.26.

Results

As shown in FIGS. 20A, 20B, 21A, and 21C, MS-Fab effectively blocks MICA binding to both monomers of the hNKG2D dimer. However, while the MICA molecule bound to both monomers of the NKG2D dimer(1), the MS Fab bound primarily to one of the two monomers, herein denoted "NKG2D monomer unit 1" (FIGS. 21A and 21C). The interactions between MS and NKG2D monomer unit 2 were found to be less specific (e.g., comprise no or fewer hydrogen-bonds), and less important in keeping the MS Fab/NKG2D complex together.

Calculation by the software program AREAIMOL of the CCP4 program suite(7) of the average areas excluded in pair-wise interactions gave for the two independent soluble hNKG2D/MS-Fab molecular complexes of the determined crystals structure totally 909 and 876 Å$^2$, respectively. The average areas excluded in pair-wise interaction between NKG2D monomer unit 1 and MS Fab were calculated to be, for the two independent complexes, 710 and 736 Å$^2$, respectively. The excluded areas for the other monomer ("NKG2D monomer unit 2") were substantially smaller, 227 and 158 Å$^2$, respectively.

The direct contacts between the hNKG2D and MS Fab were identified by running the CONTACTS software of the CCP4 program suite(7) using a cut-off distance of 4.0 Å between the MS-Fab and the hNKG2D molecules. The results for the two independent soluble hNKG2D/MS-Fab complex molecules of the crystal structure are shown in Tables 9-12. The resulting hNKG2D epitope for MS was found to comprise the following residues of hNKG2D (SEQ ID NO: 2): Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 (FIG. 21A). In NKG2D monomer unit 2, only 5 interactions were found, and only one residue (Tyr 152) was present in both of the crystallographically independent complexes. Further, the Lys 150 side chain atom Nζ was only involved in hydrogen-binding in one of the complexes, and the remaining interactions were of weaker polar and hydrophobic type.

Figure 20A:
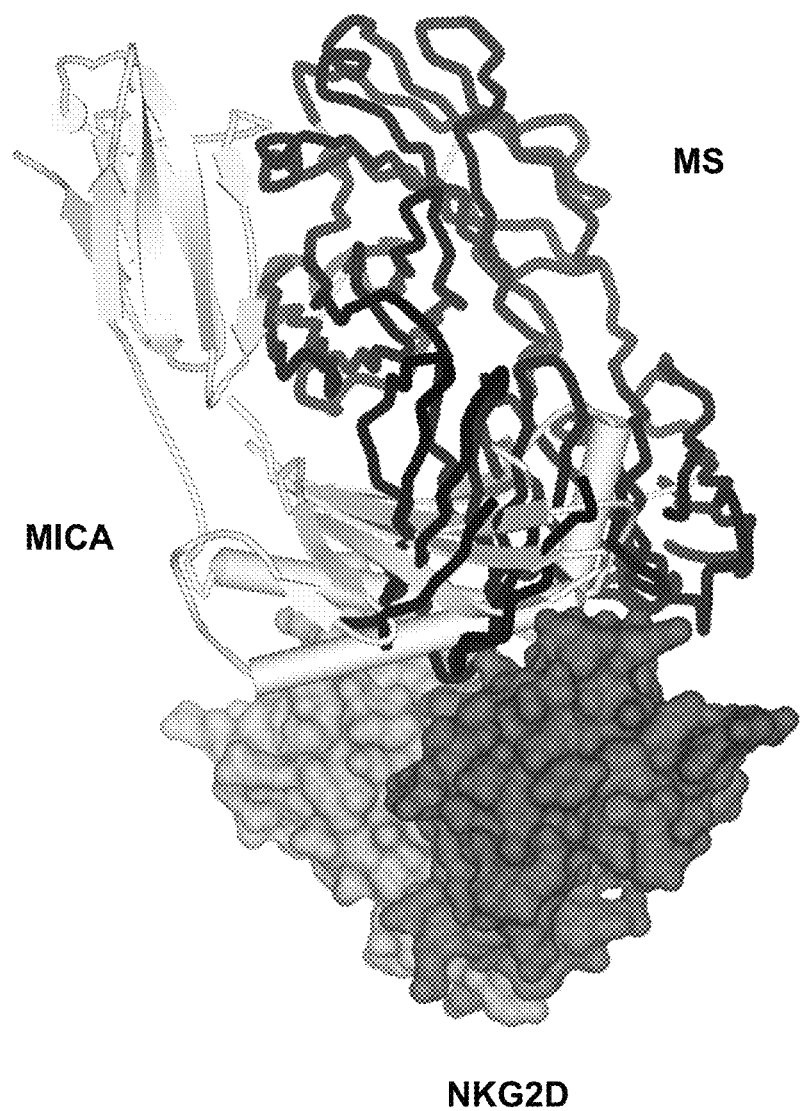
FIGS. 20A, 20B and 20C depicts 3-dimensional superimposed representations of hNKG2D dimer complexed with Fab-fragment(s) of anti-NKG2D antibody (MS or hzON72) or with MICA ligand. The hNKG2D homodimer ('NKG2D') is shown in a surface representation with one of the monomers in a darker color than the other. The Fab fragments ('MS' and 'hzON72', respectively) are indicated in black tube style while the MICA ('MICA') is indicated in a light schematic secondary structure representation style.
Figure 20B:
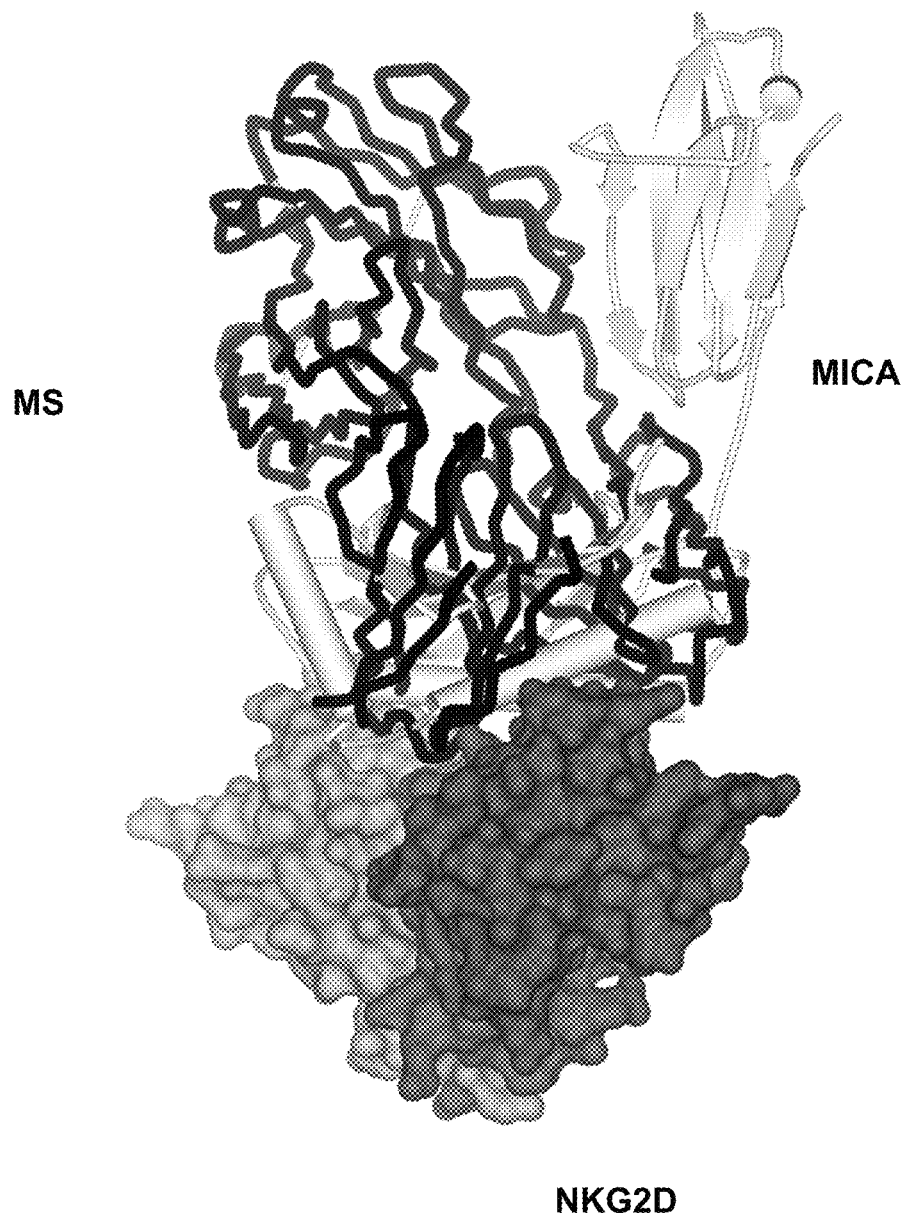

The MS hNKG2D epitope comprised residues located in the loop just before and the beginning of β-strand β3'(1), Lys 150-Tyr 152; in β5' and the loop after, Thr 180-Gln 185; in β5, Leu 191; in β6, Lys 197, Tyr 199 and Glu 201; and in the loop preceding and in the β7 strand, Thr 205-Thr 208. These contact areas agreed very well with what have been reported as the binding site for MICA on hNKG2D (1). MICA binds asymmetrically to the symmetric homodimer of NKG2D(10). This is also the case for the MS Fab binding to hNKG2D. Therefore, there will be two possible binding orientations to NKG2D for MS Fab relative to MICA. This is shown in FIG. 20A, B and FIG. 22, where it is clearly seen that the MS Fab blocks both possible MICA relative binding orientations.

The MS paratope for hNKG2D included residues Tyr 33 and Trp 97 of the MS light (L) chain (SEQ ID NO: 41, Tables 9-12), and residues Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the heavy (H) chain (SEQ ID NO: 40, Tables 9-12). The hNKG2D epitope, and the residues involved in hydrogen-binding, are also indicated in the amino-acid sequence of hNKG2D in FIG. 21A.

Example 12: Crystal Structure of Soluble hNKG2D in Complex with hzON72-Fab

The crystal structure of soluble hNKG2D in complex with a humanized version of ON72 Fab fragment (hzON72) was solved and refined to 3.15 Å resolution with the use of X-ray crystallography. The results confirmed that the antibody, when bound to hNKG2D, will be able to block binding of MICA molecules to hNKG2D (FIGS. 20A, 20B and 20C-22A-22D). It was also shown that each hNKG2D dimer can bind two hzON72 Fab portions simultaneously.

A list of literature referred to in this Example is provided at the end of the Example.

Materials and Methods

A soluble hNKG2D fragment (corresponding to residues 81-216 of SEQ ID NO:2) and hzON72 Fab (SEQ ID NO:70 and SEQ ID NO:71, heavy chain fragment and light chain, respectively) were mixed with a slight molar excess of hNKG2D and the complex was purified on a gel-filtration column. The complex was then concentrated to about 7.5 mg/ml. Crystals were grown with the hanging drop-technique in 1M LiSO$_4$ and 100 mM MES buffer pH 6.5. Crystals were transferred to a cryo-solution containing 75% of the precipitant solution and 25% of glycerole. The crystal was allowed to soak for about 15 seconds. The crystal was then flash frozen in liquid N$_2$ and kept at 100 K during data collection by a cryogenic N$_2$ gas stream. Crystallographic data to 3.15 Å resolution were collected using beam-line BL911-5(2) at MAX-lab, Lund, Sweden. Space group determination, integration and scaling of the data were made in the XDS software package(3). Cell parameters were determined to be 65.7, 93.3, 128.9 Å, 90°, 93.83° and 90°, respectively. Space group was determined to be P2$_1$ with space for one NKG2D dimer and two hzON72 Fab molecules, in the asymmetric unit. Molecular replacement, using the MOLREP(4) software program of the CCP4 suite(7) and the Fab molecule of the PDB-deposited(8) structure 1UJ3(15), and the hNKG2D dimer of the deposited 1MPU structure(10), were used for structure determination. The Fab molecule was first tested in rotation function runs with different elbow angles from which the Fab with the highest scoring was picked. NKG2D was searched for as a dimer in the molecular replacement calculations. Crystallographic refinements, using non-crystallographic restraints between the two hNKG2D monomers and between the two Fab molecules, were made in the REFMACS software program(11) of the CCP4 program suite(7). The crystallographic refinement was followed by computer graphics inspection of the electron density maps, model corrections and building using the Coot software program (12). The procedure was cycled until no further significant improvements in could be made to the model. Final R- and R-free for all data were 0.216 and 0.268, respectively, and the model showed a root-mean-square deviation (RMSD) from ideal bond lengths of 0.012 Å (Table 13).

Results

Figure 20C:
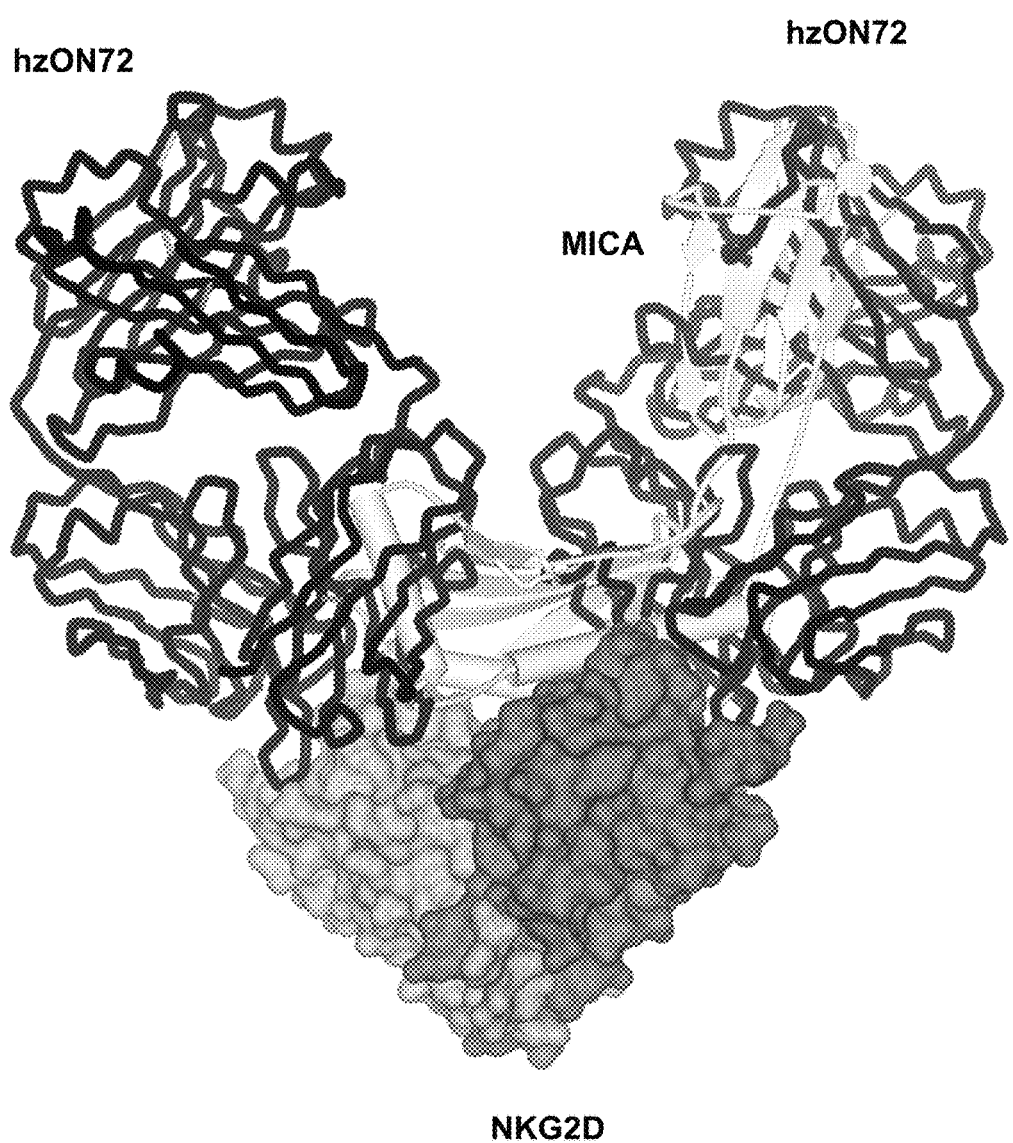
Figure 22A:
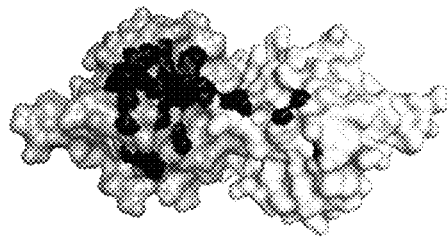
FIGS. 22A-22D shows the hNKG2D molecules in surface representations with one of the monomers slightly darker than the other. The NKG2D atoms within 4.0 Å distance from their respective crystals structures MS/hzON72/MICA Fab atoms are colored in black and are shown for the MS Fab (FIG. 22A), 2 hzON72 Fabs (FIG. 22B) and, for MICA, (FIG. 22C) and (FIG. 22D). As both MICA and MS Fab bind to the NKG2D dimer in an asymmetric manner, the relative binding orientation to NKG2D can differ. This is indicated in the figure which shows the two possible relative binding orientations of MICA in (FIG. 22C) and (FIG. 22D) to MS. See also Tables 9-12 and 14-15.
Figure 22B:
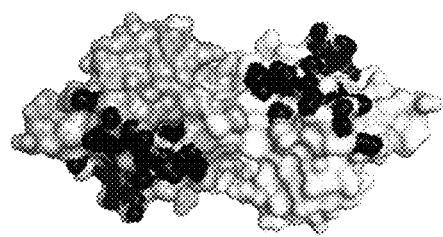
Figure 22C:
Figure 22D:
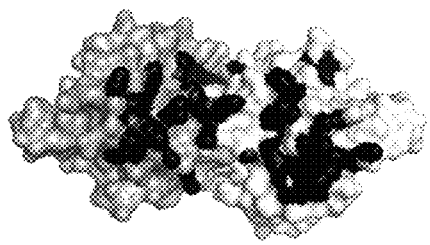

A MICA molecule binds strongly to both monomers of NKG2D(1), but two hzON72-Fab molecules instead bound independently to each of the hNKG2D monomers, effectively blocking MICA binding to the NKG2D dimer (FIGS. 20C, 21B, C and 22A-22D). Calculation by the software program AREAIMOL of the CCP4 program suite(7) of the average areas excluded in pair-wise interactions gave for the two crystallographically independent soluble hNKG2D/hzON72-Fab molecular complexes (one hzON72 Fab molecule in complex with one hNKG2D monomer) in the determined crystals structure a total of 791 and 801 Å$^2$, respectively. The average areas excluded in pair-wise interaction between the soluble hNKG2D monomers and the heavy chains of hzON72-Fab were calculated to be, for the two crystallographically independent complexes, 642 and 631 Å$^2$, respectively, while for the light chains 208 and 242 Å$^2$, respectively.

The direct contacts between the hNKG2D to hzON72-Fab were identified by running the CONTACTS software of the CCP4 program suite using a cut-off distance of 4.0 Å between the hzON72-Fab and the hNKG2D molecules. The results for the two independent soluble hNKG2D/hzON72-Fab molecules of the crystal structure are shown in Tables 14-15. The resulting hNKG2D epitope for hzON72 was found to comprise the following residues of hNKG2D (SEQ ID NO: 2): Ser 165, Trp 166, Leu 174, Ser 175, Pro 176, Asn 177, Leu 179, Thr 180, Ile 181, Ile 182, Glu 183, Met 184, Lys 186, Ala 193, Ser 194, Ser 195, Lys 197 and Tyr 199. The hzON72 paratope for hNKG2D included residues Tyr 1, Lys 92, Thr 93 and Leu 94 of the hzON72 light (L) chain (SEQ ID NO:71, Table 14-15), and residues Trp 33, Asp 52, Asp 55, Tyr 57, Asn 59, Tyr 60, Tyr 101, Asp 102, Gly 103, Tyr 104, Tyr 105 and Val 106 of the hzON72 heavy (H) chain (SEQ ID NO:70) The hNKG2D epitope for hzON72, and the residues involved in hydrogen-binding, are also indicated in the amino-acid sequence of hNKG2D in FIG. 21B.

The hNKG2D epitope was comprised of residues located in the beginning of β-strand β4(1), Ser 165-Trp 166; in the loop before β5', Leu 174-Asn 177; in the β5' strand and the loop thereafter, Leu 179-Lys 186; the loop before β6, Ala 193-Ser 195; and in the β6 strand, Lys 197 and Tyr 199. These contact areas agreed very well with what have been reported as the binding site for MICA on hNKG2D(1) and it was clear that hzON72 antibody can block the MICA binding. This is shown in FIGS. 20C, 21B, C and 22A-22D.

TABLE 8

Results from the X-ray model refinement to the observed data of the NKG2D/MS-Fab complex by the software program SHELXL(14).

| REMARK | 2 | RESOLUTION. 1.70 ANGSTROMS. | |
|---|---|---|---|
| REMARK | 3 | | |
| REMARK | 3 | REFINEMENT. | |
| REMARK | 3 | PROGRAM: SHELXL-97 | |
| REMARK | 3 | AUTHORS: G. M. SHELDRICK | |
| REMARK | 3 | | |
| REMARK | 3 | DATA USED IN REFINEMENT. | |
| REMARK | 3 | RESOLUTION RANGE HIGH (ANGSTROMS): | 1.70 |
| REMARK | 3 | RESOLUTION RANGE LOW (ANGSTROMS): | 10.00 |
| REMARK | 3 | DATA CUTOFF (SIGMA(F)): | 0.0 |
| REMARK | 3 | COMPLETENESS FOR RANGE (%): | 92.1 |
| REMARK | 3 | CROSS-VALIDATION METHOD: | FREE R |
| REMARK | 3 | FREE R VALUE TEST SET SELECTION: | RANDOM |
| REMARK | 3 | | |
| REMARK | 3 | FIT TO DATA USED IN REFINEMENT (NO CUTOFF). | |
| REMARK | 3 | R VALUE (WORKING + TEST SET, NO CUTOFF): | 0.2766 |
| REMARK | 3 | R VALUE (WORKING SET, NO CUTOFF): | 0.2772 |
| REMARK | 3 | FREE R VALUE (NO CUTOFF): | 0.3203 |
| REMARK | 3 | FREE R VALUE TEST SET SIZE (%, NO CUTOFF): | 5.3 |
| REMARK | 3 | FREE R VALUE TEST SET COUNT (NO CUTOFF): | 7735 |
| REMARK | 3 | TOTAL NUMBER OF REFLECTIONS (NO CUTOFF): | 146970 |
| REMARK | 3 | | |
| REMARK | 3 | FIT/AGREEMENT OF MODEL FOR DATA WITH F>4SIG(F). | |
| REMARK | 3 | R VALUE (WORKING + TEST SET, F>4SIG(F)): | 0.2566 |
| REMARK | 3 | R VALUE (WORKING SET, F>4SIG(F)): | 0.2573 |
| REMARK | 3 | FREE R VALUE (F>4SIG(F)): | 0.3003 |
| REMARK | 3 | FREE R VALUE TEST SET SIZE (%, F>4SIG(F)): | 5.3 |
| REMARK | 3 | FREE R VALUE TEST SET COUNT (F>4SIG(F)): | 6402 |
| REMARK | 3 | TOTAL NUMBER OF REFLECTIONS (F>4SIG(F)): | 121240 |
| REMARK | 3 | | |
| REMARK | 3 | NUMBER OF NON-HYDROGEN ATOMS USED IN REFINEMENT. | |
| REMARK | 3 | PROTEIN ATOMS: | 10194 |
| REMARK | 3 | NUCLEIC ACID ATOMS: | 0 |
| REMARK | 3 | HETEROGEN ATOMS: | 0 |
| REMARK | 3 | SOLVENT ATOMS: | 132 |
| REMARK | 3 | | |
| REMARK | 3 | MODEL REFINEMENT. | |
| REMARK | 3 | OCCUPANCY SUM OF NON-HYDROGEN ATOMS: | 10326.00 |
| REMARK | 3 | OCCUPANCY SUM OF HYDROGEN ATOMS: | 0.00 |
| REMARK | 3 | NUMBER OF DISCRETELY DISORDERED RESIDUES: | 0 |
| REMARK | 3 | NUMBER OF LEAST-SQUARES PARAMETERS: | 41308 |
| REMARK | 3 | NUMBER OF RESTRAINTS: | 42586 |
| REMARK | 3 | | |
| REMARK | 3 | RMS DEVIATIONS FROM RESTRAINT TARGET VALUES. | |
| REMARK | 3 | BOND LENGTHS (A): | 0.008 |
| REMARK | 3 | ANGLE DISTANCES (A): | 0.020 |
| REMARK | 3 | SIMILAR DISTANCES (NO TARGET VALUES) (A): | 0.000 |
| REMARK | 3 | DISTANCES FROM RESTRAINT PLANES (A): | 0.0247 |
| REMARK | 3 | ZERO CHIRAL VOLUMES (A**3): | 0.027 |
| REMARK | 3 | NON-ZERO CHIRAL VOLUMES (A**3): | 0.032 |
| REMARK | 3 | ANTI-BUMPING DISTANCE RESTRAINTS (A): | 0.025 |
| REMARK | 3 | RIGID-BOND ADP COMPONENTS (A**2): | 0.000 |
| REMARK | 3 | SIMILAR ADP COMPONENTS (A**2): | 0.098 |
| REMARK | 3 | APPROXIMATELY ISOTROPIC ADPS (A**2): | 0.000 |
| REMARK | 3 | | |
| REMARK | 3 | BULK SOLVENT MODELING. | |
| REMARK | 3 | METHOD USED: | MOEWS & KRETSINGER, J.MOL.BIOL.91(1973)201-228 |
| REMARK | 3 | | |
| REMARK | 3 | STEREOCHEMISTRY TARGET VALUES: | ENGH AND HUBER |

TABLE 8-continued

Results from the X-ray model refinement to the observed data of
the NKG2D/MS-Fab complex by the software program SHELXL(14).

| REMARK | 3 | SPECIAL CASE: | |
|---|---|---|---|
| REMARK | 3 | | |
| REMARK | 200 | SOFTWARE USED: | SHELX |
| REMARK | 200 | STARTING MODEL: | NONE |
| REMARK | 200 | | |
| REMARK | 200 | REMARK: | |
| REMARK | 280 | | |
| REMARK | 280 | CRYSTAL | |
| REMARK | 280 | SOLVENT CONTENT, VS (%) 42.2 | |
| REMARK | 280 | MATTHEWS COEFFICIENT, VM (ANGSTROMS**3/DA): | 2.13 |

TABLE 9 hNKG2D monomer "N" (SEQ ID NO: 2) interactions with
the "H", MS-Fab heavy chain (SEQ ID NO: 40) and "L", MS-
Fab light chain (SEQ ID NO: 41). This is for the first of the
crystallographically independent hNKG2D/MS-Fab complex molecules
in the crystal. A cut-off of 4.0 Å was used. The contacts were
identified by the CONTACT computer program of the CCP4 suite(7).

| hNKG2D | | | MS | | | | |
|---|---|---|---|---|---|---|---|
| Res. Type | Res. # and Chain | Atom name | Res. Type | Res. # and Chain | Atom name | Distance [Å] | Possibly H-bond |
| Lys | 150 N | CG | Ser | 31 H | CB | 3.93 | |
| | | | Ser | 31 H | OG | 2.84 | |
| Lys | 150 N | CD | Ser | 31 H | OG | 3.11 | |
| Lys | 150 N | CE | Ser | 31 H | OG | 3.78 | |
| Ser | 151 N | CA | Ser | 30 H | O | 3.73 | |
| | | | Ser | 31 H | O | 3.84 | |
| | | | Ser | 31 H | CA | 3.79 | |
| Ser | 151 N | CB | Ser | 30 H | O | 3.26 | |
| Ser | 151 N | OG | Ser | 30 H | O | 2.30 | *** |
| | | | Ser | 31 H | CA | 3.99 | |
| | | | Ser | 30 H | C | 3.26 | |
| Tyr | 152 N | CG | Tyr | 33 H | CE2 | 3.91 | |
| Tyr | 152 N | CD1 | Tyr | 33 H | CE2 | 3.94 | |
| Tyr | 152 N | CE1 | Tyr | 33 H | CE2 | 3.77 | |
| | | | Tyr | 53 H | CE2 | 3.59 | |
| | | | Tyr | 53 H | CD2 | 3.42 | |
| Tyr | 152 N | CZ | Tyr | 33 H | CE2 | 3.58 | |
| | | | Ser | 30 H | O | 3.88 | |
| | | | Tyr | 53 H | CD2 | 3.66 | |
| | | | Tyr | 32 H | C | 3.84 | |
| | | | Tyr | 32 H | O | 3.52 | |
| | | | Tyr | 33 H | CD2 | 3.67 | |
| Tyr | 152 N | OH | Tyr | 53 H | CD2 | 3.28 | |
| | | | Ser | 52 H | CA | 3.78 | |
| | | | Ser | 52 H | C | 3.86 | |
| | | | Tyr | 53 H | N | 3.06 | *** |
| | | | Tyr | 32 H | C | 3.38 | |
| | | | Tyr | 32 H | O | 2.68 | *** |
| | | | Tyr | 33 H | N | 3.99 | * |
| | | | Tyr | 33 H | CD2 | 3.99 | |
| | | | Tyr | 53 H | CB | 3.84 | |
| Tyr | 152 N | CE2 | Tyr | 33 H | CE2 | 3.56 | |
| | | | Ser | 30 H | O | 3.93 | |
| | | | Tyr | 32 H | N | 3.80 | |
| | | | Tyr | 32 H | CA | 3.61 | |
| | | | Tyr | 32 H | C | 3.37 | |
| | | | Tyr | 32 H | O | 3.49 | |
| | | | Tyr | 33 H | N | 3.81 | |
| | | | Tyr | 33 H | CD2 | 3.40 | |
| Tyr | 152 N | CD2 | Tyr | 33 H | CE2 | 3.73 | |
| | | | Tyr | 33 H | CD2 | 3.87 | |
| Thr | 180 N | CG2 | Tyr | 33 L | OH | 3.43 | |
| | | | Tyr | 33 L | CE1 | 3.96 | |
| Thr | 180 N | C | Tyr | 33 L | OH | 3.94 | |
| Ile | 181 N | N | Tyr | 33 L | OH | 3.46 | * |
| Ile | 181 N | C | Tyr | 33 L | OH | 3.53 | |
| Ile | 181 N | O | Tyr | 33 L | OH | 2.65 | *** |
| | | | Tyr | 33 L | CZ | 3.42 | |
| | | | Tyr | 33 L | CE2 | 3.33 | |

TABLE 9-continued hNKG2D monomer "N" (SEQ ID NO: 2) interactions with
the "H", MS-Fab heavy chain (SEQ ID NO: 40) and "L", MS-
Fab light chain (SEQ ID NO: 41). This is for the first of the
crystallographically independent hNKG2D/MS-Fab complex molecules
in the crystal. A cut-off of 4.0 Å was used. The contacts were
identified by the CONTACT computer program of the CCP4 suite(7).

| hNKG2D | | | MS | | | | |
|---|---|---|---|---|---|---|---|
| Res. Type | Res. # and Chain | Atom name | Res. Type | Res. # and Chain | Atom name | Distance [Å] | Possibly H-bond |
| Ile | 182 N | CD1 | Tyr | 33 L | OH | 3.53 | |
| | | | Tyr | 33 L | CZ | 3.51 | |
| | | | Tyr | 33 L | CE2 | 3.65 | |
| Glu | 183 N | O | Trp | 97 L | CH2 | 3.67 | |
| | | | Trp | 97 L | CZ2 | 3.09 | |
| Met | 184 N | CE | Trp | 98 H | CD1 | 3.75 | |
| | | | Tyr | 33 H | CB | 3.85 | |
| | | | Tyr | 33 H | CG | 3.71 | |
| | | | Tyr | 33 H | CD2 | 3.75 | |
| Met | 184 N | C | Asn | 58 H | ND2 | 3.92 | |
| Met | 184 N | O | Asn | 58 H | CB | 3.95 | |
| | | | Asn | 58 H | CG | 3.86 | |
| | | | Asn | 58 H | ND2 | 2.94 | *** |
| | | | Trp | 97 L | CH2 | 3.62 | |
| | | | His | 50 H | CE1 | 3.55 | |
| | | | His | 50 H | NE2 | 3.45 | * |
| Gln | 185 N | CG | Asn | 58 H | ND2 | 4.00 | |
| Gln | 185 N | CD | Ser | 56 H | OG | 3.04 | |
| | | | Ser | 56 H | O | 3.92 | |
| | | | Ala | 57 H | O | 3.52 | |
| Gln | 185 N | OE1 | Ser | 56 H | CB | 3.77 | |
| | | | Ser | 56 H | OG | 2.41 | *** |
| | | | Ala | 57 H | O | 3.95 | * |
| Gln | 185 N | NE2 | Asn | 58 H | CB | 3.55 | |
| | | | Ser | 56 H | OG | 2.99 | *** |
| | | | Ser | 56 H | C | 3.70 | |
| | | | Ser | 56 H | O | 2.97 | *** |
| | | | Ala | 57 H | O | 2.64 | *** |
| | | | Asn | 58 H | CA | 3.96 | |
| | | | Ala | 57 H | C | 3.27 | |
| | | | Asn | 58 H | N | 3.78 | * |
| Leu | 191 N | CD1 | Tyr | 33 H | OH | 3.05 | |
| Lys | 197 N | NZ | Asp | 99 H | O | 3.13 | *** |
| Tyr | 199 N | OH | Trp | 98 H | CD1 | 3.92 | |
| Tyr | 199 N | CD2 | Tyr | 33 H | CE2 | 3.67 | |
| Glu | 201 N | CG | Tyr | 33 H | CZ | 3.92 | |
| | | | Tyr | 33 H | OH | 2.80 | |
| Glu | 201 N | CD | Tyr | 33 H | OH | 3.29 | |
| | | | Ser | 56 H | OG | 3.60 | |
| Glu | 201 N | OE1 | Tyr | 33 H | CZ | 3.58 | |
| | | | Tyr | 33 H | OH | 3.01 | *** |
| | | | Ser | 56 H | CB | 3.59 | |
| | | | Ser | 56 H | OG | 3.14 | *** |
| | | | Ser | 56 H | O | 3.94 | * |
| | | | Tyr | 33 H | CE1 | 3.24 | |
| Glu | 201 N | OE2 | Ser | 56 H | CB | 3.78 | |
| | | | Ser | 56 H | OG | 3.26 | *** |
| Thr | 205 N | OG1 | Ser | 56 H | CB | 3.63 | |
| | | | Ser | 56 H | OG | 3.95 | * |

TABLE 9-continued hNKG2D monomer "N" (SEQ ID NO: 2) interactions with the "H", MS-Fab heavy chain (SEQ ID NO: 40) and "L", MS-Fab light chain (SEQ ID NO: 41). This is for the first of the crystallographically independent hNKG2D/MS-Fab complex molecules in the crystal. A cut-off of 4.0 Å was used. The contacts were identified by the CONTACT computer program of the CCP4 suite(7).

| hNKG2D | | | MS | | | Distance [Å] | Possibly H-bond |
|---|---|---|---|---|---|---|---|
| Res. Type | Res. # and Chain | Atom name | Res. Type | Res. # and Chain | Atom name | | |
| Thr | 205 N | CG2 | Ser | 56 H | CB | 3.99 | |
| | | | Ser | 54 H | OG | 3.18 | |
| Pro | 206 N | O | Ser | 54 H | CB | 3.03 | |
| | | | Ser | 54 H | OG | 2.87 | *** |
| Asn | 207 N | OD1 | Ser | 54 H | OG | 3.67 | * |
| Thr | 208 N | N | Tyr | 53 H | OH | 3.43 | * |
| Thr | 208 N | CB | Tyr | 53 H | OH | 3.96 | |
| Thr | 208 N | OG1 | Tyr | 53 H | OH | 3.57 | * |
| Thr | 208 N | CG2 | Tyr | 53 H | OH | 3.37 | |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond. Hydrogen-bonds are specific between a donor and an acceptor, are typically strong, and are easily identifiable.

TABLE 10 hNKG2D monomer "C" (SEQ ID NO: 2) interactions with the "B", MS-Fab heavy chain (SEQ ID NO: 40) and "A", MS-Fab light chain (SEQ ID NO: 41). This is for the second of the crystallographically independent hNKG2D/MS-Fab complex molecules in the crystal. A cut-off of 4.0 Å was used. The contacts were identified by the CONTACT computer program of the CCP4 suite(7).

| hNKG2D | | | MS | | | Distance [Å] | Possibly H-bond |
|---|---|---|---|---|---|---|---|
| Res. Type | Res. # and Chain | Atom name | Res. Type | Res. # and Chain | Atom name | | |
| Lys | 150 C | CG | Ser | 31 B | OG | 3.54 | |
| Lys | 150 C | CD | Asp | 27 B | OD1 | 3.96 | |
| | | | Ser | 31 B | OG | 3.56 | |
| Lys | 150 C | CE | Asp | 27 B | CG | 3.67 | |
| | | | Asp | 27 B | OD1 | 2.83 | |
| | | | Asp | 27 B | OD2 | 3.81 | |
| | | | Ser | 31 B | OG | 3.30 | |
| Lys | 150 C | NZ | Asp | 27 B | CG | 3.30 | |
| | | | Asp | 27 B | OD1 | 2.76 | *** |
| | | | Asp | 27 B | OD2 | 3.46 | * |
| Ser | 151 C | CA | Ser | 30 B | O | 3.46 | |
| | | | Ser | 31 B | O | 3.80 | |
| Ser | 151 C | CB | Ser | 30 B | C | 3.99 | |
| | | | Ser | 30 B | O | 3.00 | |
| Ser | 151 C | OG | Ser | 30 B | CB | 3.93 | |
| | | | Ser | 30 B | C | 3.58 | |
| | | | Ser | 30 B | O | 2.47 | *** |
| Tyr | 152 C | CD1 | Tyr | 33 B | CE2 | 3.93 | |
| Tyr | 152 C | CE1 | Tyr | 53 B | CE2 | 3.54 | |
| | | | Tyr | 53 B | CD2 | 3.44 | |
| | | | Tyr | 33 B | CE2 | 3.72 | |
| Tyr | 152 C | CZ | Tyr | 32 B | O | 3.62 | |
| | | | Tyr | 53 B | CD2 | 3.59 | |
| | | | Tyr | 33 B | CE2 | 3.61 | |
| | | | Tyr | 33 B | CD2 | 3.68 | |
| Tyr | 152 C | OH | Tyr | 53 B | CB | 3.88 | |
| | | | Ser | 52 B | CA | 3.64 | |
| | | | Ser | 52 B | CB | 3.73 | |
| | | | Ser | 52 B | C | 3.75 | |
| | | | Tyr | 53 B | N | 2.98 | *** |
| | | | Tyr | 32 B | C | 3.65 | |
| | | | Tyr | 32 B | O | 2.92 | *** |
| | | | Tyr | 53 B | CD2 | 3.25 | |
| | | | Tyr | 33 B | CD2 | 3.98 | |
| Tyr | 152 C | CE2 | Tyr | 32 B | N | 3.82 | |
| | | | Tyr | 32 B | CA | 3.74 | |
| | | | Tyr | 32 B | C | 3.42 | |
| | | | Tyr | 32 B | O | 3.43 | |

TABLE 10-continued hNKG2D monomer "C" (SEQ ID NO: 2) interactions with the "B", MS-Fab heavy chain (SEQ ID NO: 40) and "A", MS-Fab light chain (SEQ ID NO: 41). This is for the second of the crystallographically independent hNKG2D/MS-Fab complex molecules in the crystal. A cut-off of 4.0 Å was used. The contacts were identified by the CONTACT computer program of the CCP4 suite(7).

| hNKG2D | | | MS | | | Distance [Å] | Possibly H-bond |
|---|---|---|---|---|---|---|---|
| Res. Type | Res. # and Chain | Atom name | Res. Type | Res. # and Chain | Atom name | | |
| | | | Tyr | 33 B | N | 3.90 | |
| | | | Tyr | 33 B | CE2 | 3.72 | |
| | | | Tyr | 33 B | CD2 | 3.52 | |
| | | | Ser | 30 B | O | 3.76 | |
| Tyr | 152 C | CD2 | Tyr | 33 B | CE2 | 3.93 | |
| | | | Tyr | 33 B | CD2 | 3.99 | |
| Thr | 180 C | CG2 | Tyr | 33 A | OH | 3.46 | |
| Thr | 180 C | C | Tyr | 33 A | OH | 3.86 | |
| Ile | 181 C | N | Tyr | 33 A | OH | 3.37 | * |
| Ile | 181 C | CA | Tyr | 33 A | OH | 3.92 | |
| Ile | 181 C | C | Tyr | 33 A | OH | 3.38 | |
| Ile | 181 C | O | Tyr | 33 A | CE2 | 3.11 | |
| | | | Tyr | 33 A | CZ | 3.20 | |
| | | | Tyr | 33 A | OH | 2.53 | *** |
| Ile | 182 C | CG1 | Trp | 98 B | CZ2 | 3.52 | |
| | | | Trp | 98 B | CH2 | 3.37 | |
| Ile | 182 C | CD1 | Tyr | 33 A | CE2 | 3.55 | |
| | | | Trp | 98 B | CZ2 | 3.93 | |
| | | | Tyr | 33 A | CZ | 3.48 | |
| | | | Tyr | 33 A | OH | 3.59 | |
| Ile | 182 C | CG2 | Trp | 98 B | CZ2 | 3.97 | |
| Glu | 183 C | O | Trp | 97 A | CH2 | 3.27 | |
| | | | Trp | 97 A | CZ2 | 3.49 | |
| Met | 184 C | CA | His | 50 B | NE2 | 3.99 | |
| Met | 184 C | CB | Tyr | 33 B | CE1 | 3.74 | |
| | | | Tyr | 33 B | OH | 3.98 | |
| | | | Tyr | 33 B | CZ | 3.96 | |
| Met | 184 C | CG | Tyr | 33 B | CD1 | 3.90 | |
| | | | Tyr | 33 B | CE1 | 3.52 | |
| | | | Tyr | 33 B | OH | 3.95 | |
| | | | Tyr | 33 B | CE2 | 3.98 | |
| | | | Tyr | 33 B | CZ | 3.57 | |
| Met | 184 C | CE | Tyr | 33 B | CB | 3.60 | |
| | | | Tyr | 33 B | CG | 3.39 | |
| | | | Tyr | 33 B | CD1 | 3.68 | |
| | | | Tyr | 33 B | CD2 | 3.74 | |
| Met | 184 C | C | His | 50 B | NE2 | 3.85 | |
| Met | 184 C | O | Asn | 58 B | ND2 | 3.02 | *** |
| | | | His | 50 B | CE1 | 3.14 | |
| | | | His | 50 B | NE2 | 2.99 | *** |
| Gln | 185 C | CD | Ala | 57 B | O | 3.73 | |
| | | | Asn | 58 B | CB | 3.48 | |
| | | | Asn | 58 B | CG | 3.89 | |
| | | | Asn | 58 B | ND2 | 3.73 | |
| Gln | 185 C | OE1 | Asn | 58 B | CA | 3.96 | |
| | | | Asn | 58 B | CB | 3.03 | |
| | | | Asn | 58 B | CG | 3.53 | |
| | | | Asn | 58 B | ND2 | 3.23 | *** |
| | | | His | 50 B | ND1 | 3.91 | * |
| | | | His | 50 B | CE1 | 2.97 | |
| | | | His | 50 B | NE2 | 3.62 | * |
| Gln | 185 C | NE2 | Ala | 57 B | C | 3.00 | |
| | | | Asn | 58 B | N | 3.41 | * |
| | | | Asn | 58 B | CA | 3.59 | |
| | | | Ser | 56 B | OG | 3.64 | * |
| | | | Ala | 57 B | O | 2.50 | *** |
| | | | Asn | 58 B | CB | 3.55 | |
| Leu | 191 C | CD1 | Tyr | 33 B | OH | 3.20 | |
| Lys | 197 C | CD | Trp | 98 B | CZ3 | 3.77 | |
| | | | Trp | 98 B | CH2 | 3.71 | |
| Lys | 197 C | CE | Trp | 98 B | CZ3 | 3.54 | |
| | | | Asp | 99 B | O | 3.86 | |
| Lys | 197 C | NZ | Trp | 98 B | CZ3 | 3.50 | |
| | | | Asp | 99 B | O | 2.73 | *** |
| | | | Asp | 99 B | OD1 | 3.56 | * |
| | | | Asp | 99 B | C | 3.74 | |

TABLE 10-continued hNKG2D monomer "C" (SEQ ID NO: 2) interactions with the "B", MS-Fab heavy chain (SEQ ID NO: 40) and "A", MS-Fab light chain (SEQ ID NO: 41). This is for the second of the crystallographically independent hNKG2D/MS-Fab complex molecules in the crystal. A cut-off of 4.0 Å was used. The contacts were identified by the CONTACT computer program of the CCP4 suite(7).

| hNKG2D | | | MS | | | Distance [Å] | Possibly H-bond |
|---|---|---|---|---|---|---|---|
| Res. Type | Res. # and Chain | Atom name | Res. Type | Res. # and Chain | Atom name | | |
| Tyr | 199 C | CE1 | Trp | 98 B | CE3 | 3.87 | |
| | | | Trp | 98 B | CZ3 | 3.29 | |
| | | | Trp | 98 B | CH2 | 3.84 | |
| Tyr | 199 C | CZ | Trp | 98 B | CE3 | 3.64 | |
| | | | Trp | 98 B | CZ3 | 3.39 | |
| Tyr | 199 C | OH | Trp | 98 B | CE3 | 3.01 | |
| | | | Trp | 98 B | CZ3 | 2.80 | |
| Tyr | 199 C | CD2 | Tyr | 33 B | CE2 | 3.57 | |
| | | | Tyr | 33 B | CD2 | 3.98 | |
| Glu | 201 C | CG | Tyr | 33 B | OH | 2.80 | |
| Glu | 201 C | CD | Ser | 56 B | CB | 3.72 | |
| | | | Tyr | 33 B | OH | 3.32 | |
| Glu | 201 C | OE1 | Ser | 56 B | CB | 3.29 | |
| | | | Ser | 56 B | OG | 3.04 | *** |
| | | | Tyr | 33 B | CE1 | 3.58 | |
| | | | Tyr | 33 B | OH | 3.08 | *** |
| | | | Tyr | 33 B | CZ | 3.80 | |
| Glu | 201 C | OE2 | Ser | 56 B | CB | 3.49 | |
| | | | Ser | 56 B | OG | 2.87 | *** |
| Thr | 205 C | OG1 | Ser | 56 B | CB | 3.83 | |
| | | | Ser | 56 B | OG | 3.49 | * |
| Thr | 205 C | CG2 | Ser | 56 B | N | 3.85 | |
| | | | Ser | 56 B | CA | 3.99 | |
| | | | Ser | 56 B | CB | 3.30 | |
| | | | Ser | 56 B | OG | 3.84 | |
| | | | Ser | 54 B | OG | 3.93 | |
| Pro | 206 C | CG | Ser | 54 B | O | 3.97 | |
| Pro | 206 C | C | Ser | 54 B | OG | 3.94 | |
| Pro | 206 C | O | Ser | 54 B | CB | 2.96 | |
| | | | Ser | 54 B | OG | 2.71 | *** |
| Asn | 207 C | OD1 | Ser | 54 B | OG | 3.78 | * |
| Thr | 208 C | N | Tyr | 53 B | OH | 3.59 | * |
| Thr | 208 C | OG1 | Tyr | 53 B | OH | 3.92 | * |
| Thr | 208 C | CG2 | Tyr | 53 B | OH | 3.59 | |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

TABLE 11 hNKG2D monomer "M" (SEQ ID NO: 2) interactions with the "H", MS-Fab heavy chain (SEQ ID NO: 40) and "L", MS-Fab light chain (SEQ ID NO: 41). This is for the first of the crystallographically independent hNKG2D/MS-Fab complex molecules in the crystal. A cut-off of 4.0 Å was used. The contacts were identified by the CONTACT computer program of the CCP4 suite(7).

| hNKG2D | | | MS | | | Distance [Å] | Possibly H-bond |
|---|---|---|---|---|---|---|---|
| Res. Type | Res. # and Chain | Atom name | Res. Type | Res. # and Chain | Atom name | | |
| Tyr | 152 M | OH | Asp | 26 H | O | 3.66 | * |
| Met | 184 M | CG | Gln | 1 H | OE1 | 3.58 | |
| Gln | 185 M | NE2 | Gln | 1 H | OE1 | 3.92 | * |
| Tyr | 199 M | OH | Asp | 26 H | OD2 | 3.87 | * |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

TABLE 12 hNKG2D monomer "D" (SEQ ID NO: 2) interactions with the "B", MS-Fab heavy chain (SEQ ID NO: 40) and "A", MS-Fab light chain (SEQ ID NO: 41). This is for the second of the crystallographically independent hNKG2D/MS-Fab complex molecules in the crystal. A cut-off of 4.0 Å was used. The contacts were identified by the CONTACT computer program of the CCP4 suite(7).

| hNKG2D | | | MS | | | Distance [Å] | Possibly H-bond |
|---|---|---|---|---|---|---|---|
| Res. Type | Res. # and Chain | Atom name | Res. Type | Res. # and Chain | Atom name | | |
| Lys | 150 D | CE | Tyr | 32 B | CE1 | 3.99 | |
| | | | Tyr | 32 B | CZ | 3.78 | |
| | | | Tyr | 32 B | OH | 2.80 | |
| Lys | 150 D | NZ | Tyr | 32 B | CE1 | 3.00 | |
| | | | Tyr | 32 B | CZ | 3.05 | |
| | | | Tyr | 32 B | OH | 2.60 | *** |
| Tyr | 152 D | OH | Asp | 26 B | O | 3.99 | * |
| | | | Gln | 1 B | CA | 3.72 | |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

TABLE 13

Results from the X-ray model refinement to the observed data of the hNKG2D/hzON72-Fab complex by the REFMAC5 software program(11).

| | | |
|---|---|---|
| REMARK 3 | REFINEMENT. | |
| REMARK 3 | PROGRAM: REFMAC 5.2.0019 | |
| REMARK 3 | AUTHORS: MURSHUDOV, VAGIN, DODSON | |
| REMARK 3 | | |
| REMARK 3 | REFINEMENT TARGET: | MAXIMUM LIKELIHOOD |
| REMARK 3 | | |
| REMARK 3 | DATA USED IN REFINEMENT. | |
| REMARK 3 | RESOLUTION RANGE HIGH (ANGSTROMS): | 3.15 |
| REMARK 3 | RESOLUTION RANGE LOW (ANGSTROMS): | 29.66 |
| REMARK 3 | DATA CUTOFF (SIGMA(F)): | NONE |
| REMARK 3 | COMPLETENESS FOR RANGE (%): | 100.00 |
| REMARK 3 | NUMBER OF REFLECTIONS: | 25642 |
| REMARK 3 | | |
| REMARK 3 | FIT TO DATA USED IN REFINEMENT. | |
| REMARK 3 | CROSS-VALIDATION METHOD: | THROUGHOUT |
| REMARK 3 | FREE R VALUE TEST SET SELECTION: | RANDOM |
| REMARK 3 | R VALUE (WORKING + TEST SET): | 0.21870 |
| REMARK 3 | R VALUE (WORKING SET): | 0.21608 |
| REMARK 3 | FREE R VALUE: | 0.26854 |
| REMARK 3 | FREE R VALUE TEST SET SIZE (%): | 5.0 |

TABLE 13-continued

Results from the X-ray model refinement to the observed data of the
hNKG2D/hzON72-Fab complex by the REFMAC5 software program(11).

| REMARK | | | | | | | | |
|---|---|---|---|---|---|---|---|---|
| REMARK 3 | FREE R VALUE TEST SET COUNT: | | | | 1350 | | | |
| REMARK 3 | | | | | | | | |
| REMARK 3 | FIT IN THE HIGHEST RESOLUTION BIN. | | | | | | | |
| REMARK 3 | TOTAL NUMBER OF BINS USED: | | | | 20 | | | |
| REMARK 3 | BIN RESOLUTION RANGE HIGH: | | | | 3.150 | | | |
| REMARK 3 | BIN RESOLUTION RANGE LOW: | | | | 3.231 | | | |
| REMARK 3 | REFLECTION IN BIN (WORKING SET): | | | | 1849 | | | |
| REMARK 3 | BIN COMPLETENESS (WORKING + TEST) (%): | | | | 100.00 | | | |
| REMARK 3 | BIN R VALUE (WORKING SET): | | | | 0.331 | | | |
| REMARK 3 | BIN FREE R VALUE SET COUNT: | | | | 97 | | | |
| REMARK 3 | BIN FREE R VALUE: | | | | 0.385 | | | |
| REMARK 3 | | | | | | | | |
| REMARK 3 | NUMBER OF NON-HYDROGEN ATOMS USED IN REFINEMENT. | | | | | | | |
| REMARK 3 | ALL ATOMS: | | | | 8737 | | | |
| REMARK 3 | | | | | | | | |
| REMARK 3 | B VALUES. | | | | | | | |
| REMARK 3 | FROM WILSON PLOT (A**2): | | | | NULL | | | |
| REMARK 3 | MEAN B VALUE (OVERALL, A**2): | | | | 49.049 | | | |
| REMARK 3 | OVERALL ANISOTROPIC B VALUE. | | | | | | | |
| REMARK 3 | B11 (A**2): | | | | −0.66 | | | |
| REMARK 3 | B22 (A**2): | | | | −3.44 | | | |
| REMARK 3 | B33 (A**2): | | | | 3.95 | | | |
| REMARK 3 | B12 (A**2): | | | | 0.00 | | | |
| REMARK 3 | B13 (A**2): | | | | −1.15 | | | |
| REMARK 3 | B23 (A**2): | | | | 0.00 | | | |
| REMARK 3 | | | | | | | | |
| REMARK 3 | ESTIMATED OVERALL COORDINATE ERROR. | | | | | | | |
| REMARK 3 | ESU BASED ON R VALUE (A): | | | | NULL | | | |
| REMARK 3 | ESU BASED ON FREE R VALUE (A): | | | | 0.502 | | | |
| REMARK 3 | ESU BASED ON MAXIMUM LIKELIHOOD (A): | | | | 0.407 | | | |
| REMARK 3 | ESU FOR B VALUES BASED ON MAXIMUM LIKELIHOOD (A**2): | | | | 54.265 | | | |
| REMARK 3 | | | | | | | | |
| REMARK 3 | CORRELATION COEFFICIENTS. | | | | | | | |
| REMARK 3 | CORRELATION COEFFICIENT FO-FC: | | | | 0.896 | | | |
| REMARK 3 | CORRELATION COEFFICIENT FO-FC FREE: | | | | 0.844 | | | |
| REMARK 3 | | | | | | | | |
| REMARK 3 | RMS DEVIATIONS FROM IDEAL VALUES | | | | COUNT | | RMS | WEIGHT |
| REMARK 3 | BOND LENGTHS REFINED ATOMS (A): | | | | 8971; | | 0.012; | 0.022 |
| REMARK 3 | BOND ANGLES REFINED ATOMS (DEGREES): | | | | 12204; | | 1.516; | 1.948 |
| REMARK 3 | TORSION ANGLES, PERIOD 1 (DEGREES): | | | | 1116; | | 7.673; | 5.000 |
| REMARK 3 | TORSION ANGLES, PERIOD 2 (DEGREES): | | | | 368; | | 37.729; | 24.402 |
| REMARK 3 | TORSION ANGLES, PERIOD 3 (DEGREES): | | | | 1464; | | 21.254; | 15.000 |
| REMARK 3 | TORSION ANGLES, PERIOD 4 (DEGREES): | | | | 32; | | 19.705; | 15.000 |
| REMARK 3 | CHIRAL-CENTER RESTRAINTS (A**3): | | | | 1338; | | 0.109; | 0.200 |
| REMARK 3 | GENERAL PLANES REFINED ATOMS (A): | | | | 6759; | | 0.004; | 0.020 |
| REMARK 3 | NON-BONDED CONTACTS REFINED ATOMS (A): | | | | 3866; | | 0.230; | 0.200 |
| REMARK 3 | NON-BONDED TORSION REFINED ATOMS (A): | | | | 5954; | | 0.312; | 0.200 |
| REMARK 3 | H-BOND (X . . . Y) REFINED ATOMS (A): | | | | 311; | | 0.169; | 0.200 |
| REMARK 3 | SYMMETRY VDW REFINED ATOMS (A): | | | | 56; | | 0.279; | 0.200 |
| REMARK 3 | SYMMETRY H-BOND REFINED ATOMS (A): | | | | 6; | | 0.260; | 0.200 |
| REMARK 3 | | | | | | | | |
| REMARK 3 | ISOTROPIC THERMAL FACTOR RESTRAINTS. | | | | COUNT | | RMS | WEIGHT |
| REMARK 3 | MAIN-CHAIN BOND REFINED ATOMS (A**2): | | | | 5674; | | 0.279; | 1.500 |
| REMARK 3 | MAIN-CHAIN ANGLE REFINED ATOMS (A**2): | | | | 9064; | | 0.512; | 2.000 |
| REMARK 3 | SIDE-CHAIN BOND REFINED ATOMS (A**2): | | | | 3824; | | 0.749; | 3.000 |
| REMARK 3 | SIDE-CHAIN ANGLE REFINED ATOMS (A**2): | | | | 3140; | | 1.231; | 4.500 |
| REMARK 3 | | | | | | | | |
| REMARK 3 | NCS RESTRAINTS STATISTICS | | | | | | | |
| REMARK 3 | NUMBER OF DIFFERENT NCS GROUPS: | | | | 3 | | | |
| REMARK 3 | | | | | | | | |
| REMARK 3 | NCS GROUP NUMBER: | | | | 1 | | | |
| REMARK 3 | CHAIN NAMES: | | | | L A | | | |
| REMARK 3 | NUMBER OF COMPONENTS NCS GROUP: | | | | 1 | | | |
| REMARK 3 | COMPONENT | C | SSSEQI | TO | C | SSSEQI | CODE | |
| REMARK 3 | 1 | L | 1 | | L | 214 | 1 | |
| REMARK 3 | 1 | A | 1 | | A | 214 | 1 | |
| REMARK 3 | | | GROUP | CHAIN | | COUNT | RMS | WEIGHT |
| REMARK 3 | TIGHT POSITIONAL | | 1 | L | (A): | 1656; | 0.05; | 0.05 |
| REMARK 3 | TIGHT THERMAL | | 1 | L | (A**2): | 1656; | 0.06; | 0.50 |
| REMARK 3 | | | | | | | | |
| REMARK 3 | NCS GROUP NUMBER: | | | | 2 | | | |
| REMARK 3 | CHAIN NAMES: | | | | H B | | | |
| REMARK 3 | NUMBER OF COMPONENTS NCS GROUP: | | | | 1 | | | |
| REMARK 3 | COMPONENT | C | SSSEQI | TO | C | SSSEQI | CODE | |
| REMARK 3 | 1 | H | 1 | | H | 220 | 1 | |
| REMARK 3 | 1 | B | 1 | | B | 220 | 1 | |
| REMARK 3 | | | GROUP | CHAIN | | COUNT | RMS | WEIGHT |

TABLE 13-continued

Results from the X-ray model refinement to the observed data of the
hNKG2D/hzON72-Fab complex by the REFMAC5 software program(11).

| REMARK 3 | TIGHT POSITIONAL | | 2 | H | (A): | 1668; | 0.06; | 0.05 |
|---|---|---|---|---|---|---|---|---|
| REMARK 3 | TIGHT THERMAL | | 2 | H | (A**2): | 1668; | 0.07; | 0.50 |
| REMARK 3 | | | | | | | | |
| REMARK 3 | NCS GROUP NUMBER: | | | | | 3 | | |
| REMARK 3 | CHAIN NAMES: | | | | | N C | | |
| REMARK 3 | NUMBER OF COMPONENTS NCS GROUP: | | | | | 1 | | |
| REMARK 3 | COMPONENT | C | SSSEQI | TO | C | SSSEQI | CODE | |
| REMARK 3 | 1 | N | 88 | | N | 215 | 1 | |
| REMARK 3 | 1 | C | 88 | | C | 215 | 1 | |
| REMARK 3 | | | GROUP | CHAIN | | COUNT | RMS | WEIGHT |
| REMARK 3 | TIGHT POSITIONAL | | 3 | N | (A): | 1026; | 0.03; | 0.05 |
| REMARK 3 | TIGHT THERMAL | | 3 | N | (A**2): | 1026; | 0.04; | 0.50 |
| REMARK 3 | | | | | | | | |
| REMARK 3 | | | | | | | | |
| REMARK 3 | TLS DETAILS | | | | | | | |
| REMARK 3 | NUMBER OF TLS GROUPS: | | | | | 5 | | |
| REMARK 3 | ATOM RECORD CONTAINS RESIDUAL B FACTORS ONLY | | | | | | | |
| REMARK 3 | | | | | | | | |
| REMARK 3 | TLS GROUP: | | | | | 1 | | |
| REMARK 3 | NUMBER OF COMPONENTS GROUP: | | | | | 2 | | |
| REMARK 3 | COMPONENTS | C | SSSEQI | TO | C | SSSEQI | | |
| REMARK 3 | RESIDUE RANGE: | L | 1 | | L | 107 | | |
| REMARK 3 | RESIDUE RANGE: | H | 1 | | H | 121 | | |
| REMARK 3 | ORIGIN FOR THE GROUP (A): | | | | | 24.2040 | 90.5950 | 36.8960 |
| REMARK 3 | T TENSOR | | | | | | | |
| REMARK 3 | T11: | −0.1079 | T22: | −0.1998 | | | | |
| REMARK 3 | T33: | −0.2449 | T12: | 0.0010 | | | | |
| REMARK 3 | T13: | −0.0388 | T23: | −0.0446 | | | | |
| REMARK 3 | L TENSOR | | | | | | | |
| REMARK 3 | L11: | 1.1625 | L22: | 5.5207 | | | | |
| REMARK 3 | L33: | 1.9806 | L12: | −0.2378 | | | | |
| REMARK 3 | L13: | −0.5312 | L23: | −0.6045 | | | | |
| REMARK 3 | S TENSOR | | | | | | | |
| REMARK 3 | S11: | 0.0803 | S12: | −0.0443 | S13: | 0.1447 | | |
| REMARK 3 | S21: | 0.3782 | S22: | −0.2475 | S23: | 0.0045 | | |
| REMARK 3 | S31: | −0.0073 | S32: | 0.0331 | S33: | 0.1671 | | |
| REMARK 3 | | | | | | | | |
| REMARK 3 | TLS GROUP: | | | | | 2 | | |
| REMARK 3 | NUMBER OF COMPONENTS GROUP: | | | | | 2 | | |
| REMARK 3 | COMPONENTS | C | SSSEQI | TO | C | SSSEQI | | |
| REMARK 3 | RESIDUE RANGE: | L | 108 | | L | 214 | | |
| REMARK 3 | RESIDUE RANGE: | H | 122 | | H | 220 | | |
| REMARK 3 | ORIGIN FOR THE GROUP (A): | | | | | 35.1200 | 96.1120 | 3.4800 |
| REMARK 3 | T TENSOR | | | | | | | |
| REMARK 3 | T11: | −0.2849 | T22: | 0.0610 | | | | |
| REMARK 3 | T33: | −0.1761 | T12: | −0.0495 | | | | |
| REMARK 3 | T13: | −0.0038 | T23: | 0.0239 | | | | |
| REMARK 3 | L TENSOR | | | | | | | |
| REMARK 3 | L11: | 2.5261 | L22: | 3.4556 | | | | |
| REMARK 3 | L33: | 2.6465 | L12: | −0.8617 | | | | |
| REMARK 3 | L13: | −0.0480 | L23: | −0.4377 | | | | |
| REMARK 3 | S TENSOR | | | | | | | |
| REMARK 3 | S11: | −0.1130 | S12: | 0.4186 | S13: | 0.1914 | | |
| REMARK 3 | S21: | −0.1933 | S22: | −0.0187 | S23: | −0.2357 | | |
| REMARK 3 | S31: | −0.0662 | S32: | 0.2231 | S33: | 0.1317 | | |
| REMARK 3 | | | | | | | | |
| REMARK 3 | TLS GROUP: | | | | | 3 | | |
| REMARK 3 | NUMBER OF COMPONENTS GROUP: | | | | | 2 | | |
| REMARK 3 | COMPONENTS | C | SSSEQI | TO | C | SSSEQI | | |
| REMARK 3 | RESIDUE RANGE: | A | 1 | | A | 107 | | |
| REMARK 3 | RESIDUE RANGE: | B | 1 | | B | 121 | | |
| REMARK 3 | ORIGIN FOR THE GROUP (A): | | | | | 9.5860 | 42.5190 | 37.1590 |
| REMARK 3 | T TENSOR | | | | | | | |
| REMARK 3 | T11: | −0.1183 | T22: | −0.2086 | | | | |
| REMARK 3 | T33: | −0.1316 | T12: | −0.0149 | | | | |
| REMARK 3 | T13: | −0.0254 | T23: | 0.0350 | | | | |
| REMARK 3 | L TENSOR | | | | | | | |
| REMARK 3 | L11: | 1.2758 | L22: | 4.8903 | | | | |
| REMARK 3 | L33: | 1.9328 | L12: | −0.4321 | | | | |
| REMARK 3 | L13: | 0.5123 | L23: | 0.2320 | | | | |
| REMARK 3 | S TENSOR | | | | | | | |
| REMARK 3 | S11: | 0.0143 | S12: | −0.0304 | S13: | −0.1607 | | |
| REMARK 3 | S21: | 0.3252 | S22: | −0.0524 | S23: | −0.1532 | | |
| REMARK 3 | S31: | 0.0565 | S32: | 0.0312 | S33: | 0.0380 | | |
| REMARK 3 | | | | | | | | |
| REMARK 3 | TLS GROUP: | | | | | 4 | | |
| REMARK 3 | NUMBER OF COMPONENTS GROUP: | | | | | 2 | | |

TABLE 13-continued

Results from the X-ray model refinement to the observed data of the
hNKG2D/hzON72-Fab complex by the REFMAC5 software program(11).

| | | | | | | | | | |
|---|---|---|---|---|---|---|---|---|---|
| REMARK 3 | COMPONENTS | C | | SSSEQI | TO | C | | SSSEQI | |
| REMARK 3 | RESIDUE RANGE: | A | | 108 | | A | | 214 | |
| REMARK 3 | RESIDUE RANGE: | B | | 122 | | B | | 220 | |
| REMARK 3 | ORIGIN FOR THE GROUP (A): | | | | | | | −2.3250 | 37.1030  4.0740 |
| REMARK 3 | T TENSOR | | | | | | | | |
| REMARK 3 | T11: | | −0.3236 | T22: | | 0.0744 | | | |
| REMARK 3 | T33: | | −0.1171 | T12: | | −0.0180 | | | |
| REMARK 3 | T13: | | 0.0587 | T23: | | −0.0971 | | | |
| REMARK 3 | L TENSOR | | | | | | | | |
| REMARK 3 | L11: | | 2.6929 | L22: | | 3.2562 | | | |
| REMARK 3 | L33: | | 2.1386 | L12: | | −0.1058 | | | |
| REMARK 3 | L13: | | 0.1471 | L23: | | −0.1863 | | | |
| REMARK 3 | S TENSOR | | | | | | | | |
| REMARK 3 | S11: | | −0.1360 | S12: | | 0.4399 | S13: | −0.3031 | |
| REMARK 3 | S21: | | −0.1914 | S22: | | 0.0086 | S23: | 0.1138 | |
| REMARK 3 | S31: | | −0.0130 | S32: | | −0.2162 | S33: | 0.1274 | |
| REMARK 3 | | | | | | | | | |
| REMARK 3 | TLS GROUP: | | | | | | | 5 | |
| REMARK 3 | NUMBER OF COMPONENTS GROUP: | | | | | | | 2 | |
| REMARK 3 | COMPONENTS | C | | SSSEQI | TO | C | | SSSEQI | |
| REMARK 3 | RESIDUE RANGE: | N | | 89 | | N | | 215 | |
| REMARK 3 | RESIDUE RANGE: | C | | 89 | | C | | 215 | |
| REMARK 3 | ORIGIN FOR THE GROUP (A): | | | | | | | 17.8890 | 66.4400  62.9460 |
| REMARK 3 | T TENSOR | | | | | | | | |
| REMARK 3 | T11: | | 0.4354 | T22: | | 0.1526 | | | |
| REMARK 3 | T33: | | −0.1075 | T12: | | −0.2178 | | | |
| REMARK 3 | T13: | | −0.1984 | T23: | | 0.0840 | | | |
| REMARK 3 | L TENSOR | | | | | | | | |
| REMARK 3 | L11: | | 1.4035 | L22: | | 6.3187 | | | |
| REMARK 3 | L33: | | 3.4618 | L12: | | 1.1657 | | | |
| REMARK 3 | L13: | | 0.1963 | L23: | | 1.1874 | | | |
| REMARK 3 | S TENSOR | | | | | | | | |
| REMARK 3 | S11: | | 0.5552 | S12: | | −0.7422 | S13: | −0.2312 | |
| REMARK 3 | S21: | | 1.1999 | S22: | | −0.1494 | S23: | −0.2659 | |
| REMARK 3 | S31: | | 0.2701 | S32: | | 0.0344 | S33: | −0.4059 | |
| REMARK 3 | | | | | | | | | |
| REMARK 3 | | | | | | | | | |
| REMARK 3 | BULK SOLVENT MODELLING. | | | | | | | | |
| REMARK 3 | METHOD USED: MASK | | | | | | | | |
| REMARK 3 | PARAMETERS FOR MASK CALCULATION | | | | | | | | |
| REMARK 3 | VDW PROBE RADIUS: | | | | | | | 1.20 | |
| REMARK 3 | ION PROBE RADIUS: | | | | | | | 0.80 | |
| REMARK 3 | SHRINKAGE RADIUS: | | | | | | | 0.80 | |
| REMARK 3 | | | | | | | | | |
| REMARK 3 | OTHER REFINEMENT REMARKS: | | | | | | | NULL | |

TABLE 14 hNKG2D monomer "N" (SEQ ID NO: 2) interactions with the "H", hzON72-Fab heavy chain (SEQ ID NO: 70) and "L", hzON72-Fab light chain (SEQ ID NO: 71). This is for the first of the crystallographically independent hNKG2D/hzON72-Fab complex molecules in the crystal. A cut-off of 4.0 Å was used. The contacts were identified by the CONTACT computer program of the CCP4 suite(7).

| hNKG2D | | | hzON72 | | | Dis- | | hNKG2D | | | hzON72 | | | Dis- | |
|---|---|---|---|---|---|---|---|---|---|---|---|---|---|---|---|
| Res. Type | Res. # and Chain | Atom name | Res. Type | Res. # and Chain | Atom name | tance [Å] | Possibly H-bond | Res. Type | Res. # and Chain | Atom name | Res. Type | Res. # and Chain | Atom name | tance [Å] | Possibly H-bond |
| Ser | 165 N | CB | Tyr | 104 H | CE2 | 3.66 | | Pro | 176 N | N | Tyr | 104 H | CE1 | 3.84 | |
| Ser | 165 N | OG | Tyr | 104 H | CE2 | 3.53 | | Pro | 176 N | CA | Gly | 103 H | O | 3.99 | |
| | | | Tyr | 104 H | CD2 | 3.95 | | | | | Gly | 103 H | CA | 3.78 | |
| Trp | 166 N | NE1 | Tyr | 105 H | OH | 3.38 | * | Pro | 176 N | CB | Gly | 103 H | CA | 3.81 | |
| Leu | 174 N | CG | Tyr | 104 H | CE1 | 3.94 | | Asn | 177 N | N | Gly | 103 H | O | 3.29 | *** |
| Leu | 174 N | CD2 | Tyr | 104 H | CD1 | 3.78 | | | | | Tyr | 101 H | OH | 3.79 | * |
| | | | Tyr | 104 H | CE1 | 3.91 | | Asn | 177 N | CA | Tyr | 101 H | OH | 3.63 | |
| Leu | 174 N | C | Tyr | 104 H | OH | 3.97 | | Asn | 177 N | OD1 | Tyr | 101 H | CE2 | 3.52 | |
| Leu | 174 N | O | Tyr | 104 H | CE1 | 3.61 | | Leu | 179 N | C | Tyr | 101 H | OH | 3.54 | |
| | | | Tyr | 104 H | CZ | 3.61 | | Leu | 179 N | O | Gly | 103 H | O | 3.77 | * |
| | | | Tyr | 104 H | OH | 2.90 | *** | | | | Tyr | 101 H | CE1 | 3.60 | |
| Ser | 175 N | C | Tyr | 104 H | CE1 | 3.81 | | | | | Tyr | 101 H | CZ | 3.35 | |
| Ser | 175 N | O | Tyr | 104 H | CE1 | 3.79 | | | | | Tyr | 101 H | OH | 2.33 | *** |

TABLE 14-continued hNKG2D monomer "N" (SEQ ID NO: 2) interactions with the "H", hzON72-Fab heavy chain (SEQ ID NO: 70) and "L", hzON72-Fab light chain (SEQ ID NO: 71). This is for the first of the crystallographically independent hNKG2D/hzON72-Fab complex molecules in the crystal. A cut-off of 4.0 Å was used. The contacts were identified by the CONTACT computer program of the CCP4 suite(7).

| hNKG2D | | | hzON72 | | | Distance [Å] | Possibly H-bond |
|---|---|---|---|---|---|---|---|
| Res. Type | Res. # and Chain | Atom name | Res. Type | Res. # and Chain | Atom name | | |
| Thr | 180 N | CA | Tyr | 104 H | O | 3.40 | |
| Thr | 180 N | CG2 | Trp | 33 H | CZ2 | 3.76 | |
| | | | Val | 106 H | CG2 | 3.60 | |
| | | | Trp | 33 H | NE1 | 3.77 | |
| | | | Tyr | 101 H | CE1 | 3.73 | |
| Thr | 180 N | C | Tyr | 104 H | O | 3.55 | |
| Ile | 181 N | N | Tyr | 104 H | O | 2.78 | *** |
| Ile | 181 N | CA | Tyr | 104 H | O | 3.78 | |
| Ile | 181 N | CB | Tyr | 104 H | O | 3.76 | |
| Ile | 181 N | CG2 | Tyr | 105 H | CE1 | 3.90 | |
| | | | Tyr | 105 H | CZ | 3.63 | |
| | | | Tyr | 105 H | OH | 3.76 | |
| Ile | 182 N | CD1 | Asn | 59 H | OD1 | 3.49 | |
| Ile | 182 N | CG2 | Asn | 59 H | CG | 3.80 | |
| | | | Asn | 59 H | OD1 | 3.51 | |
| | | | Asn | 59 H | ND2 | 3.66 | |
| Glu | 183 N | N | Leu | 94 L | CD1 | 3.64 | |
| Glu | 183 N | CB | Lys | 92 L | O | 3.81 | |
| Glu | 183 N | CG | Tyr | 105 H | OH | 3.91 | |
| Glu | 183 N | CD | Tyr | 105 H | CE1 | 3.87 | |
| | | | Tyr | 105 H | CZ | 3.90 | |
| | | | Tyr | 105 H | OH | 3.06 | |
| Glu | 183 N | OE1 | Lys | 92 L | CG | 3.77 | |
| | | | Lys | 92 L | CD | 3.95 | |
| | | | Lys | 92 L | CE | 3.20 | |
| | | | Thr | 93 L | CG2 | 3.94 | |
| | | | Tyr | 105 H | OH | 3.64 | * |
| Glu | 183 N | OE2 | Tyr | 105 H | CE1 | 3.95 | |
| | | | Tyr | 105 H | CZ | 3.54 | |
| | | | Tyr | 105 H | OH | 2.39 | *** |
| Glu | 183 N | C | Leu | 94 L | CD1 | 3.86 | |
| Glu | 183 N | O | Leu | 94 L | N | 3.16 | *** |
| | | | Thr | 93 L | C | 3.86 | |
| | | | Leu | 94 L | CD1 | 3.45 | |
| | | | Thr | 93 L | CA | 3.51 | |
| | | | Thr | 93 L | CB | 3.61 | |
| Met | 184 N | CG | Leu | 94 L | CB | 3.95 | |
| Met | 184 N | CE | Tyr | 60 H | O | 3.39 | |
| | | | Asn | 59 H | CB | 3.92 | |
| Met | 184 N | O | Tyr | 1 L | CD2 | 3.98 | |
| | | | Leu | 94 L | O | 3.84 | * |
| Lys | 186 N | N | Tyr | 1 L | OH | 3.90 | * |
| Lys | 186 N | CB | Tyr | 1 L | OH | 3.78 | |
| Ala | 193 N | CB | Tyr | 57 H | CE1 | 3.84 | |
| Ser | 194 N | O | Asp | 55 H | CG | 3.84 | |
| | | | Asp | 55 H | OD1 | 3.41 | * |
| | | | Asp | 55 H | OD2 | 3.47 | * |
| Ser | 195 N | CA | Asp | 55 H | OD1 | 3.82 | |
| Ser | 195 N | CB | Asp | 55 H | CG | 3.46 | |
| | | | Asp | 55 H | OD1 | 2.61 | |
| | | | Asp | 55 H | OD2 | 3.81 | |
| Ser | 195 N | OG | Asp | 55 H | CG | 3.74 | |
| | | | Asp | 55 H | OD1 | 3.07 | *** |
| Ser | 195 N | O | Asp | 55 H | CG | 3.71 | |
| | | | Asp | 55 H | OD1 | 3.81 | * |
| | | | Asp | 55 H | OD2 | 3.23 | *** |
| Lys | 197 N | CG | Tyr | 57 H | CD1 | 3.79 | |
| | | | Tyr | 57 H | CE1 | 3.95 | |
| | | | Tyr | 57 H | CD2 | 3.99 | |
| | | | Tyr | 57 H | CG | 3.82 | |
| Lys | 197 N | CD | Tyr | 57 H | CD1 | 3.84 | |
| | | | Tyr | 57 H | CG | 3.74 | |
| | | | Asp | 55 H | OD2 | 3.17 | |
| | | | Tyr | 57 H | CB | 3.89 | |
| Lys | 197 N | CE | Trp | 33 H | CH2 | 3.75 | |
| | | | Trp | 33 H | CZ2 | 3.39 | |
| | | | Asp | 52 H | OD2 | 3.64 | |
| | | | Asp | 55 H | OD2 | 3.27 | |
| | | | Tyr | 57 H | CB | 3.98 | |
| Lys | 197 N | NZ | Asp | 55 H | CG | 3.27 | |
| | | | Trp | 33 H | CZ2 | 3.68 | |
| | | | Asp | 52 H | CB | 3.78 | |
| | | | Asp | 52 H | CG | 3.38 | |
| | | | Asp | 52 H | OD2 | 2.53 | *** |
| | | | Asp | 55 H | CB | 3.57 | |
| | | | Asp | 55 H | OD2 | 2.36 | *** |
| | | | Tyr | 57 H | CB | 3.77 | |
| Tyr | 199 N | CD1 | Tyr | 57 H | OH | 3.64 | |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

TABLE 15 hNKG2D monomer "C" (SEQ ID NO: 2) interactions with the "B", hzON72-Fab heavy chain (SEQ ID NO: 70) and "A", hzON72-Fab light chain (SEQ ID NO: 71). This is for the second of the crystallographically independent hNKG2D/hzON72-Fab complex molecules in the crystal. A cut-off of 4.0 Å was used. The contacts were identified by the CONTACT computer program of the CCP4 suite(7).

| hNKG2D | | | hzON72 | | | Distance [Å] | Possibly H-bond |
|---|---|---|---|---|---|---|---|
| Res. Type | Res. # and Chain | Atom name | Res. Type | Res. # and Chain | Atom name | | |
| Trp | 166 C | NE1 | Tyr | 105 B | OH | 3.26 | *** |
| Leu | 174 C | C | Tyr | 104 B | OH | 3.78 | |
| Leu | 174 C | O | Tyr | 104 B | CE1 | 3.62 | |
| | | | Tyr | 104 B | CZ | 3.37 | |
| | | | Tyr | 104 B | OH | 2.66 | *** |
| Ser | 175 C | C | Tyr | 104 B | CE1 | 3.27 | |
| Ser | 175 C | O | Tyr | 104 B | CD1 | 3.74 | |
| | | | Tyr | 104 B | CE1 | 3.37 | |
| Pro | 176 C | N | Tyr | 104 B | CD1 | 3.99 | |
| | | | Tyr | 104 B | CE1 | 3.13 | |
| | | | Tyr | 104 B | CZ | 3.98 | |
| | | | Tyr | 104 B | OH | 3.92 | * |
| Pro | 176 C | CA | Gly | 103 B | CA | 3.84 | |
| | | | Tyr | 104 B | CD1 | 3.70 | |
| | | | Tyr | 104 B | CE1 | 3.24 | |
| Pro | 176 C | CB | Gly | 103 B | CA | 3.76 | |
| | | | Tyr | 104 B | CE1 | 3.94 | |
| Pro | 176 C | CG | Tyr | 104 B | CE1 | 3.75 | |
| | | | Tyr | 104 B | OH | 3.71 | |
| Pro | 176 C | CD | Tyr | 104 B | CE1 | 3.77 | |
| | | | Tyr | 104 B | OH | 3.68 | |
| Asn | 177 C | N | Gly | 103 B | CA | 3.94 | |
| | | | Gly | 103 B | C | 3.79 | |
| | | | Tyr | 101 B | OH | 3.92 | * |
| | | | Gly | 103 B | O | 3.02 | *** |
| Asn | 177 C | CA | Tyr | 101 B | OH | 3.49 | |
| | | | Gly | 103 B | O | 3.66 | |
| Asn | 177 C | OD1 | Asp | 102 B | O | 3.70 | * |
| | | | Tyr | 101 B | CE2 | 3.41 | |

TABLE 15-continued hNKG2D monomer "C" (SEQ ID NO: 2) interactions with the "B", hzON72-Fab heavy chain (SEQ ID NO: 70) and "A", hzON72-Fab light chain (SEQ ID NO: 71). This is for the second of the crystallographically independent hNKG2D/hzON72-Fab complex molecules in the crystal. A cut-off of 4.0 Å was used. The contacts were identified by the CONTACT computer program of the CCP4 suite(7).

| hNKG2D | | | hzON72 | | | Dis- | |
|---|---|---|---|---|---|---|---|
| Res. Type | Res. # and Chain | Atom name | Res. Type | Res. # and Chain | Atom name | tance [Å] | Possibly H-bond |
| Leu | 179 C | C | Tyr | 101 B | OH | 3.99 | |
| Leu | 179 C | O | Tyr | 101 B | CZ | 3.78 | |
|  |  |  | Tyr | 101 B | CE1 | 3.82 | |
|  |  |  | Tyr | 104 B | O | 3.71 | * |
|  |  |  | Tyr | 101 B | OH | 2.82 | *** |
|  |  |  | Gly | 103 B | O | 3.90 | * |
| Thr | 180 C | CA | Tyr | 104 B | O | 3.36 | |
| Thr | 180 C | CG2 | Trp | 33 B | CZ2 | 3.99 | |
|  |  |  | Val | 106 B | CG2 | 3.72 | |
|  |  |  | Tyr | 101 B | CE1 | 3.84 | |
| Thr | 180 C | C | Tyr | 104 B | O | 3.76 | |
| Ile | 181 C | N | Tyr | 104 B | O | 3.15 | *** |
| Ile | 181 C | CB | Tyr | 105 B | CE2 | 3.99 | |
|  |  |  | Tyr | 105 B | CZ | 3.91 | |
| Ile | 181 C | CG2 | Tyr | 105 B | CE1 | 3.72 | |
|  |  |  | Tyr | 105 B | CZ | 3.49 | |
|  |  |  | Tyr | 105 B | OH | 3.43 | |
| Ile | 182 C | CD1 | Asn | 59 B | OD1 | 3.39 | |
| Ile | 182 C | CG2 | Leu | 94 A | CD2 | 3.97 | |
|  |  |  | Asn | 59 B | CG | 3.80 | |
|  |  |  | Asn | 59 B | OD1 | 3.57 | |
|  |  |  | Asn | 59 B | ND2 | 3.62 | |
|  |  |  | Leu | 94 A | CD1 | 3.96 | |
| Glu | 183 C | N | Leu | 94 A | CD1 | 3.44 | |
| Glu | 183 C | CD | Tyr | 105 B | OH | 3.53 | |
| Glu | 183 C | OE1 | Lys | 92 A | CE | 3.17 | |
|  |  |  | Thr | 93 A | CG2 | 3.35 | |
| Glu | 183 C | OE2 | Tyr | 105 B | CZ | 3.86 | |
|  |  |  | Tyr | 105 B | OH | 2.71 | *** |
| Glu | 183 C | O | Thr | 93 A | C | 3.88 | |
|  |  |  | Leu | 94 A | N | 3.06 | *** |
|  |  |  | Leu | 94 A | CA | 3.93 | |
|  |  |  | Leu | 94 A | O | 3.37 | * |
|  |  |  | Thr | 93 A | CA | 3.68 | |
|  |  |  | Thr | 93 A | CB | 3.54 | |
|  |  |  | Leu | 94 A | CD1 | 3.94 | |
| Met | 184 C | CA | Leu | 94 A | O | 3.78 | |
| Met | 184 C | CE | Tyr | 60 B | O | 3.16 | |
| Met | 184 C | O | Leu | 94 A | O | 3.72 | * |
|  |  |  | Tyr | 1 A | CG | 3.98 | |
|  |  |  | Tyr | 1 A | CD2 | 3.93 | |
| Lys | 186 C | N | Tyr | 1 A | OH | 3.81 | * |
| Lys | 186 C | CA | Tyr | 1 A | OH | 3.65 | |
| Lys | 186 C | CB | Tyr | 1 A | OH | 3.51 | |
| Ala | 193 C | CB | Tyr | 57 B | CE1 | 3.90 | |
| Ser | 194 C | O | Asp | 55 B | OD1 | 3.94 | * |
|  |  |  | Asp | 55 B | OD2 | 3.84 | * |
| Ser | 195 C | CB | Asp | 55 B | CG | 3.63 | |
|  |  |  | Asp | 55 B | OD1 | 2.94 | |
|  |  |  | Asp | 55 B | OD2 | 3.78 | |
| Ser | 195 C | OG | Asp | 55 B | CG | 3.81 | |
|  |  |  | Asp | 55 B | OD1 | 3.25 | *** |
| Ser | 195 C | O | Asp | 55 B | OD2 | 3.52 | * |
| Lys | 197 C | CG | Tyr | 57 B | CZ | 3.90 | |
|  |  |  | Tyr | 57 B | CG | 3.96 | |
|  |  |  | Tyr | 57 B | CD1 | 3.80 | |
|  |  |  | Tyr | 57 B | CE1 | 3.77 | |
| Lys | 197 C | CD | Asp | 55 B | OD2 | 3.58 | |
|  |  |  | Tyr | 57 B | CG | 3.73 | |
|  |  |  | Tyr | 57 B | CD1 | 3.67 | |
| Lys | 197 C | CE | Trp | 33 B | CZ2 | 3.56 | |
|  |  |  | Asp | 52 B | OD2 | 3.96 | |
|  |  |  | Asp | 55 B | OD2 | 3.49 | |
|  |  |  | Trp | 33 B | CH2 | 3.83 | |
| Lys | 197 C | NZ | Trp | 33 B | CZ2 | 3.77 | |
|  |  |  | Asp | 52 B | CG | 3.77 | |
|  |  |  | Asp | 52 B | OD2 | 2.83 | *** |
|  |  |  | Asp | 55 B | CB | 3.88 | |
|  |  |  | Asp | 55 B | CG | 3.44 | |
|  |  |  | Asp | 55 B | OD2 | 2.41 | *** |
|  |  |  | Tyr | 57 B | CB | 3.78 | |

In the last column "***" indicates a strong possibility for a hydrogen bond at this contact (distance < 3.3 Å) as calculated by CONTACT, "*" indicates a weak possibility (distance > 3.3 Å). Blank indicates that the program considered there to be no possibility of a hydrogen bond.

REFERENCE LIST

1. Li, P., Morris, D. L., Willcox, B. E., Steinle, A., Spies, T., and Strong, R. K. (2001) *Nature Immunology* 2, 443-451
2. Ursby, T., Mammen, C. B., Cerenius, Y., Svensson, C., Sommarin, B., Fodje, M. N., Kvick, Å., Logan, D. T., Als-Nielsen, J., Thunnissen, M. M. G. M., Larsen, S., and Liljas, A. (2004) The New Macromolecular Crystallography Stations At MAX-lab: The MAD Station.
3. Kabsch, W. (1993) *J. Appl. Crystallogr.* 26, 795-800
4. Vagin, A. and Teplyakov, A. (1997) *J. Appl. Crystallogr.* 30, 1022-1025
5. Mccoy, A. J., Grosse-Kunstleve, R. W., Storoni, L. C., and Read, R. J. (2005) *Acta Crystallographica Section D Biological Crystallography* 61, 458-464
6. Mccoy, A. J., Grosse-Kunstleve, R. W., Adams, P. D., Winn, M. D., Storoni, L. C., and Read, R. J. (2007) *J. Appl. Crystallogr.* 40, 658-674
7. Bailey, S. (1994) *Acta Crystallogr. Sect. D-Biol. Crystallogr.* 50, 760-763
8. Berman, H. M., Westbrook, J., Feng, Z., Gilliland, G., Bhat, T. N., Weissig, H., Shindyalov, I. N., and Bourne, P. E. (2000) *Nucleic Acids Res.* 28, 235-242
9. Vajdos, F. F., Adams, C. W., Breece, T. N., Presta, L. G., de Vos, A. M., and Sidhu, S. S. (2002) *Journal of Molecular Biology* 320, 415-428
10. McFarland, B. J., Kortemme, T., Yu, S. F., Baker, D., and Strong, R. K. (2003) *Structure (Cambridge)* 11, 411-422
11. Murshudov, G. N., Vagin, A. A., and Dodson, E. J. (1997) *Acta Crystallogr. Sect. D-Biol. Crystallogr.* 53, 240-255
12. Emsley, P. and Cowtan, K. (2004) *Acta Crystallogr. Sect. D-Biol. Crystallogr.* 60, 2126-2132
13. Evans, P. (1962) *Acta Crystallogr D Biol Crystallogr.* 2006. January 72-82
14. Sheldrick, G. (2008) *Act Cryst a* 64, 112-122
15. Ohto, U., Mizutani, R., Nakamura, M., Adachi, H., and Satow, Y. (2004) *J Synchrotron Radiat* 11, 105-108

Exemplary Embodiments

The following are exemplary embodiments of the invention.

1. An isolated human or humanized monoclonal antibody, or antigen-binding fragment thereof, which binds human NKG2D (hNKG2D).

2. The antibody or antigen-binding fragment of the preceding embodiment, which reduces hNKG2D-mediated activation of an hNKG2D-expressing NK or T cell.
3. The antibody or antigen-binding fragment of any preceding embodiment, which competes with at least one hNKG2D ligand in binding to hNKG2D.
4. The antibody or antigen-binding fragment of the preceding embodiment, wherein the ligand is MICA.
5. The antibody or antigen-binding fragment of any preceding embodiment, which reduces the amount of NKG2D on the surface of an NKG2D-expressing NK or T cell.
6. The antibody or antigen-binding fragment of any preceding embodiment, which, when immobilized, does not significantly co-stimulate CD3-triggered proliferation of peripheral blood mononuclear cells (PBMCs).
7. The antibody or antigen-binding fragment of any preceding embodiment, which, when immobilized, has no significant agonistic effect on hNKG2D-mediated activation of an hNKG2D-expressing NK or T cell.
8. The antibody or antigen-binding fragment of any preceding embodiment, which binds to cynomolgous and rhesus NKG2D.
9. The antibody of any preceding embodiment, which binds to hNKG2D with a KD of 1 nM or less.
10. The antibody of any preceding embodiment, which binds to hNKG2D with a KD of 0.1 nM or less.
11. The antibody or antigen-binding fragment of any preceding embodiment, which, when added to NKG2D-expressing NK or T cells, cross-links no more than two hNKG2D dimers.
12. The antibody or antigen-binding fragment of any preceding embodiment, which binds strongly to only a first hNKG2D monomer in an hNKG2D dimer.
13. The antibody or antigen-binding fragment of the preceding embodiment, which, when bound to the first hNKG2D monomer, blocks binding of the antibody or antigen-binding fragment to the second hNKG2D monomer.
14. The antibody or antigen-binding fragment of any preceding embodiment, for which the ratio of the solvent-exclusion areas on the first and second hNKG2D monomers in an hNKG2D dimer is about 2:1 or more.
15. The antibody or antigen-binding fragment of the preceding embodiment, for which the ratio is about 3:1 or more.
16. The antibody or antigen-binding fragment of any preceding embodiment, which competes with a reference antibody in binding to NKG2D, wherein the reference antibody is selected from the group consisting of:
   (a) an antibody comprising a heavy-chain variable region comprising the sequence of SEQ ID NO:11 and a light-chain variable region comprising the sequence of SEQ ID NO:12;
   (b) an antibody comprising a heavy-chain variable region comprising the sequence of SEQ ID NO:13 and a light-chain variable region comprising the sequence of SEQ ID NO:14;
   (c) an antibody comprising a heavy-chain variable region comprising the sequence of SEQ ID NO:44 and a light-chain variable region comprising the sequence of SEQ ID NO:45; and
   (d) an antibody comprising a heavy-chain variable region comprising the sequence of SEQ ID NO:46 and a light-chain variable region comprising the sequence of SEQ ID NO:47.
17. The antibody or antigen-binding fragment of any of the preceding embodiments, which binds to the same epitope of NKG2D as a reference antibody, wherein the reference antibody is selected from the group consisting of:
   (a) an antibody comprising a heavy-chain variable region comprising the sequence of SEQ ID NO:11 and a light-chain variable region comprising the sequence of SEQ ID NO:12;
   (b) an antibody comprising a heavy-chain variable region comprising the sequence of SEQ ID NO:13 and a light-chain variable region comprising the sequence of SEQ ID NO:14;
   (c) an antibody comprising a heavy-chain variable region comprising the sequence of SEQ ID NO:44 and a light-chain variable region comprising the sequence of SEQ ID NO:45; and
   (d) an antibody comprising a heavy-chain variable region comprising the sequence of SEQ ID NO:46 and a light-chain variable region comprising the sequence of SEQ ID NO:47.
18. The antibody or antigen-binding fragment of any of the preceding embodiments, which binds to NKG2D with substantially the same KD as a reference antibody, wherein the reference antibody is selected from the group consisting of:
   (a) an antibody comprising a heavy-chain variable region comprising the sequence of SEQ ID NO:11 and a light-chain variable region comprising the sequence of SEQ ID NO:12;
   (b) an antibody comprising a heavy-chain variable region comprising the sequence of SEQ ID NO:13 and a light-chain variable region comprising the sequence of SEQ ID NO:14;
   (c) an antibody comprising a heavy-chain variable region comprising the sequence of SEQ ID NO:44 and a light-chain variable region comprising the sequence of SEQ ID NO:45; and
   (d) an antibody comprising a heavy-chain variable region comprising the sequence of SEQ ID NO:46 and a light-chain variable region comprising the sequence of SEQ ID NO:47.
19. The antibody or antigen-binding fragment of any of embodiments 16-18, wherein the reference antibody comprises a heavy-chain variable region comprising the sequence of SEQ ID NO:44 and a light-chain variable region comprising the sequence of SEQ ID NO:45.
20. The antibody or antigen-binding fragment of the preceding embodiment, which binds to an epitope comprising Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and/or Thr 208 of SEQ ID NO:2.
21. The antibody or antigen-binding fragment of the preceding embodiment, which binds to an epitope comprising 5 or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of SEQ ID NO:2.
22. The antibody or antigen-binding fragment of the preceding embodiment, which binds to an epitope comprising Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of SEQ ID NO:2.

23. The antibody or antigen-binding fragment of any of embodiments 16-18, wherein the reference antibody comprises a heavy-chain variable region comprising the sequence of SEQ ID NO:46 and a light-chain variable region comprising the sequence of SEQ ID NO:47.

24. The antibody or antigen-binding fragment of any preceding embodiment, comprising a heavy chain variable region that is the product of or derived from a set of human genes comprising:
 (a) VH3_21, D3-9, and JH4 genes;
 (b) VH3_20, D3-10, and JH6 genes;
 (c) VH4_59, D7_27_R3, and JH3 genes; or
 (d) VH5_51, D3_10_R3 and JH4 genes.

25. The antibody or antigen-binding fragment of any preceding embodiment, comprising a light-chain variable region that is the product of or derived from a set of human genes comprising
 (a) VKI_L15 and JK2 genes;
 (b) VKIII_A27 and JK3 genes;
 (c) VKIII_A27 and JK1 genes; or
 (d) VKIII_L6 and JK1 genes.

26. The antibody or antigen-binding fragment of any preceding embodiment, comprising a heavy chain variable region that is the product of or derived from a set of human genes comprising VH4_59, D7_27_R3, and JH3 genes, and a light-chain variable region that is the product of or derived from a set of human genes comprising VKIII_A27 and JK1 genes.

27. The antibody or antigen-binding fragment of any preceding embodiment, comprising a paratope comprising a residue corresponding to Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 or Asp 99 of SEQ ID NO: 44 or Tyr 33 or Trp 97 of SEQ ID NO:45, or any combination thereof.

28. The antibody or antigen-binding fragment of the preceding embodiment, comprising a paratope comprising at least 5 residues selected from the residues corresponding to Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 or Asp 99 of SEQ ID NO: 44 or Tyr 33 or Trp 97 of SEQ ID NO:45, or any combination thereof.

29. The antibody or antigen-binding fragment of the preceding embodiment, comprising a paratope comprising residues corresponding to Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of SEQ ID NO: 44 and Tyr 33 and Trp 97 of SEQ ID NO:45.

30. The antibody or antigen-binding fragment of any preceding embodiment, comprising:
 (a) a heavy-chain variable region CDR1 comprising the sequence of SEQ ID NO:48;
 (b) a heavy-chain variable region CDR2 comprising the sequence of SEQ ID NO:49; and
 (c) a heavy-chain variable region CDR3 comprising the sequence of SEQ ID NO:50.

31. The antibody or antigen-binding fragment of the preceding embodiment, comprising:
 (a) a light-chain variable region CDR1 comprising the sequence of SEQ ID NO:51;
 (b) a light-chain variable region CDR2 comprising the sequence of SEQ ID NO:52; and
 (c) a light-chain variable region CDR3 comprising the sequence of SEQ ID NO:53.

32. The antibody or antigen-binding fragment of any preceding embodiment, comprising a heavy-chain variable region comprising the sequence of SEQ ID NO:44, and a light-chain variable region comprising the sequence of SEQ ID NO:45.

33. The antibody or antigen-binding fragment of any of embodiments 1-25, comprising a heavy chain variable region that is the product of or derived from a set of human genes comprising VH5_51, D3_10_R3 and JH4 genes, and a light-chain variable region that is the product of or derived from a set of human genes comprising VKIII_L6 and JK1 genes.

34. The antibody or antigen-binding fragment of the preceding embodiment, comprising:
 (a) a heavy-chain variable region CDR1 comprising the sequence of SEQ ID NO:54;
 (b) a heavy-chain variable region CDR2 comprising the sequence of SEQ ID NO:55; and
 (c) a heavy-chain variable region CDR3 comprising the sequence of SEQ ID NO:56.

35. The antibody or antigen-binding fragment of the preceding embodiment, comprising:
 (a) a light-chain variable region CDR1 comprising the sequence of SEQ ID NO:57;
 (b) a light-chain variable region CDR2 comprising the sequence of SEQ ID NO:58; and
 (c) a light-chain variable region CDR3 comprising the sequence of SEQ ID NO:59.

36. The antibody or antigen-binding fragment of the preceding embodiment, comprising a heavy-chain variable region comprising the sequence of SEQ ID NO:46, and a light-chain variable region comprising the sequence of SEQ ID NO:47.

37. The antibody or antigen-binding fragment of embodiment 1, comprising:
 (a) a heavy-chain variable region CDR1 comprising the sequence of SEQ ID NO:15;
 (b) a heavy-chain variable region CDR2 comprising the sequence of SEQ ID NO:16; and
 (c) a heavy-chain variable region CDR3 comprising the sequence of SEQ ID NO:17.

38. The antibody or antigen-binding fragment of the preceding embodiment, comprising:
 (a) a light-chain variable region CDR1 comprising the sequence of SEQ ID NO:18;
 (b) a light-chain variable region CDR2 comprising the sequence of SEQ ID NO:19; and
 (c) a light-chain variable region CDR3 comprising the sequence of SEQ ID NO:20.

39. The antibody or antigen-binding fragment of the preceding embodiment, comprising a heavy-chain variable region comprising the sequence of SEQ ID NO:11, and a light-chain variable region comprising the sequence of SEQ ID NO:12.

40. The antibody or antigen-binding fragment of embodiment 1, comprising:
 (a) a heavy-chain variable region CDR1 comprising the sequence of SEQ ID NO:21;
 (b) a heavy-chain variable region CDR2 comprising the sequence of SEQ ID NO:22; and
 (c) a heavy-chain variable region CDR3 comprising the sequence of SEQ ID NO:23.

41. The antibody or antigen-binding fragment of the preceding embodiment, comprising:
    (a) a light-chain variable region CDR1 comprising the sequence of SEQ ID NO:24;
    (b) a light-chain variable region CDR2 comprising the sequence of SEQ ID NO:25; and
    (c) a light-chain variable region CDR3 comprising the sequence of SEQ ID NO:26.
42. The antibody or antigen-binding fragment of the preceding embodiment, comprising a heavy-chain variable region comprising the sequence of SEQ ID NO:13, and a light-chain variable region comprising the sequence of SEQ ID NO:14.
43. The antibody or antigen-binding fragment of embodiment 1, comprising:
    (a) a heavy-chain variable region CDR1 comprising the sequence of SEQ ID NO:48;
    (b) a heavy-chain variable region CDR2 comprising the sequence of SEQ ID NO:49; and
    (c) a heavy-chain variable region CDR3 comprising the sequence of SEQ ID NO:50.
44. The antibody or antigen-binding fragment of the preceding embodiment, comprising:
    (a) a light-chain variable region CDR1 comprising the sequence of SEQ ID NO:51;
    (b) a light-chain variable region CDR2 comprising the sequence of SEQ ID NO:52; and
    (c) a light-chain variable region CDR3 comprising the sequence of SEQ ID NO:53.
45. The antibody or antigen-binding fragment of embodiment 1, comprising a heavy-chain variable region comprising the sequence of SEQ ID NO:44, and a light-chain variable region comprising the sequence of SEQ ID NO:45.
46. The antibody or antigen-binding fragment of embodiment 1, comprising:
    (a) a heavy-chain variable region CDR1 comprising the sequence of SEQ ID NO:54;
    (b) a heavy-chain variable region CDR2 comprising the sequence of SEQ ID NO:55; and
    (c) a heavy-chain variable region CDR3 comprising the sequence of SEQ ID NO:56.
47. The antibody or antigen-binding fragment of the preceding embodiment, comprising:
    (a) a light-chain variable region CDR1 comprising the sequence of SEQ ID NO:57;
    (b) a light-chain variable region CDR2 comprising the sequence of SEQ ID NO:58; and
    (c) a light-chain variable region CDR3 comprising the sequence of SEQ ID NO:59.
48. The antibody or antigen-binding fragment of the preceding embodiment, comprising a heavy-chain variable region comprising the sequence of SEQ ID NO:46, and a light-chain variable region comprising the sequence of SEQ ID NO:47.
49. The antibody or antigen-binding fragment of embodiment 1, comprising
    (a) a heavy-chain variable region CDR1 comprising the sequence of SEQ ID NO:15, 21, 48, or 54;
    (b) a heavy-chain variable region CDR2 comprising the sequence of SEQ ID NO:16, 22, 49, or 55;
    (c) a heavy-chain variable region CDR3 comprising the sequence of SEQ ID NO:17, 23, 50, or 56;
    (d) a light-chain variable region CDR1 comprising the sequence of SEQ ID NO:18, 24, 51, or 57;
    (e) a light-chain variable region CDR2 comprising the sequence of SEQ ID NO:19, 25, 52, or 58; and
    (f) a light-chain variable region CDR3 comprising the sequence of SEQ ID NO:20, 26, 53, or 59;
    with no more than 8 conservative amino acid substitutions.
50. The antibody or antigen-binding fragment of the preceding embodiment, comprising no more than 5 amino acid substitutions.
51. The antibody of any preceding embodiment, which is human.
52. The antibody or antigen-binding fragment of any preceding embodiment, which is bivalent.
53. The antibody of the preceding embodiment, which is an IgG1, IgG2, IgG3, or IgG4 antibody.
54. The antibody of the preceding embodiment, which is an IgG4 antibody.
55. The antibody of any preceding embodiments, which comprises an S241P mutation in a VH chain.
56. An isolated antibody comprising a heavy-chain sequence comprising the sequence of SEQ ID NO:7 and a light-chain sequence comprising the sequence of SEQ ID NO:8.
57. An isolated antibody comprising a heavy-chain sequence comprising the sequence of SEQ ID NO:9 and a light-chain sequence comprising the sequence of SEQ ID NO:10.
58. An isolated antibody comprising a heavy-chain sequence comprising the sequence of SEQ ID NO:40 and a light-chain sequence comprising the sequence of SEQ ID NO:41.
59. An isolated antibody comprising a heavy-chain sequence comprising the sequence of SEQ ID NO:42 and a light-chain sequence comprising the sequence of SEQ ID NO:43.
60. An isolated antibody that competes more with 16F16, 16F31, MS, or 21F2 than with any of ON72, BAT221, 5C6, 1D11, ECM217, or 149810 in binding to hNKG2D, and prevents NKG2D-mediated activation of an NKG2D-expressing NK or T cell.
61. The isolated antibody of the preceding embodiment, which competes more with MS than with ON72, BAT221, 5C6, 1D11, ECM217, or 149810.
62. The isolated antibody of embodiment 60, which competes more with 21F2 than with ON72, BAT221, 5C6, 1D11, ECM217, or 149810.
63. An isolated antibody that binds cell surface-associated hNKG2D on an NK-cell preparation with a first half maximal effective concentration (EC50), and reduces killing of target cells expressing NKG2D-ligand mediated by the NK cell preparation with a second EC50, wherein the second EC50 is substantially lower than the first EC50.
64. The antibody of the preceding embodiment, wherein the NK-cell preparation is NK-92 or NKL cells.
65. The antibody of the preceding embodiment, wherein the ligand is ULBP-3 or MICA.
66. The antibody of the preceding embodiment, wherein the second EC50 is no more than 80% of the first EC50.
67. The antibody of the preceding embodiment, wherein the second EC50 is no more than 50% of the first EC50.
68. An isolated antibody that binds hNKG2D, which antibody achieves its maximum reduction of NK-cell mediated killing of target cells expressing a ligand at a concentration lower than a concentration substantially saturating cell-surface associated NKG2D.
69. An isolated antibody that binds hNKG2D, prevents NKG2D-mediated activation of an NKG2D-expressing NK or T cell, and is capable of downmodulating more than 70% of cell-surface-associated NKG2D.

70. The antibody of the preceding embodiment, which is capable of downmodulating less than 90% of cell-surface-associated NKG2D of an NK cell.

71. An isolated antibody that binds hNKG2D, and which binds to human and cynomolgous NKG2D-expressing cells with similar affinity.

72. The antibody of the preceding embodiment, which has an EC50 for binding to cynomolgous CD8+ T cells in a PBMC preparation that is at least 50% of its EC50 for binding to human CD8+ T cells in a PBMC preparation.

73. The antibody of the preceding embodiment, which has an EC50 for binding to cynomolgous CD8+ T cells in a PBMC preparation that is at least 65% of its EC50 for binding to human CD8+ T cells in a PBMC preparation.

74. The isolated antibody of any preceding embodiments, which has an affinity for human NKG2D of no more than 0.1 nM.

75. The antibody of any preceding embodiment, which has an affinity for human NKG2D of no more than 10 pM.

76. The antibody of any of embodiments 60-75, comprising:
    (a) a heavy-chain variable region CDR1 comprising the sequence of SEQ ID NO:48 or 54;
    (b) a heavy-chain variable region CDR2 comprising the sequence of SEQ ID NO:49 or 55; and
    (c) a heavy-chain variable region CDR3 comprising the sequence of SEQ ID NO:50 or 56.

77. The antibody of the preceding embodiment, comprising:
    (a) a light-chain variable region CDR1 comprising the sequence of SEQ ID NO:51 or 57;
    (b) a light-chain variable region CDR2 comprising the sequence of SEQ ID NO:52 or 58; and
    (c) a light-chain variable region CDR3 comprising the sequence of SEQ ID NO:53 or 59.

78. The antibody of any of embodiments 60-77, which is human.

79. An antigen-binding fragment of the antibody of any of embodiments 60-78.

80. A nucleic acid encoding a variable-heavy or variable-light chain of the antibody or antigen-binding fragment of any preceding embodiment.

81. An expression vector comprising the nucleic acid of the preceding embodiment.

82. A host cell comprising the expression vector of the preceding embodiment.

83. A host cell producing the antibody or antigen-binding fragment of any of embodiments 1-79.

84. The host cell of any of embodiments 82 and 83, which is a CHO cell.

85. A method of producing an anti-NKG2D antibody or antigen-binding fragment comprising culturing the host cell of any of embodiments 82 to 84 under suitable conditions and recovering said antibody or antigen-binding fragment thereof.

86. A method of producing a variant anti-NKG2D antibody, or an antigen-binding fragment thereof, comprising
    (a) providing a heavy-chain variable region comprising a CDR1 sequence selected from SEQ ID NOS:15, 21, 48, and 54, a CDR2 sequence selected from SEQ ID NOS:16, 22, 49 and 55, and a CDR3 sequence selected from SEQ ID NOS:17, 23, 50 and 56;
    (b) providing a light-chain variable region comprising a CDR1 sequence selected from SEQ ID NOS:18, 24, 51 and 57, a CDR2 sequence selected from SEQ ID NOS:19, 25, 52 and 58, and a CDR3 sequence selected from SEQ ID NOS:20, 26, 53, and 59;
    (c) altering up to 8 amino acid residues in each of the heavy- and light chain variable regions to produce altered heavy- and light-chain variable regions; and
    (d) expressing a variant anti-NKG2D antibody comprising the altered heavy- and light-chain variable regions in a host cell.

87. An immunoconjugate comprising the antibody or antigen-binding fragment of any of embodiments 1-79, linked to a therapeutic agent.

88. A multispecific molecule comprising the antibody or antigen-binding fragment of any of embodiments 1-79, linked to a second moiety having a different binding specificity than the antibody.

89. The multispecific molecule of the preceding embodiment, wherein the second moiety is a second antibody, or antigen-binding fragment thereof.

90. A composition comprising the antibody or antigen-binding fragment of any of embodiments 1-79, and a pharmaceutically acceptable carrier.

91. A method for preventing NKG2D-mediated activation of an NKG2D-expressing NK or T cell, comprising contacting the NK or T cell with the antibody or antigen-binding fragment of any of embodiments 1-79, wherein the antibody or antigen-binding fragment competes with at least one NKG2D ligand in binding to NKG2D.

92. The method of the preceding embodiment, wherein the NKG2D ligand is MICA.

93. A method for reducing the amount of NKG2D on the surface of an NKG2D-expressing NK or T cell, comprising contacting the NK or T cell with the antibody or antigen-binding fragment of any of embodiments 1-79, wherein the antibody or antigen-binding fragment competes with at least one NKG2D ligand in binding to human NKG2D.

94. A method for treating an inflammatory or autoimmune disorder, comprising administering the composition of embodiment 90 to a human subject suffering from or at risk for an inflammatory or autoimmune disorder.

95. The method of the preceding embodiment, wherein the patient is suffering from or at risk for an autoimmune disorder.

96. The method of the preceding embodiment, wherein the autoimmune disorder is rheumatoid arthritis.

97. The method of embodiment 95, wherein the disorder is multiple sclerosis.

98. The method of embodiment 95, wherein the disorder is systemic lupus erythomatosus (SLE).

99. The method of embodiment 95, wherein the disorder is psoriasis.

100. The method of embodiment 95, wherein the disorder is celiac disease.

101. The method of embodiment 95, wherein the disorder is an inflammatory bowel disease.

102. The method of the preceding embodiment, wherein the inflammatory bowel disease is ulcerative colitis.

103. The method of embodiment 101, wherein the inflammatory bowel disease is Crohn's disease.

104. The method of embodiment 94, wherein the human subject is suffering from or at risk for transplant rejection or graft-versus-host disease.

105. The method of the preceding embodiment, wherein the transplant is a heart transplant or a bone marrow transplant.
106. The method of any of embodiments 94 to 105, further comprising administering a second anti-inflammatory agent.
107. The method of the preceding embodiment, wherein the second anti-inflammatory agent is selected from an immunosuppressant, an analgesic, an anti-angiogenic agent, a corticosteroid, a B-cell depletion agent, a B-cell antagonist, a T-cell antagonist, a complement-inhibiting agent, an anti-cytokine agent, and an anti-cytokine receptor agent, and combinations thereof.
108. The method of any of embodiments 106 and 107, wherein the second anti-inflammatory agent is an antagonist of TNFalpha activity.
109. A method for treating an inflammatory or autoimmune disorder, comprising administering the composition of embodiment 90 to a human subject at risk for an inflammatory or autoimmune disorder.
110. The method of the preceding embodiment, wherein the human subject is at risk for transplant rejection or graft-versus-host disease.
111. The use of the antibody or antigen-binding fragment of any of embodiments 1-79, in the preparation of a medicament to treat an inflammatory or autoimmune disorder in a human subject.
112. The antibody or antigen-binding fragment of any of embodiments 1-79, for use in treating an inflammatory or autoimmune disorder in a human subject.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. An isolated antibody or an antigen-binding fragment thereof which binds human NKG2D (hNKG2D) and comprises
   (a) a heavy-chain variable region CDR1 comprising the sequence of SEQ ID NO:48;
   (b) a heavy-chain variable region CDR2 comprising the sequence of SEQ ID NO:49;
   (c) a heavy-chain variable region CDR3 comprising the sequence of SEQ ID NO:50;
   (d) a light-chain variable region CDR1 comprising the sequence of SEQ ID NO:51;
   (e) a light-chain variable region CDR2 comprising the sequence of SEQ ID NO:52; and
   (f) a light-chain variable region CDR3 comprising the sequence of SEQ ID NO:53.

2. The isolated antibody or antigen-binding fragment thereof of claim 1, which comprises a heavy-chain variable region comprising the sequence of SEQ ID NO:44 and a light-chain variable region comprising the sequence of SEQ ID NO:45.

3. The isolated antibody or antigen-binding portion thereof of claim 1, wherein the antibody or antigen-binding portion thereof is a monoclonal antibody.

4. The isolated antibody or antigen-binding portion thereof of claim 3, wherein the antibody or antigen-binding portion thereof is an IgG4 isotype.

5. The isolated antibody or antigen-binding portion thereof of claim 3, wherein the antibody or antigen-binding portion thereof is a human antibody.

6. The isolated antibody or antigen-binding portion thereof of claim 3, wherein the antibody or antigen-binding portion thereof is a chimeric antibody.

7. The isolated antibody or antigen-binding portion thereof of claim 1, wherein the antibody or antigen-binding portion thereof competes with MICA binding to human NKG2D.

8. The isolated antibody or antigen-binding portion thereof of claim 1, wherein the antibody or antigen-binding portion thereof reduces human NKG2D-mediated activation of a human NKG2D-expressing Natural Killer (NK) cell or T cell.

9. The isolated antibody or antigen-binding portion thereof of claim 1, wherein the antibody or antigen-binding portion thereof reduces the amount of NKG2D on the surface of an NKG2D expressing NK cell or T cell.

10. A composition comprising the antibody or antigen-binding portion thereof of claim 1 and a pharmaceutically acceptable carrier.

11. A composition comprising the antibody or antigen-binding portion thereof of claim 1 linked to a therapeutic agent.

12. The composition of claim 11, wherein the therapeutic agent is a cytotoxin or a radioactive agent.

13. A bispecific molecule comprising the antibody or antigen-binding portion thereof of claim 1 linked to a second functional moiety having a different binding specificity than said antibody or antigen-binding portion thereof.

* * * * *

SEQUENCE LISTING

<160> NUMBER OF SEQ ID NOS: 71

<210> SEQ ID NO 1
<211> LENGTH: 1770
<212> TYPE: DNA
<213> ORGANISM: Homo sapiens

<400> SEQUENCE: 1

```
gaggagtgga ttacatattc caacagttgt tattacattg gtaaggaaag aagaacttgg      60
gaagaaagag tttgctggcc tgtgcttcga agaactctga tctgctttct atagataatg     120
aggaagaaat ggtatgtgtg gggacttccc agttggctgt aagttgccat ttgaactaaa     180
cgaaatagat caggaactga ggacatatct aaattttcta gttttataga aggcttttat     240
ccacaagaat caagatcttc cctctctgag caggaatcct ttgtgcattg aagactttag     300
attcctctct gcggtagacg tgcacttata agtatttgat ggggtggatt cgtggtcgga     360
ggtctcgaca cagctgggag atgagtgaat ttcataatta taacttggat ctgaagaaga     420
```

-continued

```
gtgattttc  aacacgatgg  caaaagcaaa  gatgtccagt  agtcaaaagc  aaatgtagag    480
aaaatgcatc  tccattttt   ttctgctgct  tcatcgctgt  agccatggga  atccgtttca    540
ttattatggt  agcaatatgg  agtgctgtat  tcctaaactc  attattcaac  caagaagttc    600
aaattccctt  gaccgaaagt  tactgtggcc  catgtcctaa  aaactggata  tgttacaaaa    660
ataactgcta  ccaattttt   gatgagagta  aaaactggta  tgagagccag  gcttcttgta    720
tgtctcaaaa  tgccagcctt  ctgaaagtat  acagcaaaga  ggaccaggat  ttacttaaac    780
tggtgaagtc  atatcattgg  atgggactag  tacacattcc  aacaaatgga  tcttggcagt    840
gggaagatgg  ctccattctc  tcacccaacc  tactaacaat  aattgaaatg  cagaagggag    900
actgtgcact  ctatgcctcg  agctttaaag  gctatataga  aaactgttca  actccaaata    960
catacatctg  catgcaaagg  actgtgtaaa  gatgatcaac  catctcaata  aaagccagga   1020
acagagaaga  gattacacca  gcggtaacac  tgccaaccga  gactaaagga  aacaaacaaa   1080
aacaggacaa  aatgaccaaa  gactgtcaga  tttcttagac  tccacaggac  caaaccatag   1140
aacaatttca  ctgcaaacat  gcatgattct  ccaagacaaa  agaagagaga  tcctaaaggc   1200
aattcagata  tccccaaggc  tgcctctccc  accacaagcc  cagagtggat  gggctggggg   1260
aggggtgctg  ttttaatttc  taaaggtagg  accaacaccc  aggggatcag  tgaaggaaga   1320
gaaggccagc  agatcagtga  gagtgcaacc  ccaccctcca  caggaaattg  cctcatgggc   1380
agggccacag  cagagagaca  cagcatgggc  agtgccttcc  ctgcctgtgg  gggtcatgct   1440
gccacttta   atgggtcctc  cacccaacgg  ggtcagggag  gtggtgctgc  cccagtgggc   1500
catgattatc  ttaaaggcat  tattctccag  ccttaagatc  ttaggacgtt  tcctttgcta   1560
tgatttgtac  ttgcttgagt  cccatgactg  tttctcttcc  tctctttctt  ccttttggaa   1620
tagtaatatc  catcctatgt  ttgtcccact  attgtatttt  ggaagcacat  aacttgtttg   1680
gtttcacagg  ttcacagtta  agaaggaatt  ttgcctctga  ataaatagaa  tcttgagtct   1740
catgcaaaaa  aaaaaaaaaa  aaaaaaaaaa                                      1770
```

<210> SEQ ID NO 2
<211> LENGTH: 216
<212> TYPE: PRT
<213> ORGANISM: Homo sapiens

<400> SEQUENCE: 2

```
Met Gly Trp Ile Arg Gly Arg Arg Ser Arg His Ser Trp Glu Met Ser
1               5                  10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125
```

```
Ser Gln Asn Ala Ser Leu Leu Lys Val Tyr Ser Lys Glu Asp Gln Asp
    130                 135                 140
Leu Leu Lys Leu Val Lys Ser Tyr His Trp Met Gly Leu Val His Ile
145                 150                 155                 160
Pro Thr Asn Gly Ser Trp Gln Trp Glu Asp Gly Ser Ile Leu Ser Pro
                165                 170                 175
Asn Leu Leu Thr Ile Ile Glu Met Gln Lys Gly Asp Cys Ala Leu Tyr
            180                 185                 190
Ala Ser Ser Phe Lys Gly Tyr Ile Glu Asn Cys Ser Thr Pro Asn Thr
        195                 200                 205
Tyr Ile Cys Met Gln Arg Thr Val
    210                 215
```

<210> SEQ ID NO 3
<211> LENGTH: 1344
<212> TYPE: DNA
<213> ORGANISM: Homo sapiens

<400> SEQUENCE: 3

```
gaggtgcagc tggtggagtc tgggggaggc ctggtcaagc ctgggggtc cctgagactc      60
tcctgtgcag cctctggatt caccttcagt agctatagca tgaactgggt ccgccaggct    120
ccagggaagg ggctggagtg ggtctcatcc attactagta gtagtagtta catatactac    180
gcagactcag tgaagggccg attcaccatc tccagagaca cgccaagaa ctcactgtat     240
ctgcaaatga acagcctgag agccgaggac acggctgtgt attactgtgc gagagatagg    300
cgatattttg actggttccc tcttgactac cggggccagg gaaccctggt caccgtctcc    360
tcagctagca ccaagggccc atccgtcttc ccctggcgc cctgctccag gagcacctcc     420
gagagcacag ccgccctggg ctgcctggtc aaggactact ccccgaacc ggtgacggtg     480
tcgtggaact caggcgccct gaccagcggc gtgcacacct tcccggctgt cctacagtcc    540
tcaggactct actccctcag cagcgtggtg accgtgccct ccagcagctt gggcacgaag    600
acctacacct gcaacgtaga tcacaagccc agcaacacca aggtggacaa gagagttgag    660
tccaaatatg gtccccatg cccaccatgc ccagcacctg agttcctggg ggaccatca     720
gtcttcctgt tccccccaaa acccaaggac actctcatga tctcccggac ccctgaggtc    780
acgtgcgtgg tggtggacgt gagccaggaa gaccccgagg tccagttcaa ctggtacgtg    840
gatggcgtgg aggtgcataa tgccaagaca aagccgcggg aggagcagtt caacagcacg    900
taccgtgtgg tcagcgtcct caccgtcctg caccaggact ggctgaacgg caaggagtac    960
aagtgcaagg tctccaacaa aggcctcccg tcctccatcg agaaaccat ctccaaagcc    1020
aaagggcagc cccgagagcc acaggtgtac accctgcccc catcccagga ggagatgacc   1080
aagaaccagg tcagcctgac ctgcctggtc aaaggcttct accccagcga catcgccgtg   1140
gagtgggaga gcaatgggca gccggagaac aactacaaga ccacgcctcc cgtgctggac   1200
tccgacggct ccttcttcct ctacagcagg ctaaccgtgg acaagagcag gtggcaggag   1260
gggaatgtct tctcatgctc cgtgatgcat gaggctctgc acaaccacta cacacagaag   1320
agcctctccc tgtctctggg taaa                                          1344
```

<210> SEQ ID NO 4
<211> LENGTH: 642
<212> TYPE: DNA
<213> ORGANISM: Homo sapiens

<400> SEQUENCE: 4

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatggtt acccgtacac ttttggccag   300
gggaccaagc tggagatcaa acgtacgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540 ctgagcaaag cagactacga aaacacaaa gtctacgcct gcgaagtcac ccatcagggc   600
ctgagctcgc ccgtcacaaa gagcttcaac aggggagagt gt                      642

<210> SEQ ID NO 5
<211> LENGTH: 1347
<212> TYPE: DNA
<213> ORGANISM: Homo sapiens

<400> SEQUENCE: 5
gaggtgcagc tggtggagtc tgggggaggt gtggtacggc ctggggggtc cctgagactc    60
tcctgtgcag cctctggatt cacctttgat gattatggca tgacctgggt ccgccaagct   120
ccagggaagg gctggagtg gtctctggt attaattgga atggtggtag cacaggttat   180
gcagactctg tgaagggccg attcaccatc tccagagaca cgccaagaa ctccctgtat   240 ctgcaaatga acagtctgag agccgaggac acggccttgt attactgtgc gagagagagg   300
gagttatact actactacta cggtttggac gtctggggcc aagggaccac ggtcaccgtc   360
tcctcagcta gcaccaaggg cccatccgtc ttccccctgg cgccctgctc caggagcacc   420
tccgagagca cagccgccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagcac ctgagttcct ggggggacca   720
tcagtcttcc tgttcccccc aaaacccaag gacactctca tgatctcccg gacccctgag   780
gtcacgtgcg tggtggtgga cgtgagccag gaagacccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctaaccg tggacaagag caggtggcag  1260
gaggggaatg tcttctcatg ctccgtgatg catgaggctc tgcacaacca ctacacacag  1320
aagagcctct ccctgtctct gggtaaa                                      1347

<210> SEQ ID NO 6
```

<211> LENGTH: 645
<212> TYPE: DNA
<213> ORGANISM: Homo sapiens

<400> SEQUENCE: 6

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccatt cactttcggc   300
cctgggacca aagtggatat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgt                   645
```

<210> SEQ ID NO 7
<211> LENGTH: 448
<212> TYPE: PRT
<213> ORGANISM: Homo sapiens

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Thr Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Tyr Phe Asp Trp Phe Pro Leu Asp Tyr Arg Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
```

```
            225                 230                 235                 240
        Val Phe Leu Phe Pro Pro Lys Pro Lys Asp Thr Leu Met Ile Ser Arg
                        245                 250                 255

Thr Pro Glu Val Thr Cys Val Val Val Asp Val Ser Gln Glu Asp Pro
                        260                 265                 270

Glu Val Gln Phe Asn Trp Tyr Val Asp Gly Val Glu Val His Asn Ala
                        275                 280                 285

Lys Thr Lys Pro Arg Glu Glu Gln Phe Asn Ser Thr Tyr Arg Val Val
                    290                 295                 300

Ser Val Leu Thr Val Leu His Gln Asp Trp Leu Asn Gly Lys Glu Tyr
        305                 310                 315                 320

Lys Cys Lys Val Ser Asn Lys Gly Leu Pro Ser Ser Ile Glu Lys Thr
                        325                 330                 335

Ile Ser Lys Ala Lys Gly Gln Pro Arg Glu Pro Gln Val Tyr Thr Leu
                        340                 345                 350

Pro Pro Ser Gln Glu Met Thr Lys Asn Gln Val Ser Leu Thr Cys
                        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Arg Leu Thr Val Asp Lys Ser
                        405                 410                 415

Arg Trp Gln Glu Gly Asn Val Phe Ser Cys Ser Val Met His Glu Ala
                        420                 425                 430

Leu His Asn His Tyr Thr Gln Lys Ser Leu Ser Leu Ser Leu Gly Lys
                        435                 440                 445

<210> SEQ ID NO 8
<211> LENGTH: 214
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 9
<211> LENGTH: 449
<212> TYPE: PRT
<213> ORGANISM: Homo sapiens

<400> SEQUENCE: 9

Glu Val Gln Leu Val Glu Ser Gly Gly Gly Val Val Arg Pro Gly Gly
1               5                   10                  15
Ser Leu Arg Leu Ser Cys Ala Ala Ser Gly Phe Thr Phe Asp Asp Tyr
            20                  25                  30
Gly Met Thr Trp Val Arg Gln Ala Pro Gly Lys Gly Leu Glu Trp Val
        35                  40                  45
Ser Gly Ile Asn Trp Asn Gly Ser Thr Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Arg Glu Arg Glu Leu Tyr Tyr Tyr Tyr Tyr Gly Leu Asp Val Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Ser Thr Tyr Arg Val
    290                 295                 300
Val Ser Val Leu Thr Val Leu His Gln Asp Trp Leu Asn Gly Lys Glu
305                 310                 315                 320
```

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 10
<211> LENGTH: 215
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 11

```
<211> LENGTH: 121
<212> TYPE: PRT
<213> ORGANISM: Homo sapiens

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Thr Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Tyr Phe Asp Trp Phe Pro Leu Asp Tyr Arg Gly
            100                 105                 110

Gln Gly Thr Leu Val Thr Val Ser Ser
        115                 120

<210> SEQ ID NO 12
<211> LENGTH: 108
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Tyr Pro Tyr
                85                  90                  95

Thr Phe Gly Gln Gly Thr Lys Leu Glu Ile Lys Arg
            100                 105

<210> SEQ ID NO 13
<211> LENGTH: 122
<212> TYPE: PRT
<213> ORGANISM: Homo sapiens

<400> SEQUENCE: 13

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Glu Arg Glu Leu Tyr Tyr Tyr Tyr Gly Leu Asp Val Trp
            100                 105                 110

Gly Gln Gly Thr Thr Val Thr Val Ser Ser
            115                 120
```

<210> SEQ ID NO 14
<211> LENGTH: 109
<212> TYPE: PRT
<213> ORGANISM: Homo sapiens

<400> SEQUENCE: 14

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Thr Phe Gly Pro Gly Thr Lys Val Asp Ile Lys Arg
            100                 105
```

<210> SEQ ID NO 15
<211> LENGTH: 5
<212> TYPE: PRT
<213> ORGANISM: Homo sapiens

<400> SEQUENCE: 15

```
Ser Tyr Ser Met Asn
  1               5
```

<210> SEQ ID NO 16
<211> LENGTH: 17
<212> TYPE: PRT
<213> ORGANISM: Homo sapiens

<400> SEQUENCE: 16

```
Ser Ile Thr Ser Ser Ser Ser Tyr Ile Tyr Tyr Ala Asp Ser Val Lys
  1               5                  10                  15

Gly
```

<210> SEQ ID NO 17
<211> LENGTH: 12
<212> TYPE: PRT
<213> ORGANISM: Homo sapiens

<400> SEQUENCE: 17

```
Asp Arg Arg Tyr Phe Asp Trp Phe Pro Leu Asp Tyr
  1               5                  10
```

<210> SEQ ID NO 18
<211> LENGTH: 11

```
<212> TYPE: PRT
<213> ORGANISM: Homo sapiens

<400> SEQUENCE: 18

Arg Ala Ser Gln Gly Ile Ser Ser Trp Leu Ala
1               5                   10

<210> SEQ ID NO 19
<211> LENGTH: 7
<212> TYPE: PRT
<213> ORGANISM: Homo sapiens

<400> SEQUENCE: 19

Ala Ala Ser Ser Leu Gln Ser
1               5

<210> SEQ ID NO 20
<211> LENGTH: 9
<212> TYPE: PRT
<213> ORGANISM: Homo sapiens

<400> SEQUENCE: 20

Gln Gln Tyr Asn Gly Tyr Pro Tyr Thr
1               5

<210> SEQ ID NO 21
<211> LENGTH: 5
<212> TYPE: PRT
<213> ORGANISM: Homo sapiens

<400> SEQUENCE: 21

Asp Tyr Gly Met Thr
1               5

<210> SEQ ID NO 22
<211> LENGTH: 17
<212> TYPE: PRT
<213> ORGANISM: Homo sapiens

<400> SEQUENCE: 22

Gly Ile Asn Trp Asn Gly Gly Ser Thr Gly Tyr Ala Asp Ser Val Lys
1               5                   10                  15

Gly

<210> SEQ ID NO 23
<211> LENGTH: 13
<212> TYPE: PRT
<213> ORGANISM: Homo sapiens

<400> SEQUENCE: 23

Glu Arg Glu Leu Tyr Tyr Tyr Tyr Tyr Gly Leu Asp Val
1               5                   10

<210> SEQ ID NO 24
<211> LENGTH: 12
<212> TYPE: PRT
<213> ORGANISM: Homo sapiens

<400> SEQUENCE: 24

Arg Ala Ser Gln Ser Val Ser Ser Ser Tyr Leu Ala
1               5                   10

<210> SEQ ID NO 25
<211> LENGTH: 7
```

```
<212> TYPE: PRT
<213> ORGANISM: Homo sapiens

<400> SEQUENCE: 25

Gly Ala Ser Ser Arg Ala Thr
1               5

<210> SEQ ID NO 26
<211> LENGTH: 9
<212> TYPE: PRT
<213> ORGANISM: Homo sapiens

<400> SEQUENCE: 26

Gln Gln Tyr Gly Ser Ser Pro Phe Thr
1               5

<210> SEQ ID NO 27
<211> LENGTH: 111
<212> TYPE: PRT
<213> ORGANISM: Homo sapiens

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Trp Gly Gln Gly Thr Leu Val Thr Val Ser Ser
            100                 105                 110

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 29
```

```
<211> LENGTH: 118
<212> TYPE: PRT
<213> ORGANISM: Homo sapiens

<400> SEQUENCE: 29

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser
        115

<210> SEQ ID NO 30
<211> LENGTH: 108
<212> TYPE: PRT
<213> ORGANISM: Homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 31
<211> LENGTH: 98
<212> TYPE: PRT
<213> ORGANISM: Homo sapiens

<400> SEQUENCE: 31

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 32
<211> LENGTH: 5
<212> TYPE: PRT
<213> ORGANISM: Homo sapiens

<400> SEQUENCE: 32

Arg Tyr Phe Asp Trp
 1               5

<210> SEQ ID NO 33
<211> LENGTH: 13
<212> TYPE: PRT
<213> ORGANISM: Homo sapiens

<400> SEQUENCE: 33

Asp Tyr Trp Gly Gln Gly Thr Leu Val Thr Val Ser Ser
 1               5                  10

<210> SEQ ID NO 34
<211> LENGTH: 95
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 35
<211> LENGTH: 12
<212> TYPE: PRT
<213> ORGANISM: Homo sapiens

<400> SEQUENCE: 35

Tyr Thr Phe Gly Gln Gly Thr Lys Leu Glu Ile Lys
 1               5                  10

<210> SEQ ID NO 36
<211> LENGTH: 98
<212> TYPE: PRT
<213> ORGANISM: Homo sapiens

<400> SEQUENCE: 36

Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
```

```
                    20                  25                  30
Gly Met Ser Trp Val Arg Gln Ala Pro Gly Lys Gly Leu Glu Trp Val
            35                  40                  45
Ser Gly Ile Asn Trp Asn Gly Gly Ser Thr Gly Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr His Cys
                85                  90                  95
Ala Arg

<210> SEQ ID NO 37
<211> LENGTH: 20
<212> TYPE: PRT
<213> ORGANISM: Homo sapiens

<400> SEQUENCE: 37

Tyr Tyr Tyr Tyr Tyr Gly Met Asp Val Trp Gly Gln Gly Thr Thr Val
1               5                   10                  15
Thr Val Ser Ser
            20

<210> SEQ ID NO 38
<211> LENGTH: 96
<212> TYPE: PRT
<213> ORGANISM: Homo sapiens

<400> SEQUENCE: 38

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95

<210> SEQ ID NO 39
<211> LENGTH: 12
<212> TYPE: PRT
<213> ORGANISM: Homo sapiens

<400> SEQUENCE: 39

Phe Thr Phe Gly Pro Gly Thr Lys Val Asp Ile Lys
1               5                   10

<210> SEQ ID NO 40
<211> LENGTH: 442
<212> TYPE: PRT
<213> ORGANISM: Homo sapiens

<400> SEQUENCE: 40

Gln Val His Leu Gln Glu Ser Gly Pro Gly Leu Val Lys Pro Ser Glu
1               5                   10                  15
Thr Leu Ser Leu Thr Cys Thr Val Ser Asp Asp Ser Ile Ser Ser Tyr
```

-continued

```
                20                  25                  30
Tyr Trp Ser Trp Ile Arg Gln Pro Pro Gly Lys Gly Leu Glu Trp Ile
            35                  40                  45

Gly His Ile Ser Tyr Ser Gly Ser Ala Asn Tyr Asn Pro Ser Leu Lys
        50                  55                  60

Ser Arg Val Thr Ile Ser Val Asp Thr Ser Lys Asn Gln Phe Ser Leu
 65                 70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
        210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```

```
<210> SEQ ID NO 41
<211> LENGTH: 215
<212> TYPE: PRT
<213> ORGANISM: Homo sapiens

<400> SEQUENCE: 41

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 42
<211> LENGTH: 450
<212> TYPE: PRT
<213> ORGANISM: Homo sapiens

<400> SEQUENCE: 42

Glu Val Gln Leu Val Gln Ser Gly Ala Glu Val Lys Glu Pro Gly Glu
1               5                   10                  15

Ser Leu Lys Ile Ser Cys Lys Asn Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Gly Arg Leu Thr Met Phe Arg Gly Ile Ile Ile Gly Tyr Phe Asp Tyr
            100                 105                 110
```

-continued

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 43
<211> LENGTH: 214
<212> TYPE: PRT
<213> ORGANISM: Homo sapiens

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr

```
                20                  25                  30
Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
             50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 44
<211> LENGTH: 115
<212> TYPE: PRT
<213> ORGANISM: Homo sapiens

<400> SEQUENCE: 44

Gln Val His Leu Gln Glu Ser Gly Pro Gly Leu Val Lys Pro Ser Glu
 1               5                  10                  15

Thr Leu Ser Leu Thr Cys Thr Val Ser Asp Asp Ser Ile Ser Ser Tyr
                20                  25                  30

Tyr Trp Ser Trp Ile Arg Gln Pro Pro Gly Lys Gly Leu Glu Trp Ile
                35                  40                  45

Gly His Ile Ser Tyr Ser Gly Ser Ala Asn Tyr Asn Pro Ser Leu Lys
             50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Asn Trp Asp Asp Ala Phe Asn Ile Trp Gly Gln Gly Thr Met Val Thr
                100                 105                 110

Val Ser Ser
        115

<210> SEQ ID NO 45
<211> LENGTH: 108
<212> TYPE: PRT
<213> ORGANISM: Homo sapiens

<400> SEQUENCE: 45

Glu Ile Val Leu Thr Gln Ser Pro Gly Thr Leu Ser Leu Ser Pro Gly
```

```
            1               5                  10                 15
        Glu Arg Ala Thr Leu Ser Cys Arg Ala Ser Gln Ser Val Ser Ser Ser
                        20                  25                  30

Tyr Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                        50                  55                  60

Gly Ser Gly Ser Gly Thr Asp Phe Thr Leu Thr Ile Ser Arg Leu Glu
         65                 70                  75                  80

Pro Glu Asp Phe Ala Val Tyr Tyr Cys Gln Gln Tyr Gly Ser Ser Pro
                        85                  90                  95

Trp Thr Phe Gly Gln Gly Thr Lys Val Glu Ile Lys
                       100                 105

<210> SEQ ID NO 46
<211> LENGTH: 123
<212> TYPE: PRT
<213> ORGANISM: Homo sapiens

<400> SEQUENCE: 46

Glu Val Gln Leu Val Gln Ser Gly Ala Glu Val Lys Glu Pro Gly Glu
          1               5                  10                 15

Ser Leu Lys Ile Ser Cys Lys Asn Ser Gly Tyr Ser Phe Thr Asn Tyr
                        20                  25                  30

Trp Val Gly Trp Val Arg Gln Met Pro Gly Lys Gly Leu Glu Trp Met
                        35                  40                  45

Gly Ile Ile Tyr Pro Gly Asp Ser Asp Thr Arg Tyr Ser Pro Ser Phe
                        50                  55                  60

Gln Gly Gln Val Thr Ile Ser Ala Asp Lys Ser Ile Asn Thr Ala Tyr
         65                 70                  75                  80

Leu Gln Trp Ser Ser Leu Lys Ala Ser Asp Thr Ala Met Tyr Tyr Cys
                        85                  90                  95

Gly Arg Leu Thr Met Phe Arg Gly Ile Ile Gly Tyr Phe Asp Tyr
                       100                 105                 110

Trp Gly Gln Gly Thr Leu Val Thr Val Ser Ser
                       115                 120

<210> SEQ ID NO 47
<211> LENGTH: 107
<212> TYPE: PRT
<213> ORGANISM: Homo sapiens

<400> SEQUENCE: 47

Glu Ile Val Leu Thr Gln Ser Pro Ala Thr Leu Ser Leu Ser Pro Gly
          1               5                  10                 15

Glu Arg Ala Thr Leu Ser Cys Arg Ala Ser Gln Ser Val Ser Ser Tyr
                        20                  25                  30

Leu Ala Trp Tyr Gln Gln Lys Pro Gly Gln Ala Pro Arg Leu Leu Ile
                        35                  40                  45

Tyr Asp Ala Ser Asn Arg Ala Thr Gly Ile Pro Ala Arg Phe Ser Gly
                        50                  55                  60

Ser Gly Ser Gly Thr Asp Phe Thr Leu Thr Ile Ser Ser Leu Glu Pro
         65                 70                  75                  80

Glu Asp Phe Ala Val Tyr Tyr Cys Gln Gln Arg Ser Asn Trp Pro Trp
                        85                  90                  95

Thr Phe Gly Gln Gly Thr Lys Val Glu Ile Lys
```

<210> SEQ ID NO 48
<211> LENGTH: 5
<212> TYPE: PRT
<213> ORGANISM: Homo sapiens

<400> SEQUENCE: 48

Ser Tyr Tyr Trp Ser
1               5

<210> SEQ ID NO 49
<211> LENGTH: 16
<212> TYPE: PRT
<213> ORGANISM: Homo sapiens

<400> SEQUENCE: 49

His Ile Ser Tyr Ser Gly Ser Ala Asn Tyr Asn Pro Ser Leu Lys Ser
1               5                   10                  15

<210> SEQ ID NO 50
<211> LENGTH: 7
<212> TYPE: PRT
<213> ORGANISM: Homo sapiens

<400> SEQUENCE: 50

Trp Asp Asp Ala Phe Asn Ile
1               5

<210> SEQ ID NO 51
<211> LENGTH: 12
<212> TYPE: PRT
<213> ORGANISM: Homo sapiens

<400> SEQUENCE: 51

Arg Ala Ser Gln Ser Val Ser Ser Ser Tyr Leu Ala
1               5                   10

<210> SEQ ID NO 52
<211> LENGTH: 7
<212> TYPE: PRT
<213> ORGANISM: Homo sapiens

<400> SEQUENCE: 52

Gly Ala Ser Ser Arg Ala Thr
1               5

<210> SEQ ID NO 53
<211> LENGTH: 9
<212> TYPE: PRT
<213> ORGANISM: Homo sapiens

<400> SEQUENCE: 53

Gln Gln Tyr Gly Ser Ser Pro Trp Thr
1               5

<210> SEQ ID NO 54
<211> LENGTH: 5
<212> TYPE: PRT
<213> ORGANISM: Homo sapiens

<400> SEQUENCE: 54

Asn Tyr Trp Val Gly
1               5

<210> SEQ ID NO 55
<211> LENGTH: 17
<212> TYPE: PRT
<213> ORGANISM: Homo sapiens

<400> SEQUENCE: 55

Ile Ile Tyr Pro Gly Asp Ser Asp Thr Arg Tyr Ser Pro Ser Phe Gln
1               5                   10                  15

Gly

<210> SEQ ID NO 56
<211> LENGTH: 14
<212> TYPE: PRT
<213> ORGANISM: Homo sapiens

<400> SEQUENCE: 56

Leu Thr Met Phe Arg Gly Ile Ile Gly Tyr Phe Asp Tyr
1               5                   10

<210> SEQ ID NO 57
<211> LENGTH: 11
<212> TYPE: PRT
<213> ORGANISM: Homo sapiens

<400> SEQUENCE: 57

Arg Ala Ser Gln Ser Val Ser Ser Tyr Leu Ala
1               5                   10

<210> SEQ ID NO 58
<211> LENGTH: 7
<212> TYPE: PRT
<213> ORGANISM: Homo sapiens

<400> SEQUENCE: 58

Asp Ala Ser Asn Arg Ala Thr
1               5

<210> SEQ ID NO 59
<211> LENGTH: 9
<212> TYPE: PRT
<213> ORGANISM: Homo sapiens

<400> SEQUENCE: 59

Gln Gln Arg Ser Asn Trp Pro Trp Thr
1               5

<210> SEQ ID NO 60
<211> LENGTH: 116
<212> TYPE: PRT
<213> ORGANISM: Homo sapiens

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

-continued

Lys Leu Ser Ser Val Thr Ala Ala Asp Thr Ala Val Tyr Tyr Cys Ala
                85                  90                  95

Arg Asn Trp Gly Asp Ala Phe Asp Ile Trp Gly Gln Gly Thr Met Val
            100                 105                 110

Thr Val Ser Ser
        115

<210> SEQ ID NO 61
<211> LENGTH: 108
<212> TYPE: PRT
<213> ORGANISM: Homo sapiens

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 62
<211> LENGTH: 122
<212> TYPE: PRT
<213> ORGANISM: Homo sapiens

<400> SEQUENCE: 62

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Thr Met Val Arg Gly Val Ile Ile Tyr Phe Asp Tyr Trp
            100                 105                 110

Gly Gln Gly Thr Leu Val Thr Val Ser Ser
        115                 120

<210> SEQ ID NO 63
<211> LENGTH: 107
<212> TYPE: PRT
<213> ORGANISM: Homo sapiens

<400> SEQUENCE: 63

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105
```

<210> SEQ ID NO 64
<211> LENGTH: 97
<212> TYPE: PRT
<213> ORGANISM: Homo sapiens

<400> SEQUENCE: 64

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

<210> SEQ ID NO 65
<211> LENGTH: 16
<212> TYPE: PRT
<213> ORGANISM: Homo sapiens

<400> SEQUENCE: 65

```
Asp Ala Phe Asp Val Trp Gly Gln Gly Thr Met Val Thr Val Ser Ser
1               5                   10                  15
```

<210> SEQ ID NO 66
<211> LENGTH: 12
<212> TYPE: PRT
<213> ORGANISM: Homo sapiens

<400> SEQUENCE: 66

```
Trp Thr Phe Gly Gln Gly Thr Lys Val Glu Ile Lys
1               5                   10
```

<210> SEQ ID NO 67
<211> LENGTH: 98
<212> TYPE: PRT
<213> ORGANISM: Homo sapiens

<400> SEQUENCE: 67

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 68
<211> LENGTH: 9
<212> TYPE: PRT
<213> ORGANISM: Homo sapiens

<400> SEQUENCE: 68

Ile Thr Met Val Arg Gly Val Ile Ile
1               5

<210> SEQ ID NO 69
<211> LENGTH: 95
<212> TYPE: PRT
<213> ORGANISM: Homo sapiens

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 70
<211> LENGTH: 220
<212> TYPE: PRT
<213> ORGANISM: Artificial Sequence
<220> FEATURE:
<223> OTHER INFORMATION: Synthetic

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asp Pro Ser Asp Ile Tyr Thr Asn Tyr Ala Gln Lys Phe
    50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ile Tyr Asp Gly Tyr Tyr Val Tyr Gly Met Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val
            210                 215                 220

<210> SEQ ID NO 71
<211> LENGTH: 214
<212> TYPE: PRT
<213> ORGANISM: Artificial Sequence
<220> FEATURE:
<223> OTHER INFORMATION: Synthetic

<400> SEQUENCE: 71

Tyr Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Lys Thr Leu Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
-continued

Ser Thr Leu Thr Leu Ser Lys Ala Asp Tyr Glu Lys His Lys Val Tyr
            180             185                 190

Ala Cys Glu Val Thr His Gln Gly Leu Ser Ser Pro Val Thr Lys Ser
        195             200                 205

Phe Asn Arg Gly Glu Cys
    210
```